United States Patent
Aparicio et al.

(10) Patent No.: US 10,934,580 B2
(45) Date of Patent: Mar. 2, 2021

(54) MOLECULAR QUALITY ASSURANCE METHODS FOR USE IN SEQUENCING

(71) Applicant: CANEXIA HEALTH INC., Vancouver (CA)

(72) Inventors: Samuel Aparicio, Vancouver (CA); Sohrab Shah, Vancouver (CA); Rosalia Aguirre-Hernandez, Vancouver (CA); Leah Prentice, Vancouver (CA); Patrick Franchini, Vancouver (CA); Jaswinder Singh Khattra, Vancouver (CA); Tong He, Vancouver (CA)

(73) Assignee: CANEXIA HEALTH INC., Vancouver (CA)

( * ) Notice: Subject to any disclaimer, the term of this patent is extended or adjusted under 35 U.S.C. 154(b) by 0 days.

(21) Appl. No.: 15/760,537

(22) PCT Filed: Sep. 23, 2016

(86) PCT No.: PCT/IB2016/055722
§ 371 (c)(1),
(2) Date: Mar. 15, 2018

(87) PCT Pub. No.: WO2017/051387
PCT Pub. Date: Mar. 30, 2017

(65) Prior Publication Data
US 2018/0258479 A1    Sep. 13, 2018

Related U.S. Application Data

(60) Provisional application No. 62/233,074, filed on Sep. 25, 2015.

(51) Int. Cl.
*C12Q 1/6851* (2018.01)
*C12Q 1/686* (2018.01)
*C12Q 1/6869* (2018.01)
*G16B 25/00* (2019.01)

(52) U.S. Cl.
CPC .......... *C12Q 1/6851* (2013.01); *C12Q 1/686* (2013.01); *C12Q 1/6869* (2013.01); *G16B 25/00* (2019.02)

(58) Field of Classification Search
CPC .............. C12Q 1/686; C12Q 2537/157; C12Q 2563/179; C12Q 1/6851; C12Q 1/6869; G16B 25/00
See application file for complete search history.

(56) References Cited

U.S. PATENT DOCUMENTS

2007/0172873 A1    7/2007    Brenner et al.

FOREIGN PATENT DOCUMENTS

| CN | 104762399 | 7/2015 |
| WO | 2011/140510 | 11/2011 |
| WO | 2013130512 A2 | 9/2013 |
| WO | 2015100427 A1 | 7/2015 |
| WO | 2015112619 A1 | 7/2015 |

OTHER PUBLICATIONS

Hamady et al (Nat. Methods, 5(3) 235-237), March (Year: 2008).*
Chao et al (PLOS One 10(6): 30125471, 1-24, Jun. 11, (Year: 2015).*
Gohl et al (Genetics, vol. 196, pp. 615-623, March (Year: 2014).*
Atschul, Stephen F et al (1997), "Gapped BLAST and PSI-BLAST: a new generation of protein database search programs", Nucleic Acids Res. 25:3389-3402.
Breese MR1, Liu Y. NGSUtils: a software suite for analyzing and manipulating next-generation sequencing datasets. Bioinformatics. Feb. 15, 2013; 29(4):494-6.
Cingolani P1, Platts A, Wang le L, Coon M, Nguyen T, Wang L, Land SJ, Lu X, Ruden DM. A program for annotating and predicting the effects of single nucleotide polymorphisms, SnpEff: SNPs in the genome of *Drosophila melanogaster* strain w1118; iso-2; iso-3. Fly (Austin). Apr.-Jun. 2012;6(2):80-92.
Ding J1, Bashashati A, Roth A, Oloumi A, Tse K, Zeng T, Haffari G, Hirst M, Marra MA, Condon A, Aparicio S, Shah SP. Feature-based classifiers for somatic mutation detection in tumour-normal paired sequencing data. Bioinformatics. Jan. 15, 2012;28(2):167-75. http://doi.org/10.1093/bioinformatics/btr629.
Flip Van Nieuwerburgh et al, "Quantitative Bias in Illumina TruSeq and a Novel Post Amplification Barcoding Strategy for Multiplexed DNA and Small RNA Deep Sequencing", vol. 6, No. 10, Jan. 1, 2011, p. e26969.
Goya, R., Sun, M. G., Morin, R. D., GG, L, Ha, G., Wiegand, K. C., et al. (2010). SNVMix: predicting single nucleotide variants from next-generation sequencing of tumors. Bioinformatics (Oxford, England), 26(6), 730-736. http://doi.org/10.1093/bioinformatics/btq040).
Li H. Aligning sequence reads, clone sequences and assembly contigs with BWA-MEM. (2013). arXiv:1303.3997v1 [q-bio.GN] 3 pages.
Li H1, Handsaker B, Wysoker A, Fennell T, Ruan J, Homer N, Marth G, Abecasis G, Durbin R; 1000 Genome Project Data Processing Subgroup. The Sequence Alignment/Map format and SAMtools. Bioinformatics. Aug. 15, 2009;25 (16):2078-9.
Saunders CT1, Wong WS, Swamy S, Becq J, Murray LJ, Cheetham RK. Strelka: accurate somatic small-variant calling from sequenced tumor-normal sample pairs. Bioinformatics. Jul. 15, 2012;28(14):1811-7.
Tulpan DC and Hoos HH (2003). Hybrid randomized neighbourhoods improve stochastic local search for DNA code design. Lecture Notes in Computer Science 2671:418:433. 16 pages.
Untergasser A, Cutcutache I, Koressaar T, Ye J, Faircloth BC, Remm M and Rozen SG. (2012), Primer3—new capabilities and interfaces. Nucleic Acids Res. 40(15):e115. 12 pages.

(Continued)

*Primary Examiner* — Cynthia B Wilder
(74) *Attorney, Agent, or Firm* — Leason Ellis LLP

(57) ABSTRACT

The present invention relates to quality assurance methods for use in amplification techniques, such as Next Generation Sequencing (NGS).

9 Claims, 27 Drawing Sheets
Specification includes a Sequence Listing.

(56) References Cited

OTHER PUBLICATIONS

Extended European Search Report dated Mar. 1, 2019, issued in corresponding European Application No. 16848253.7. 8 pages.
Office Action dated Sep. 16, 2019 issued in the corresponding Chilean patent application No. 201800756. 7 pages.
Office Action dated Jul. 23, 2019, issued in the corresponding Singaporean patent application No. 11201802137V. 9 pages.
Fox. E.J. et al., "Accuracy of next generation sequencing platforms", Next Gener. Seq. Appl. Jun. 28, 2014 (Feb. 28, 2014). pp. 1-9.
International Search Report and Written Opinion for Application No. PCT/IB2016/055722, dated Jan. 23, 2017, 13 pages.
European Examination Report in corresponding European Patent Application No. 16848253.7 dated Jan. 14, 2020. 4 pages.

\* cited by examiner

| | | subsequence location | | | |
|---|---|---|---|---|---|
| | | (1,2) | (2,3) | ... | (7,8) |
| subsequence composition | AA | $y_{11}= median\{y_j \mid w_j =AAw_3..w_n\}$ | | | |
| | AT | | | | |
| | AG | | | | |
| | AC | | | | |
| | ... | | | | |

(A)

(B)

MOLECULAR QUALITY ASSURANCE METHODS FOR USE IN SEQUENCING

FIELD OF INVENTION

The present invention relates to quality assurance methods.

BACKGROUND OF THE INVENTION

Digital single molecule representation sequencing, often referred to as Next Generation Sequencing (NGS), uses a sequencing by synthesis approach that approximates single molecule DNA sequencing. A feature of NGS methods is that they represent single molecules in the sequences derived. NGS is used for genomic profiling in genomics-based cancer tests.

There are however several aspects of NGS that would benefit from a quality assurance process to establish confidence in allele calls. These aspects include detection of biological and technical bias in allele amplification, detection of poor template or under-representation of template in sequencing, detection of extraneous amplicon contamination, and detection of true low prevalence mutations in the input DNA pool. Quality assurance is a required element of clinical testing and also enables sound research foundations.

Several strategies have been used for counting DNA molecules, such as using stochastic attachment of DNA sequences where the sequence of bases represents a word or code (referred to as barcodes, or molecular barcodes) followed by amplification.

Limitations of the known DNA codeword approaches are that they do not in general address the consequences of a biased set of codeword molecules used for counting, nor the consequences of loss of efficiency in attachment which may be sequence dependent. Additionally, methods are required to incorporate molecular counting into the probabilistic methods for allele detection in NGS sequences (for example those using Bayesian graphical models, such as SNVmix[1] and incorporated into feature based classifiers of sequence variation such as mutationseq[2].

SUMMARY OF THE INVENTION

In one aspect, the present disclosure provides a method of determining the complexity of a nucleic acid template by:
  i) providing a nucleic acid template;
  ii) providing a plurality of primer pairs, including a first primer and a second primer, wherein the first primer includes a sequence complementary to a portion of the nucleic acid template, and the second primer includes a sequence complementary to a portion of the complement of the nucleic acid template;
  iii) attaching a codeword to the 5' end of the first primer, the 5' end of the second primer, or both, to form a codeword-primer molecule, or to the nucleic acid template to form a codeword-template molecule;
  iv) performing an amplification reaction with the paired codeword-primer molecules and the nucleic acid template or with the primer pairs and the codeword-template molecule for a defined number of cycles to obtain an amplification reaction product;
  v) obtaining the sequence of the amplification reaction product at the end of each cycle, at the end of the defined number of cycles, or at an intermediate number of cycles;
  vi) determining the abundance of each codeword present in the amplification reaction product at the end of each cycle, at the end of the defined number of cycles, or at an intermediate number of cycles;
  vii) determining the observed codeword entropy of each cycle; and
  viii) comparing the observed codeword entropy to an estimated codeword entropy,
  to determine the complexity of the nucleic acid template.

In an alternative aspect, the present disclosure provides a method of identifying a true sequence variant by:
  i) providing a nucleic acid template;
  ii) providing a plurality of primer pairs, including a first primer and a second primer, wherein the first primer includes a sequence complementary to a portion of the nucleic acid template, and the second primer includes a sequence complementary to a portion of the complement of the nucleic acid template;
  iii) attaching a codeword to the 5' end of the first primer, the 5' end of the second primer, or both, to form a codeword-primer molecule, or to the nucleic acid template to form a codeword-template molecule;
  iv) performing an amplification reaction with the paired codeword-primer molecules and the nucleic acid template or with the primer pairs and the codeword-template molecule for a defined number of cycles to obtain an amplification reaction product;
  v) obtaining the sequence of the amplification reaction product at the end of each cycle, at the end of the defined number of cycles, or at an intermediate number of cycles;
  vi) determining the abundance of each codeword present in the amplification reaction product at the end of each cycle, at the end of the defined number of cycles, or at an intermediate number of cycles;
  vii) determining the observed codeword entropy of each cycle; and
  viii) performing a supervised classification method based on the results of steps vi) and vii),
  to identify the true sequence variant.

The true sequence variant may be a low prevalence sequence variant.

The nucleic acid template may be a DNA template.

The codeword-primer molecule or the primer may be further attached to an adapter sequence.

A different codeword may be attached to the first and second primer in the primer pair or the same codeword may be attached to the first and second primer in the primer pair.

The codewords may be attached to the nucleic acid template at random.

The observed codeword entropy may be calculated by a diversity index, such as Shannon entropy, the Simpson index, or any other diversity index.

The codewords may be present in a non-uniform pool.

The codewords may be present in a balanced pool obtained as described herein.

The methods as described herein may be used for detecting true sequence variants, amplification process contamination, sample identity mismatch, or codeword pool imbalance.

In an alternative aspect, the present disclosure provides a method for obtaining a balanced pool of codewords comprising:
  i) providing an initial sample comprising a plurality of codewords of a defined length;

ii) providing a target sequence;
iii) providing a plurality of primer pairs comprising a first primer and a second primer, wherein the first primer comprises a sequence complementary to a portion of the target sequence, and the second primer comprises a sequence complementary to a portion of the complement of the target sequence, and wherein each codeword is attached to the 5' end of the first primer, the 5' end of the second primer, or both, to form a paired codeword-primer molecule;
iv) performing an amplification reaction with the paired codeword-primer molecule and the target sequence for a defined number of cycles to obtain an amplification reaction product;
v) obtaining the sequence of the amplification reaction product at the end of each cycle, at the end of the defined number of cycles, or at an intermediate number of cycles;
vi) determining the abundance of each codeword present in the amplification reaction product at the end of each cycle, at the end of the defined number of cycles, or at an intermediate number of cycles;
vii) obtaining measured parameters of codeword performance by:
  a) comparing the abundance from step (vi) with an expected number; and/or
  b) determining the rate of increase in abundance over each preceding amplification cycle; and
using the measured parameters from step (vii) to perform a search in silico using a stochastic local search method to obtain a balanced pool of codewords.

The codeword-primer molecule may be further attached to an adapter sequence.

The codeword length may be from about 4 units to about 21 units.

The initial sample size may be at least 10 codewords.

The initial sample may be a random sample or may be subjected to combinatorial and/or thermodynamic constraints.

The initial sample may include all combinations of the codeword sequence or may include a subset of combinations of the codeword sequence.

The method may be performed using larger pools of codewords or codewords of different lengths.

The method may be performed using a single target sequence or using two or more target sequences.

The method may be performed a single time or may be performed two or more times.

The method may include determination of codeword performance as function of subsequence and location.

The primers may include one or more of the sequences set forth in SEQ ID NOS: 1-146.

In some aspects, the present disclosure provides a set of primer pairs, including a first primer and a second primer, where the first primer includes a sequence set forth in any one of SEQ ID NOS: 1-73 and the second primer includes a sequence set forth in any one of SEQ ID NOS: 74-146.

In some embodiments, primers or primer pairs may be provided in kits, together with suitable reagents for storage, transport, delivery or use of the primers or primer pairs, optionally with instructions for use.

This summary of the invention does not necessarily describe all features of the invention.

BRIEF DESCRIPTION OF THE DRAWINGS

These and other features of the invention will become more apparent from the following description in which reference is made to the appended drawings wherein.

Figure 14:
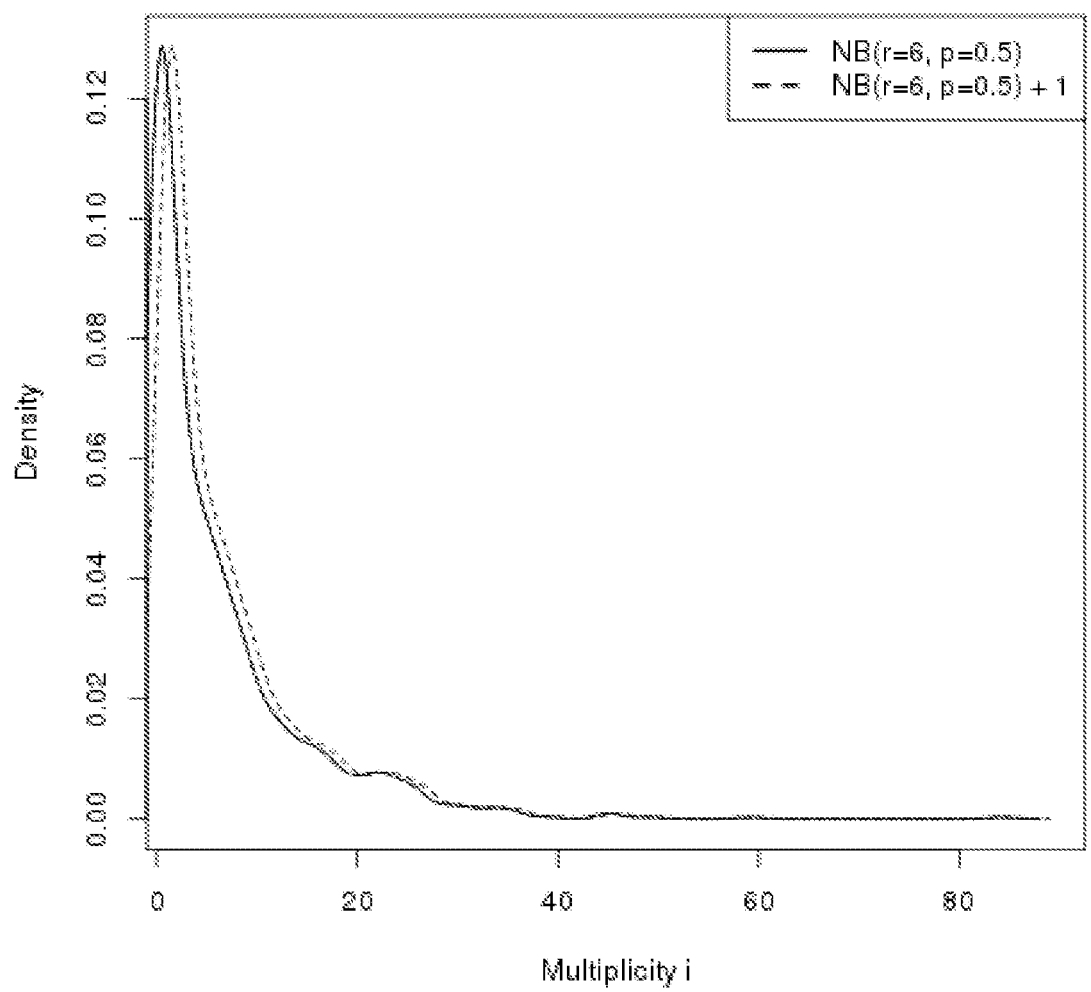
Figure 15:
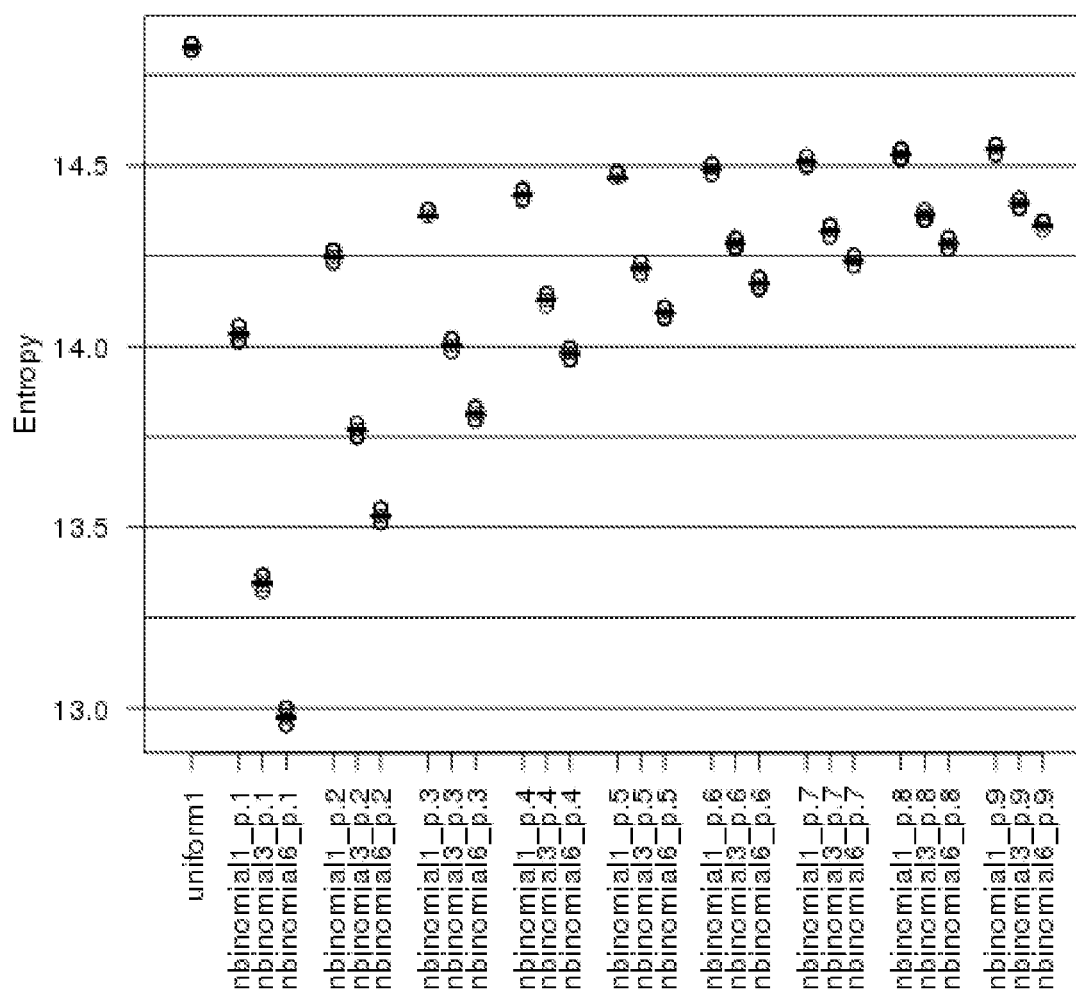

when i~P($\lambda$);

FIG. 14 is a graph showing Negative Binomial distribution models of variation in codeword multiplicity, where the solid curve corresponds to a randomly generated Negative Binomial distribution i~NB(r=6, p=0.5), where $\hat{\mu}[i]$=6.396 and $\hat{\sigma^2}[i]$=85.66, 7 and the dashed curve shows the same distribution with values shifted by one. In this case $\hat{\mu}[i]$=7.396 and $\hat{\sigma^2}[i]$=85.667;

FIG. 15 is a graph showing comparison of codeword entropy distribution in the $4^{th}$ PCR cycle with m=3000 when i~U(1) and i~NB(r, p), where labels in the x-axis correspond to the parameters used to generate each distribution (for instance, nbinomial1_p.1 corresponds to the shifted distribution i~NB(r, p=0.1)+1 with μ=1. That is $$r = 1 * \frac{1 - 0.1}{0.1} = 9);$$

Figure 16:
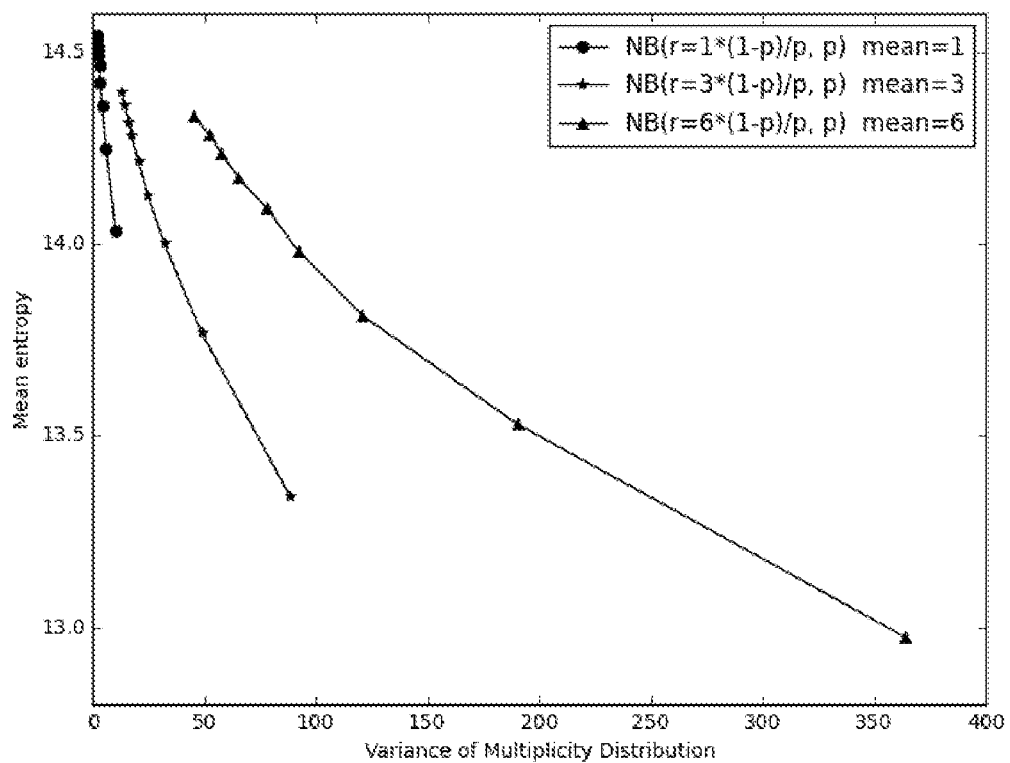
Figure 17A:
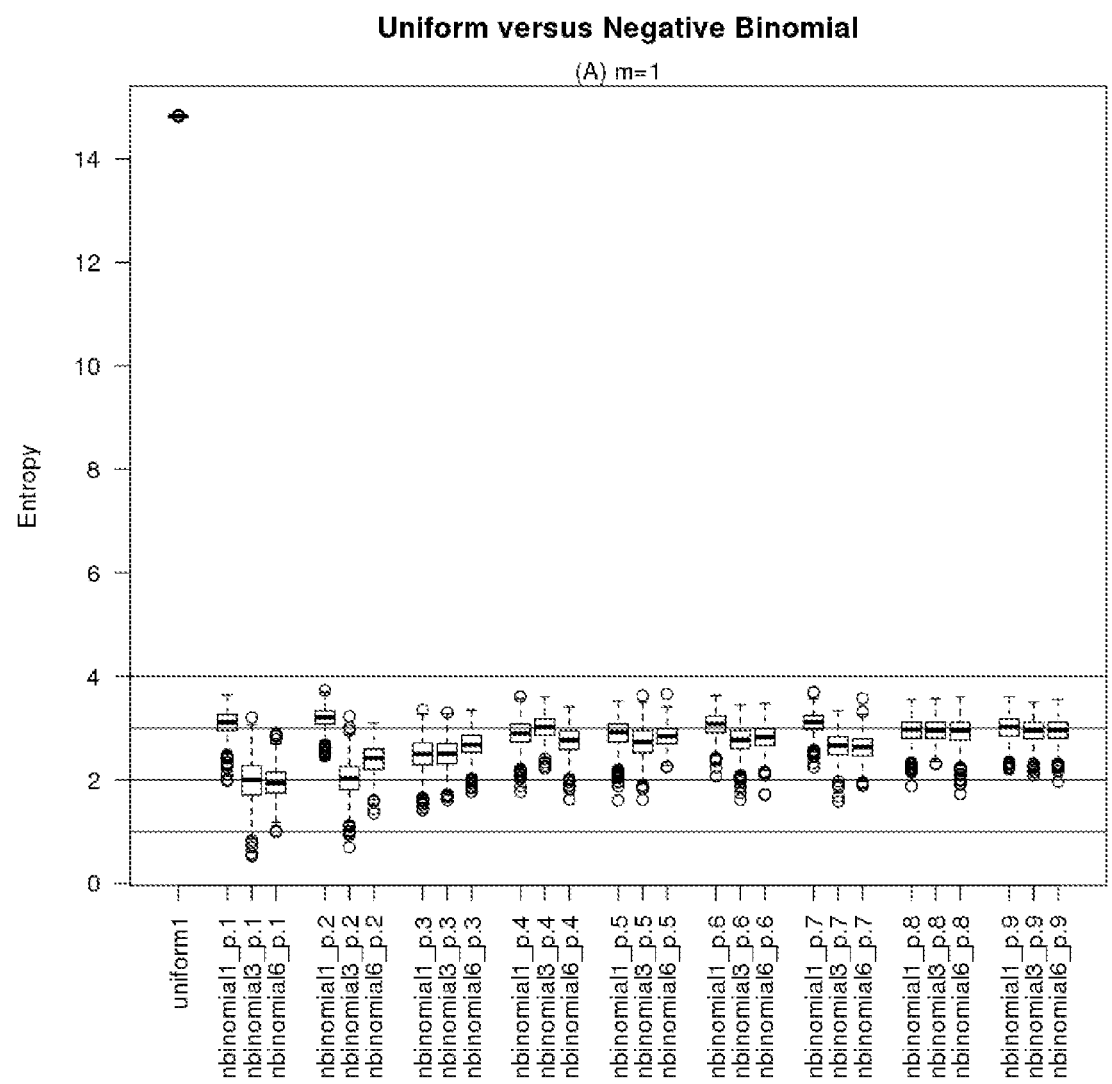
Figure 17B:
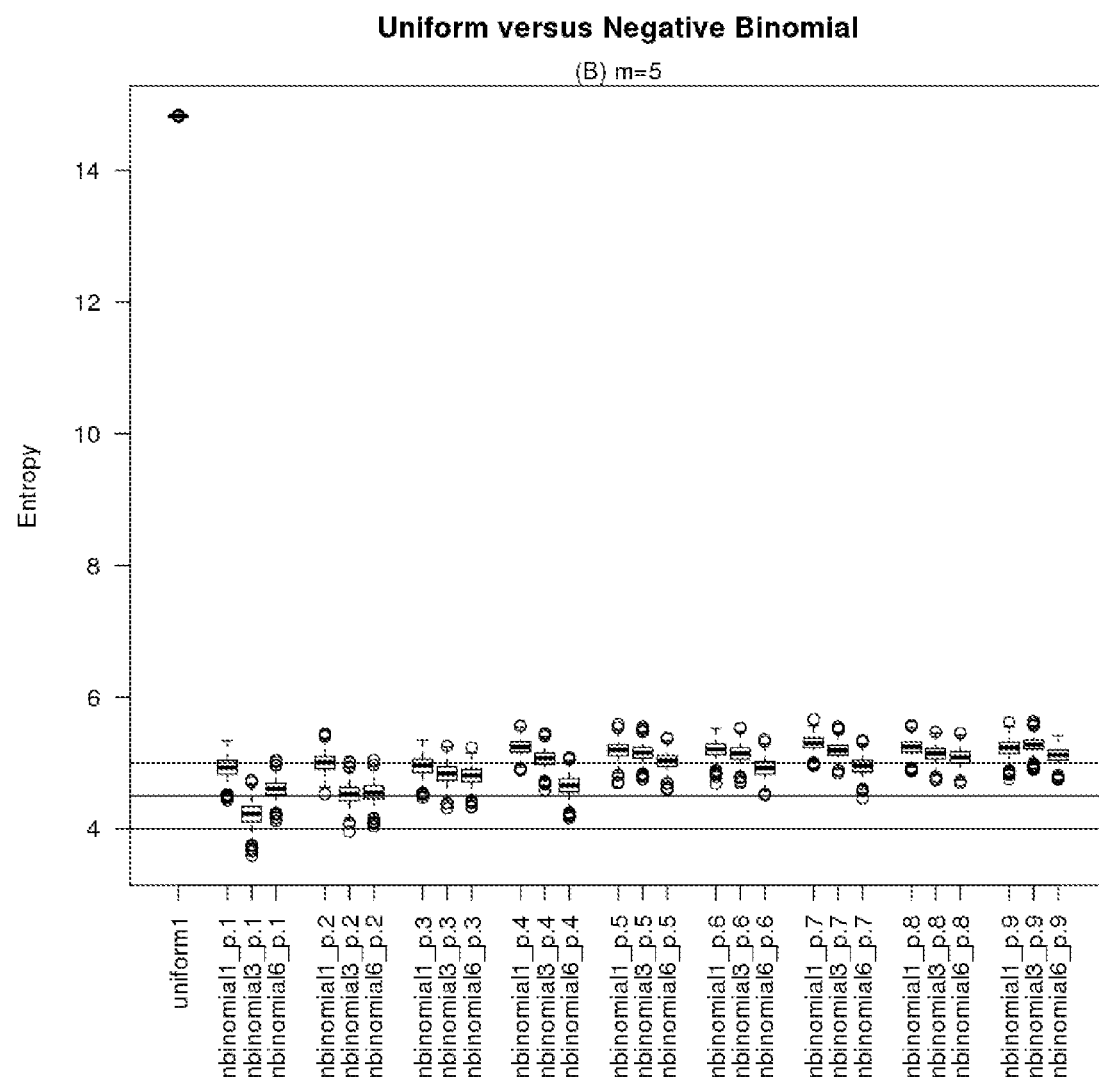
Figure 17C:
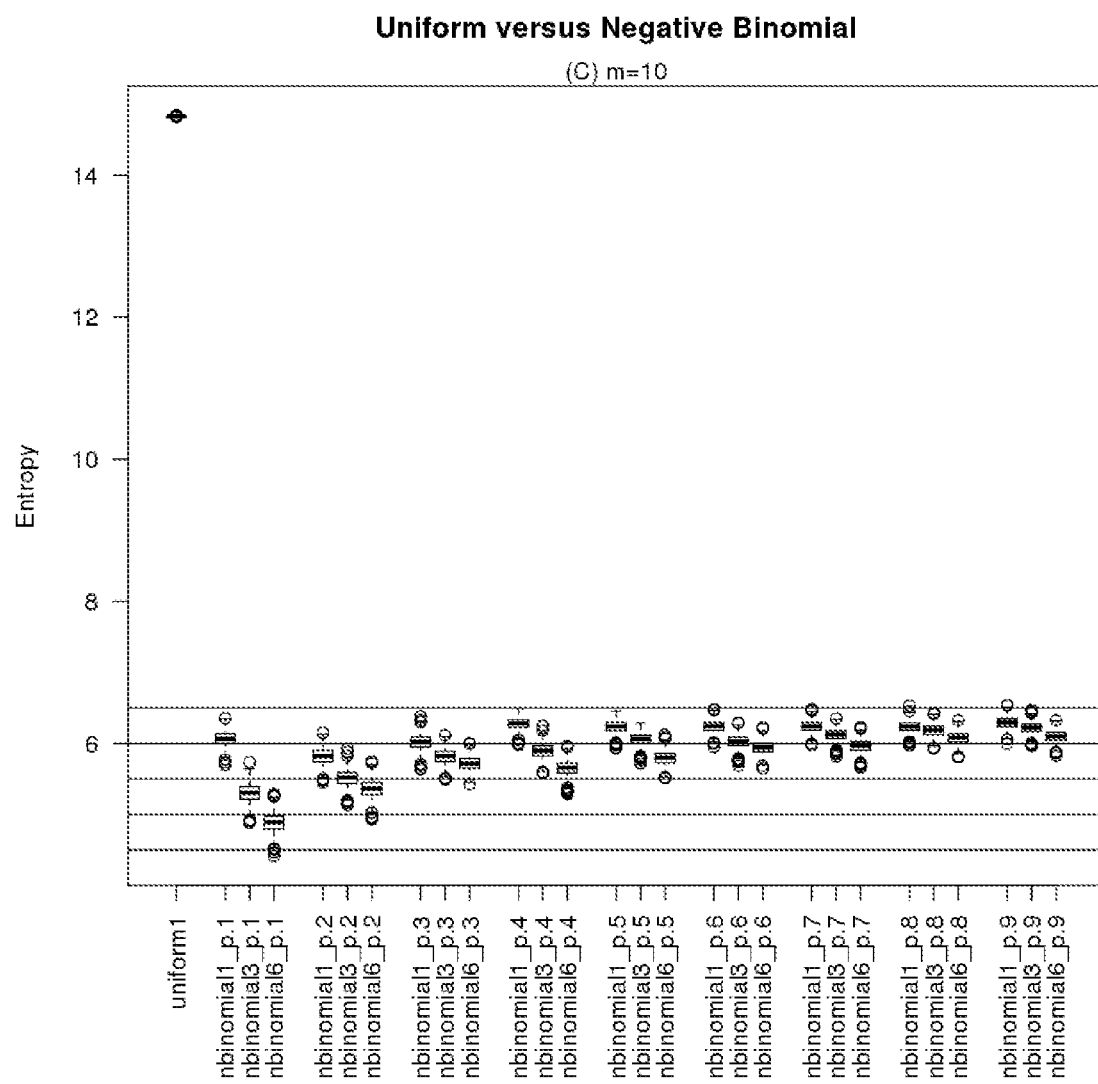
Figure 18A:
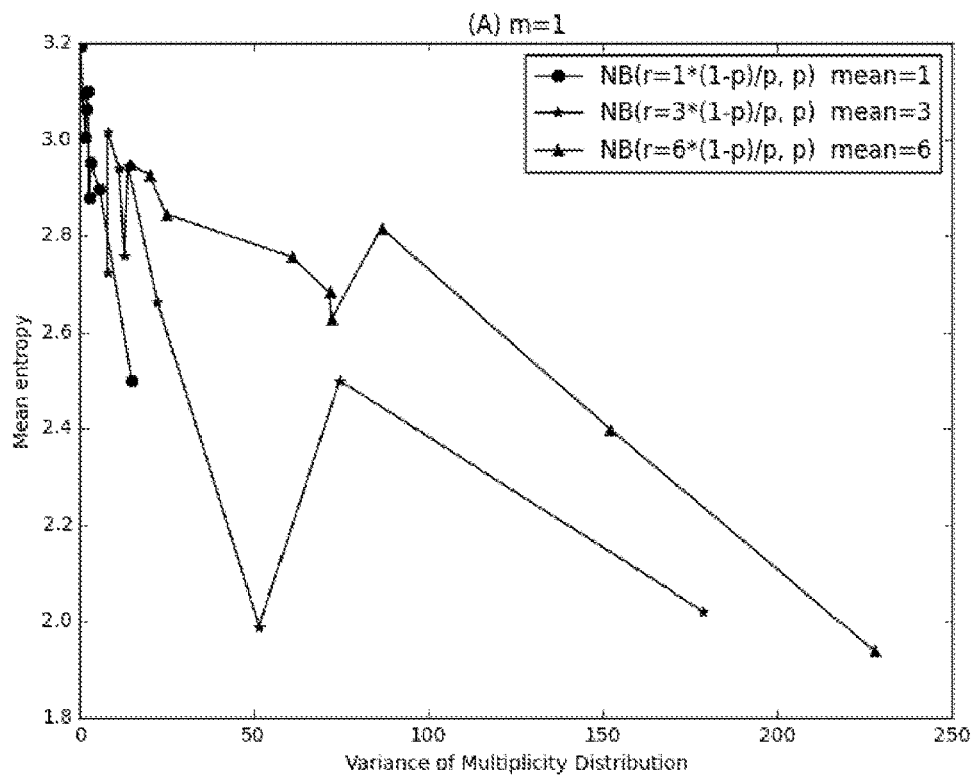
Figure 18B:
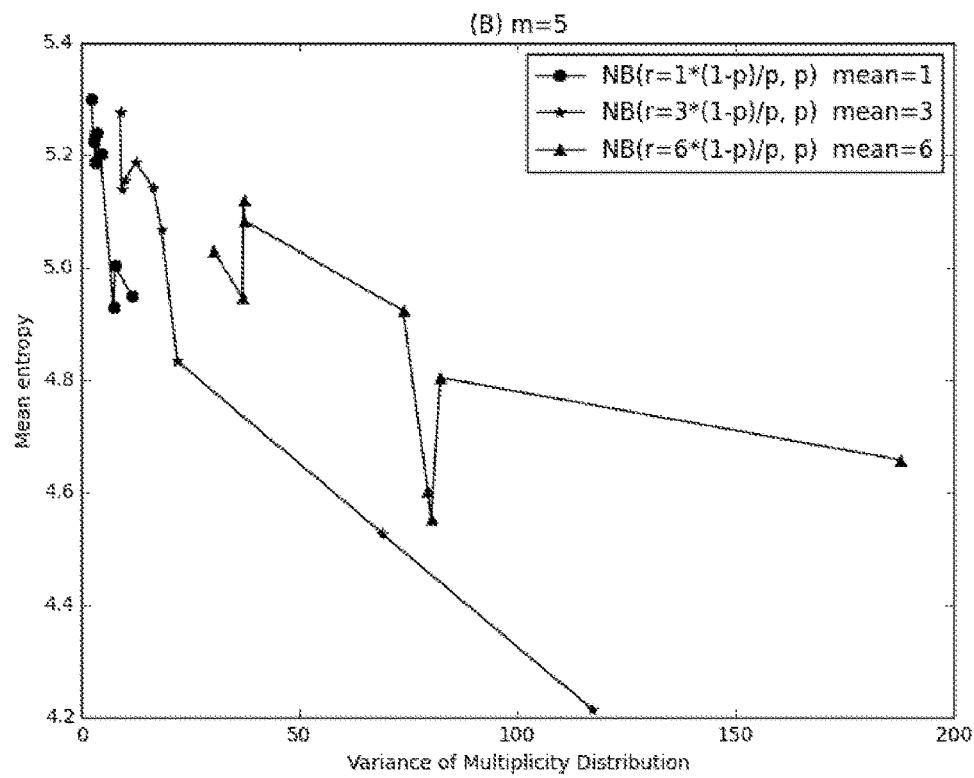
Figure 18C:
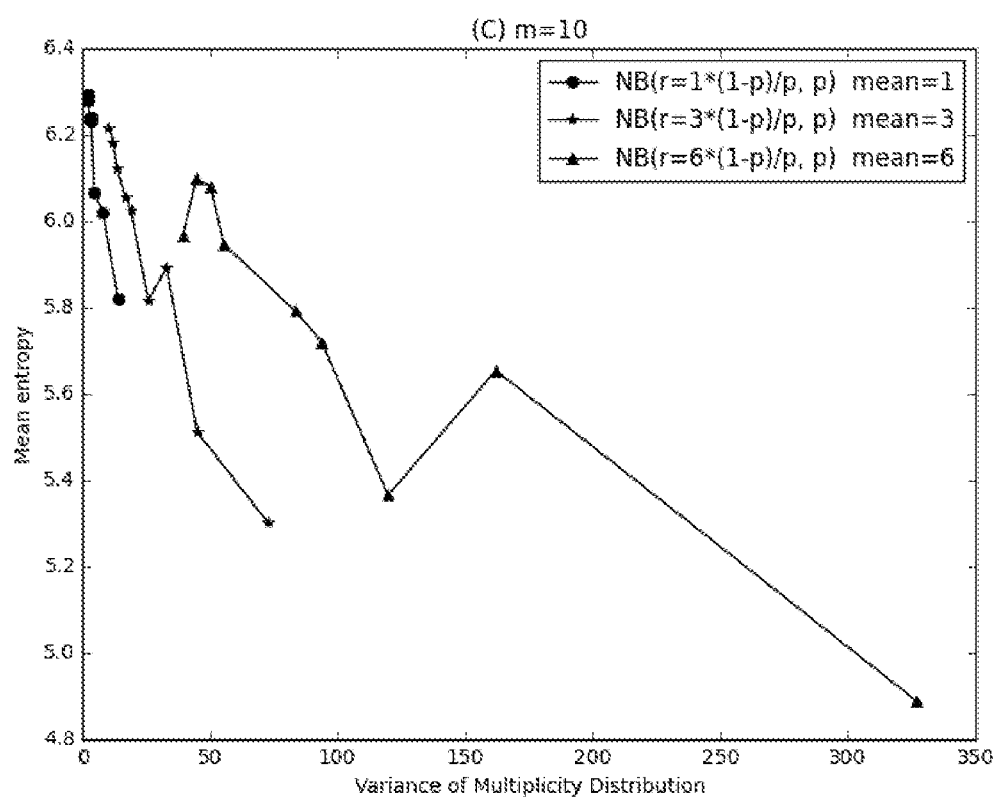
Figure 19:
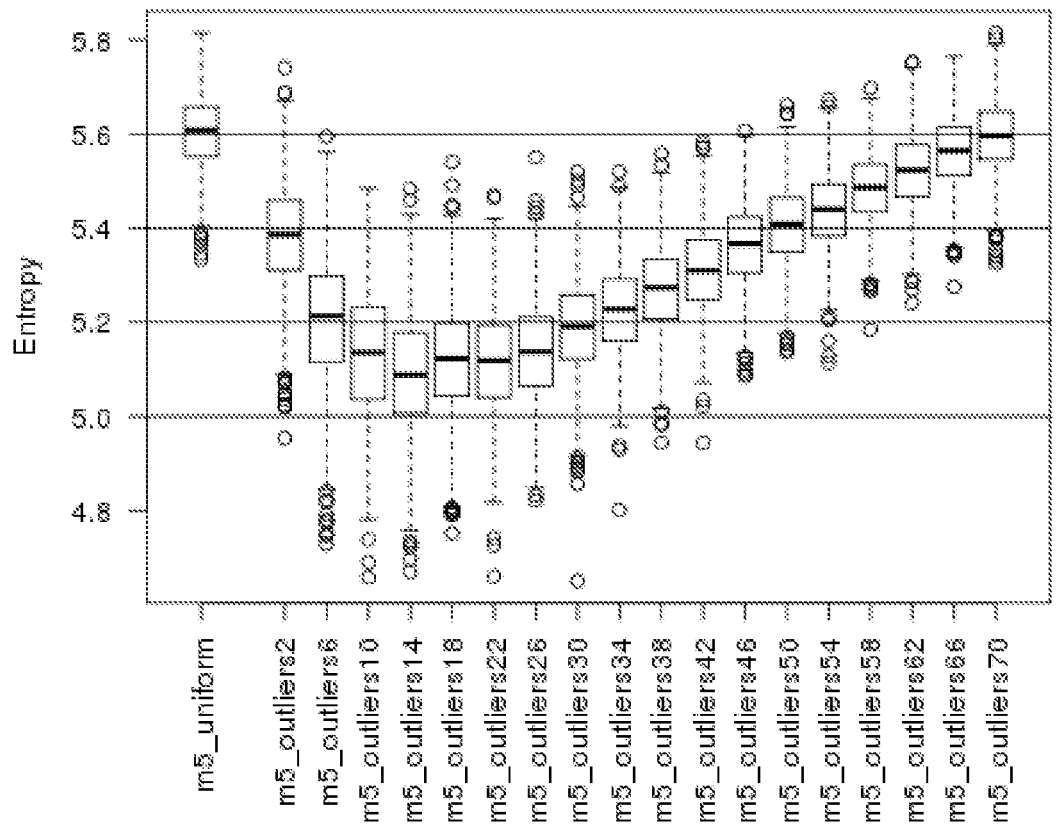
Figure 20:
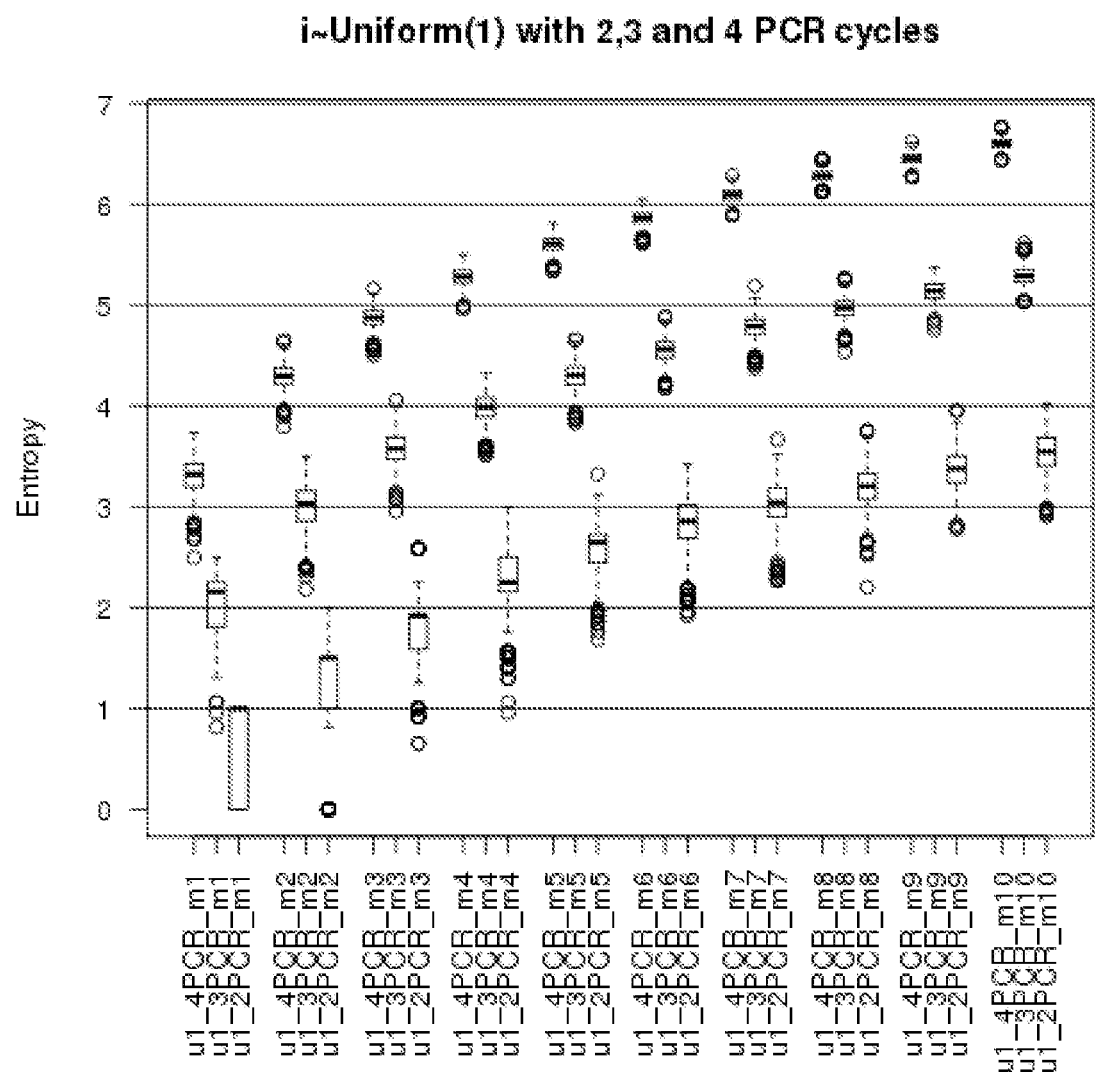
Figure 21A:
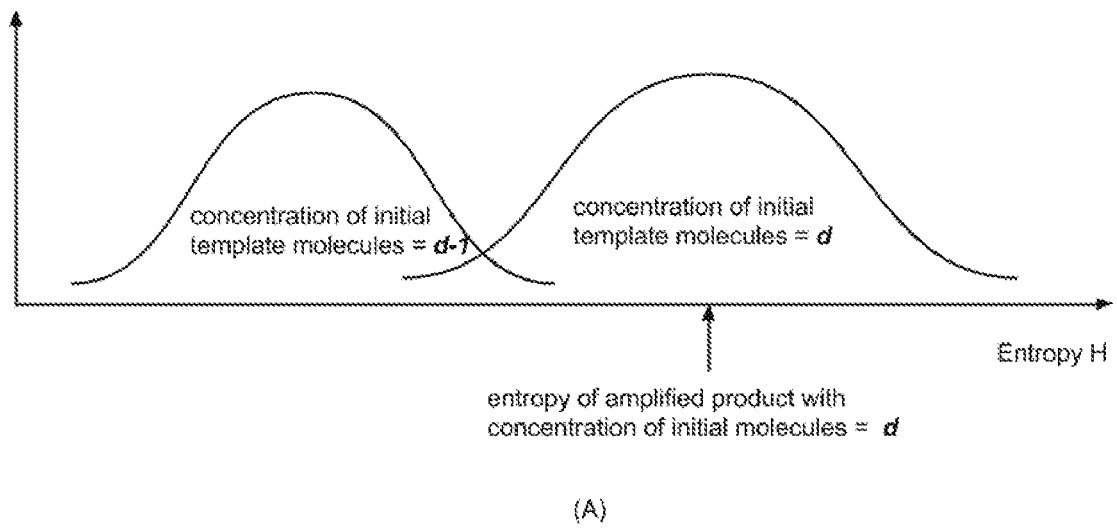
Figure 21B:
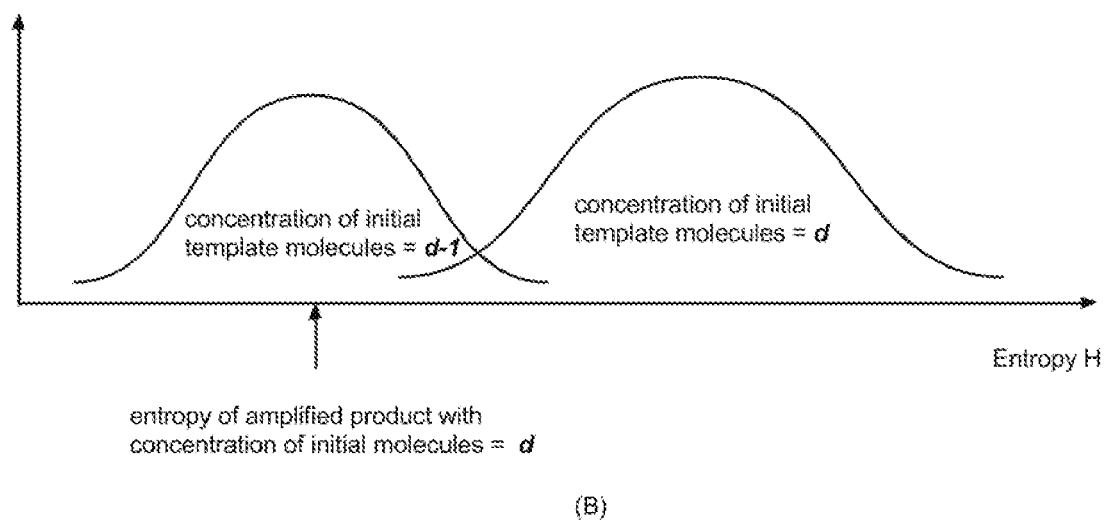

FIG. 16 is a graph showing the relationship between the mean entropy and the variance of the Negative Binomial distributions from FIG. 15;

FIG. 17A is a graph showing codeword entropy distributions when i~NB(r,p) and m=1;

FIG. 17B is a graph showing codeword entropy distributions when i~NB(r,p) and m=5;

FIG. 17C is a graph showing codeword entropy distributions when i~NB(r,p) andm=10;

FIG. 18A is a graph showing correlation of variance of Negative Binomial multiplicity distribution against the mean of the entropy distributions shown in FIG. 17A;

FIG. 18B is a graph showing correlation of variance of Negative Binomial multiplicity distribution against the mean of the entropy distributions shown in FIG. 17B;

FIG. 18C is a graph showing correlation of variance of Negative Binomial multiplicity distribution against the mean of the entropy distributions shown in FIG. 17C;

FIG. 19 is a graph showing comparison of codeword entropy distribution in the $4^{th}$ PCR cycle for i~U(1) and i~U(1) with outliers. The number of outliers ranges between 2 and 70 with random multiplicities that vary between 5 and 7. In every case the initial number of template molecules is m=5 and the total number of unique codewords in the pool is 14*m=70;

FIG. 20 is a graph showing codeword entropy distribution for two, three, and four PCR cycles and different number of initial template molecules m;

FIG. 21A is a graph showing the case when the entropy of the amplified product lies in the expected entropy distribution of the corresponding concentration of initial template molecules;

FIG. 21B is a graph showing the case when the entropy of the amplified product has a lower value and suggests an artifact in the PCR process.

Figure 22:
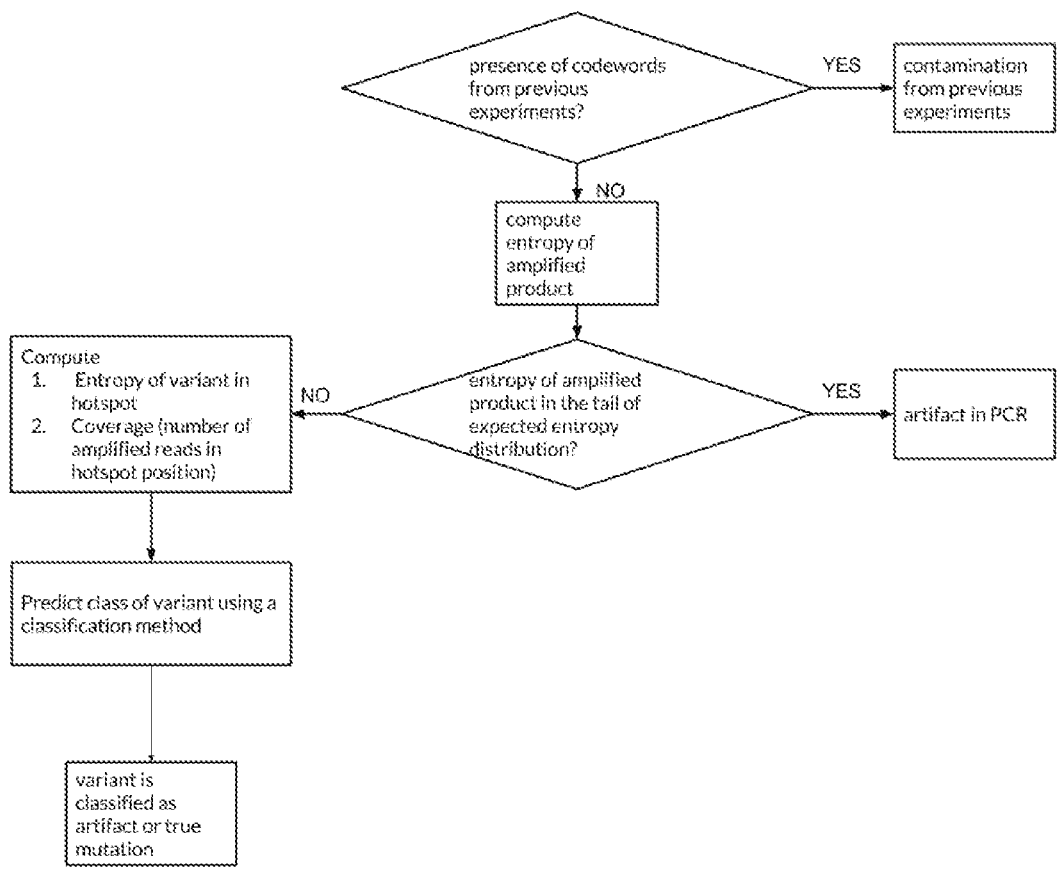
Figure 23A:
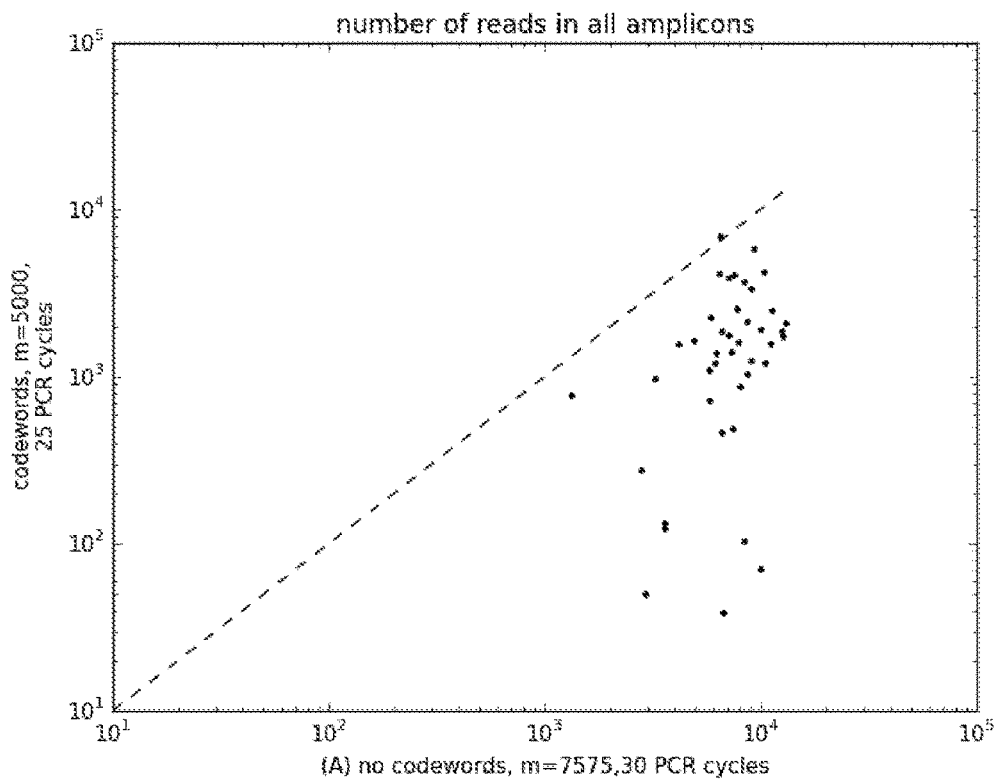
Figure 23B:
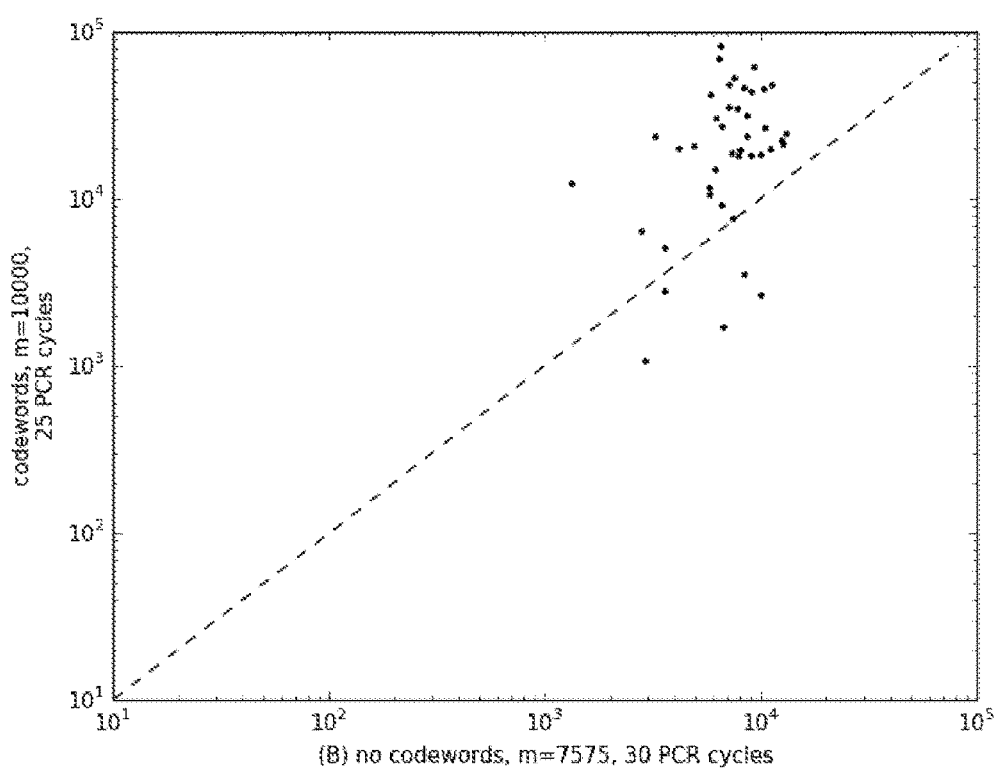
Figure 24A:
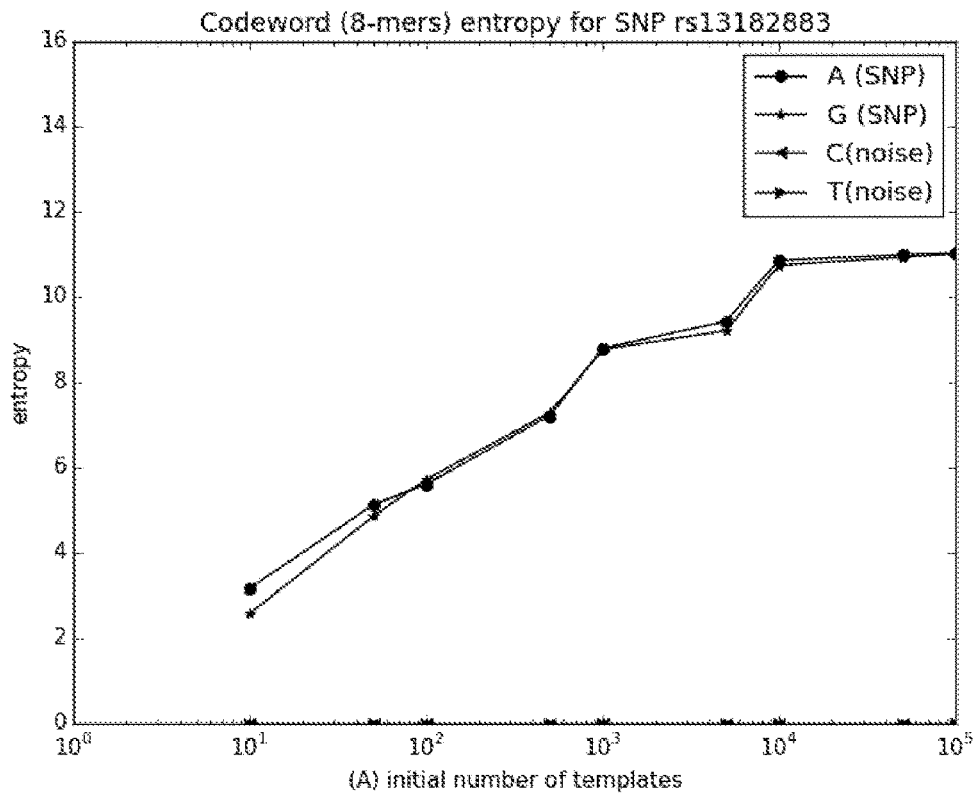
Figure 24B:
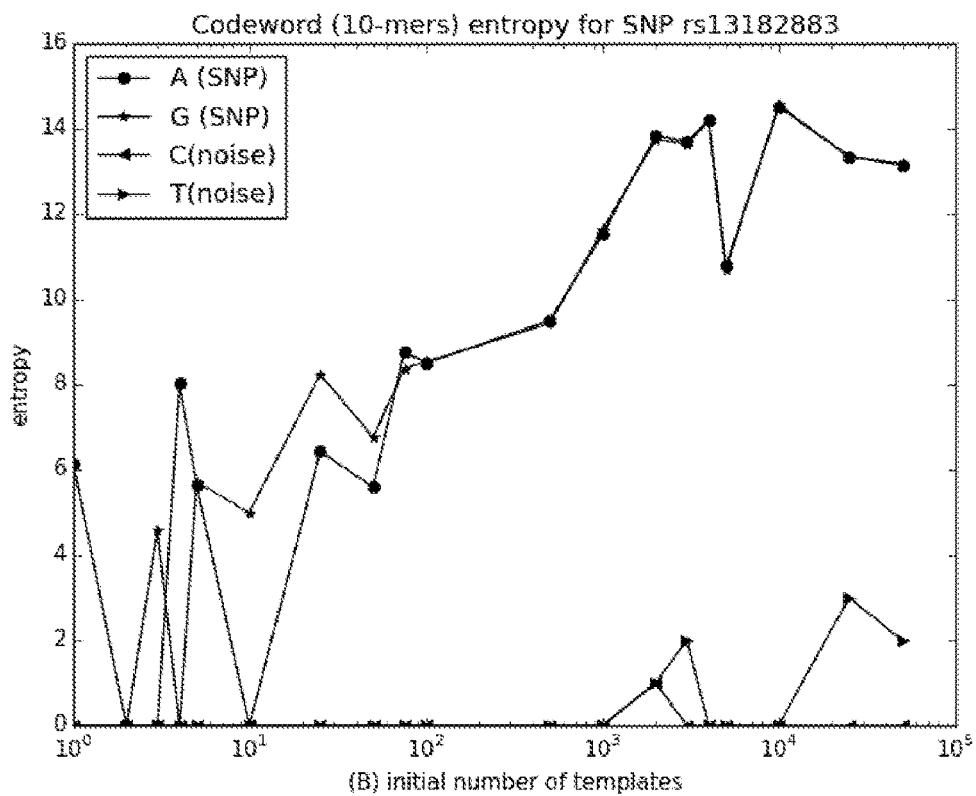
Figure 25:
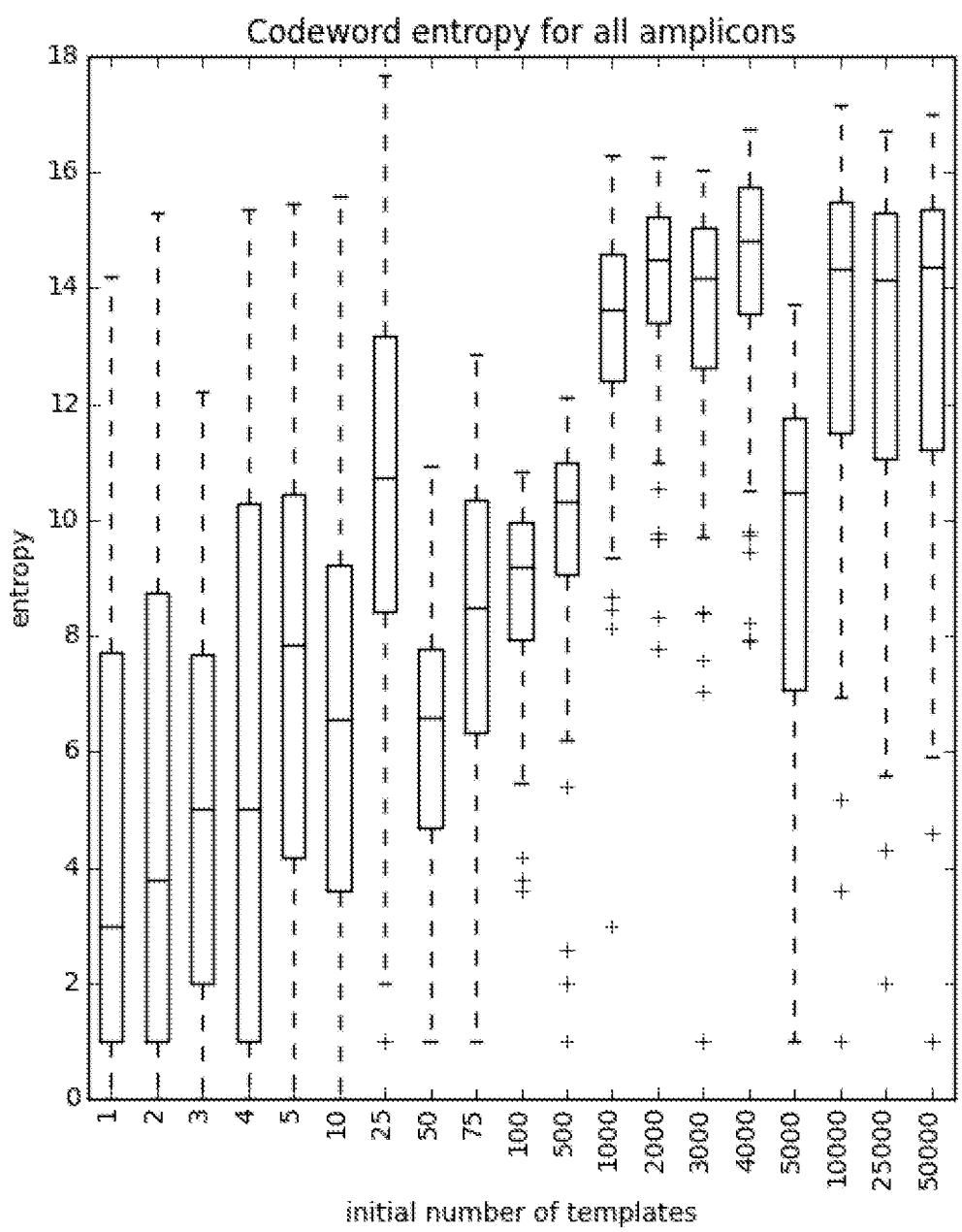
Figure 26:
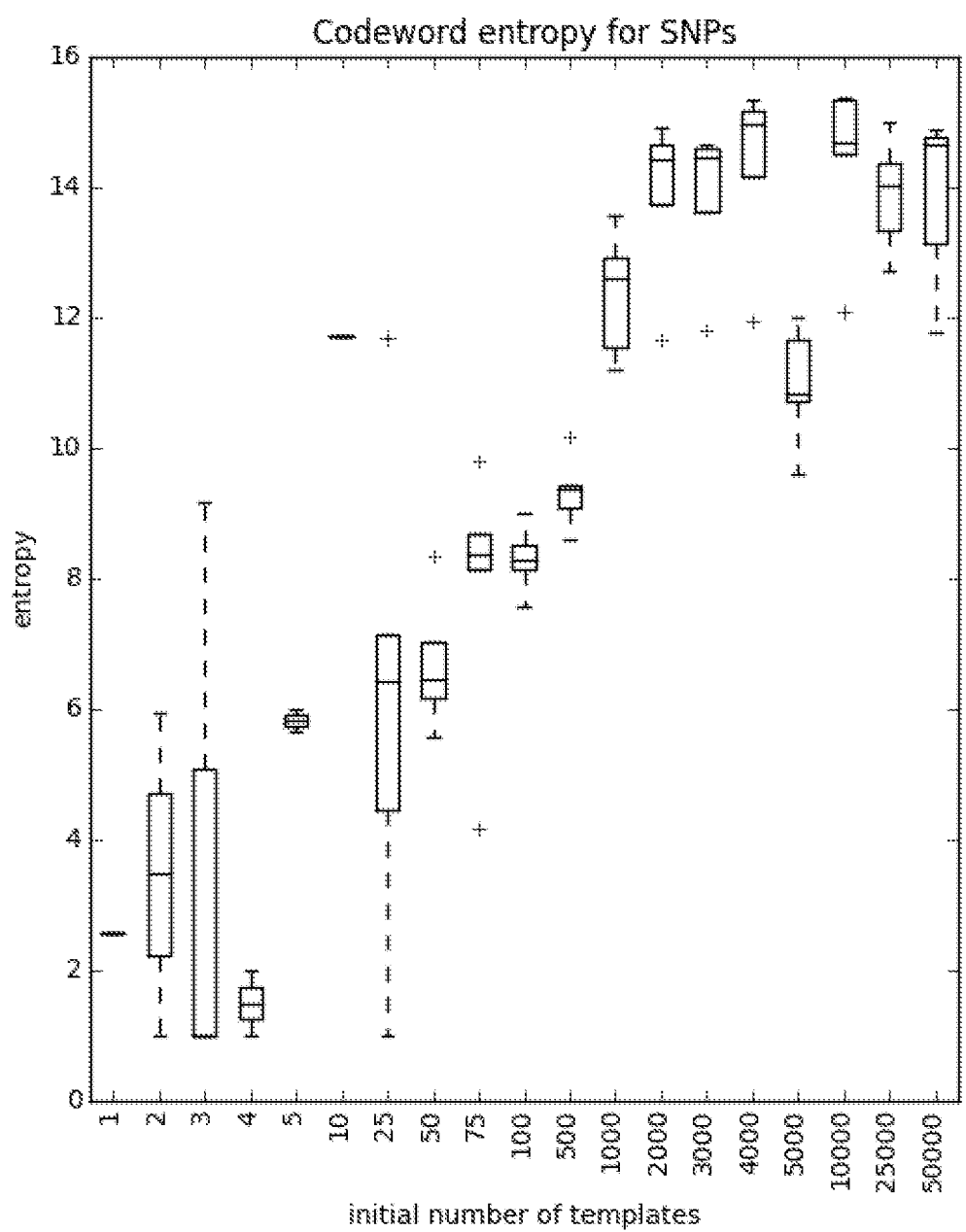
Figure 27:
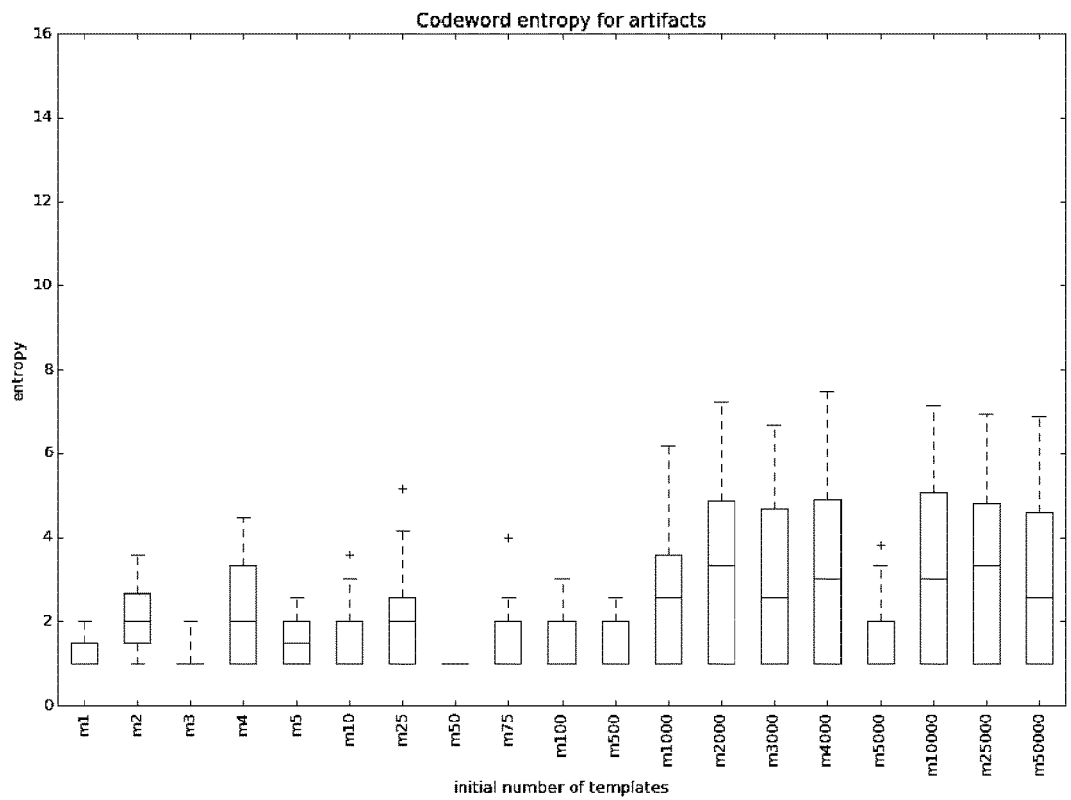
Figure 28:
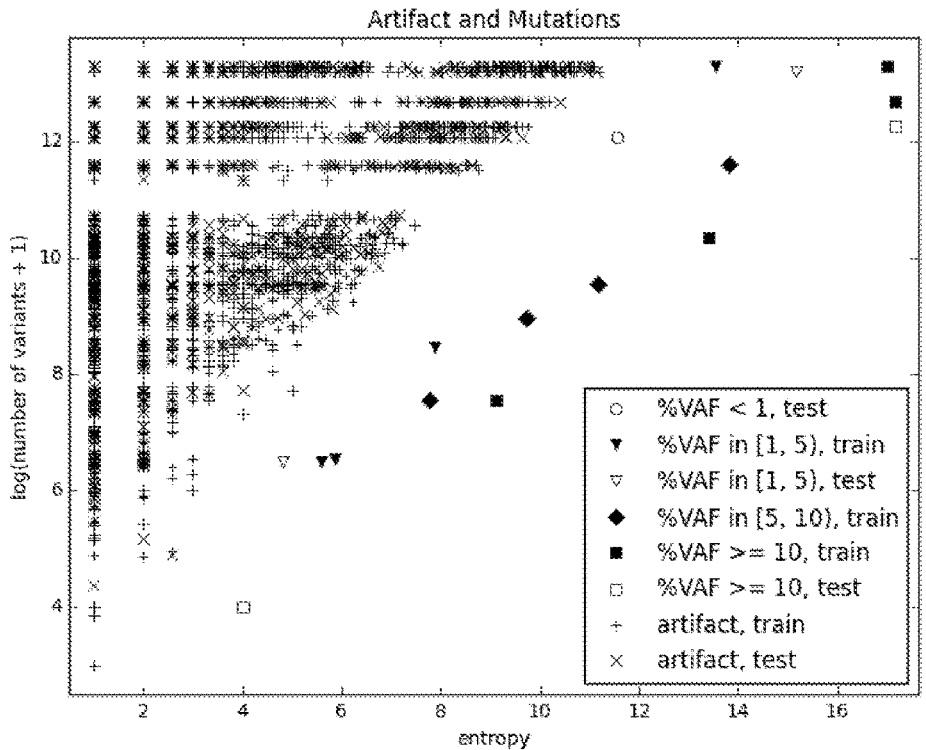

FIG. 22 is a schematic diagram showing the use of codeword entropy to assess the quality of the amplified product;

FIG. 23A is a graph showing amplicon performance with and without codewords, m=5000;

FIG. 23B is a graph showing amplicon performance with and without codewords, m=10000;

FIG. 24A is a graph showing entropy as a function of the number of starting templates for 8-mers, where the entropy is calculated on all the reads that contain a given allele in the chromosome 5 at position 136633338;

FIG. 24B is a graph showing entropy as a function of the number of starting templates for 10-mers, where the entropy is calculated on all the reads that contain a given allele in the chromosome 5 at position 136633338;

FIG. 25 is a graph showing the distribution of codeword entropy for several numbers of starting templates, where the entropy was calculated on all codewords from reads that belong to the same amplicon;

FIG. 26 is a graph showing the codeword entropy for minor SNP alleles as a function of the initial number of templates;

FIG. 27 is a graph showing the codeword entropy of artifact alleles as a function of the initial number of templates; and FIG. 28 is a graph showing the entropy of variants of artifact and true mutations, where the training and testing data and the % VAF of all true mutations is indicated in the labels.

DETAILED DESCRIPTION

The present disclosure provides, in part, methods for determining relevant sequence parameters of a balanced performance codeword pool and utilizing the measured parameters for the design of larger balanced pools, ab initio.

Molecular counting pools of nucleic acid codewords (such as DNA or RNA) can be useful to provide estimates of starting template number, quality and detection/avoidance of PCR/sequencing/DNA synthesis errors. The counting of randomly introduced nucleic acid codewords may be analysed using measures of entropy and related information theoretic measures to, for example, determine template number and control for errors.

In one aspect, the present disclosure provides methods for the design and selection of a suitable codeword pool for random attachment to a target sequence or template, such as a nucleic acid template. By "nucleic acid template" or "target sequence" is meant a DNA, RNA, or DNA/RNA hybrid molecule, or complementary molecule. The nucleic acid template or target sequence may be isolated from a specimen including, without limitation, a clinical specimen, a biological research specimen, or a forensic specimen, or may be an artificial sequence, such as a synthetic or recombinant sequence. In some embodiments, a nucleic acid template or target sequence includes, without limitation, a sequence that is of clinical or biological interest, such as somatic mutation hotspots in patient solid tumor or circulating cell-free DNA specimens, or a sequence of forensic interest. In some embodiments, a nucleic acid template or target sequence includes, without limitation, a sequence containing a mutation (a "true sequence variant"). The true sequence variant may include a low prevalence true mutation, such as a mutation having a variant allele frequency (VAF) of less than 1%, 2%, 3%, 4%, 5%, 6%, 7%, 8%, 9%, or 10%. In some embodiments, the low prevalence true mutation may have a VAF of less than 5%.

By "complementary" is meant that two nucleic acids, e.g., DNA or RNA, contain a sufficient number of nucleotides which are capable of forming Watson-Crick base pairs to produce a region of double-strandedness between the two nucleic acids. Thus, adenine in one strand of DNA or RNA pairs with thymine in an opposing complementary DNA strand or with uracil in an opposing complementary RNA strand. It will be understood that each nucleotide in a nucleic acid molecule need not form a matched Watson-Crick base pair with a nucleotide in an opposing complementary strand to form a duplex. A nucleic acid template or target sequence can be of any length or nucleotide composition such as any chain of two or more covalently bonded nucleotides, including naturally occurring or non-naturally occurring nucleotides, or nucleotide analogs or derivatives.

A pool of randomly generated codewords can be sufficient for entropy estimation, but a randomly generated set of codewords may contain nucleic acid sequences which perform poorly in PCR sequencing reactions, thus diminishing or biasing the information content used to count template molecules. Accordingly, in some embodiments, measuring entropy differences between amplified starting templates can be useful for optimal performance.

In one aspect, the present disclosure provides a method for obtaining a balanced pool of codewords.

By "codeword" is meant a linear polymeric molecule having a sequence that can be uniquely determined, such as, without limitation, a DNA, RNA, DNA/RNA hybrid or other macromolecule capable of being amplified. While the methods exemplified herein refer to DNA molecules, it is to be understood that the methods are generally applicable to other molecules that are capable of being amplified.

A codeword can be of length "k." The length k can be any defined length, such as at least 4, 5, 6, 7, 8, 9, 10, 11, 12, 13, 14, 15, 16, 17, 18, 19, 20, 21 units (e.g., nucleotide bases or amino acid residues) or longer, although increasingly greater lengths may lead to increased costs and loss of efficiency. In some embodiments, the length k can be 10.

By a "balanced pool" of codewords is meant a pool of codewords that allows for balanced thermodynamic design to avoid biased amplification or incorporation of codewords and/or is sufficiently distinct so as to tolerate sequencing errors in the determination of codeword identity. A suitable balanced pool of codewords may be in the order of $|W| \approx m^* (2^c - 2)$ codewords (where m is the initial number of templates and c the number of PCR cycles), to allow for estimation of entropy as for example described herein. In general, and without being bound to any particular theory, a balanced pool of codewords provides even performance and may be able to differentiate cases of similar amplification performance.

In some embodiments, an initial sample of a plurality of codewords having a defined length k is provided. The initial sample of codewords can represent all combinations of a sequence or a subset thereof, for example, more than 10, or more than 100 distinct codewords although, it is to be understood that the size of the pool will limit the possible combinations. In some embodiments, the initial sample of codewords may be the same size as that of the pool being tested. The generation of codeword sequence combinations of length k can be done using any suitable technique, such as by incorporation of random bases, specified by the inclusion of a series of Ns (i.e., A, G, C, T or U) in the codeword sequence, or by combinatorial explicit specification of all codeword subsequences of length k, provided to the oligonucleotide synthesiser, or by a combination of thereof. Such techniques are familiar to those skilled in the art. In some embodiments, modified bases incorporating, for example, thio or other base modifications can be used. Without being bound to any particular theory, modified bases may alter the thermodynamic properties of codewords, or may provide a method of retrieving codewords by physical methods, for example incorporation of a biotin moiety, for biotin-streptavidin capture.

Sequence Feature Parameters Relevant to Codeword Performance

In some embodiments, one or more of the following combinatorial and/or thermodynamic constraints can be applied to codewords.

In the methods described herein, W is the set of codewords w defined as linear sequences of nucleotide bases of length k. That is $W = \{w = w_1 w_2 \ldots w_k | w_i \in \{A, G, C, T\} \forall i \in 1 \ldots, k\}$.

In physical reality, each barcode DNA sequence or codeword can include multiple identical molecules encoding the sequence. A multiset of codeword molecules in a physical pool of oligonucleotides can therefore be defined as $M = \{w : i | w \in W \text{ and } i = 1, 2, \ldots\}$, where w are the root elements and $i = i(w)$ is the multiplicity of w. That is, the multiplicity of w is the number of instances of w observed in the multiset M. The cardinality of the root set (unique codewords) is $|W| = p$, whereas the cardinality of the multiset M is $\Sigma_{w \in W} i(w)$.

The design of high quality pools M can be modeled by introducing combinatorial and thermodynamic constraints. High quality codewords do not decrease the number of amplified DNA template sequences. One or more of the following combinatorial constraints can be imposed on the root elements w where H is the Hamming distance of a codeword pair $(w_i, w_j)$ defined as the number of mismatches in a perfect alignment of two codewords of the same length $w_i$ and $w_j$.

C1: codeword mismatches (HD_w). $H(w_i, w_j) \geq d_w$ with $w_i, w_j \in W$. Enforces a high number of mismatches between all possible pairs of codewords in the pool.

C2: codeword genome mismatches (HD_g). $H(w_i, w_g) \geq d_g$ with $w_i \in W$ and k-mer $w_g$ found in the human genome. To avoid that codewords interact with human k-mers during the PCR process, $d_g$ mismatches between each codeword and all human k-mers are introduced in the model.

C3: tagged primer genome mismatches (HD_gp). All k-mer subsequence $w_s$ of $w_{ip}$ defined as $w_{ip}$ joined with primer p shall have $H(w_s, w_{ip}) \geq d_p$ with $w_{ip} \in W$. This constraint ensures that codeword boundaries with container primer sequence does not generate inadvertent homology in the genome.

C4: tagged primer pair mismatches (HD_pp). $H(w_{ip(i)}, w_{jp(j)}) \geq d_{pp} \forall w_{ip(i)}, w_{jp(j)}$ codeword tagged primers. This constraint ensures that codeword tagged primers do not interact with each other.

C5. GC content. Each $w_1 \in W$ has GC content c such that $45 \leq c \leq 60$. The stability and uniformity of the codewords can be modeled by counting specific bases G and C within the same codeword.

One or more of the following thermodynamic constraints can also be imposed to prevent undesired interactions.

T1. Hairpin melting temperature. For each codeword joined with a primer $w_{ip}$, the highest melting temperature from all possible hairpins that can potentially form with the sequence $w_{ip}$ must be lower than temp_hairpin. The formation of hairpins will prevent the annealing of the barcode tagged primers to the DNA template during PCR.

T2. Self Dimer free energy. The free energy $\Delta G(w_{ip})$ of the secondary structure of every codeword joined to a primer $w_{ip}$ must be larger than a threshold $\Delta G_{dimer}$. This constraint forbids the formation of a secondary structure of $w_{ip}$ that prevents annealing of the barcode tagged primers to the DNA template.

T3. Heterodimer free energy. The free energy $\Delta G(w_{ip(i)}, w_{jp(j)})$ of the heterodimer formed by the interaction of two barcode tagged primers $w_{ip(i)}$ and $w_{jp(j)}$ must be larger than a threshold $\Delta G_{heterodimer}$ for all $w_{ip(i)}$ and $w_{jp(j)}$. This constraint forbids the formation of a secondary structure between pairs of barcode tagged primers that prevents annealing to the DNA template.

For a defined codeword length, the size of the root set W decreases with the number of constraints. However, the number of required unique codewords increases with the number of PCR cycles and with the mass of DNA target templates. For instance, the absolute number of template molecules in a reaction can be estimated using the mass of a haploid human genome to be approximately 3.4 pg (i.e. $3 \times 10^{-12}$ g). A typical targeted PCR sequencing reaction will use between 1 ng and 10 ng of template molecule mass, i.e. between ~300 and ~3000 copies per haploid target locus, or twice that number i.e. between ~600 to ~6000 copies per diploid locus. However, the methods described herein allow for determining entropy down to single template molecules. For four PCR cycles, between 300*14 and 3000*14 codewords are needed for each end of one target locus, when incorporating the design constraints C1-05 and T1-T3 disclosed above. However, the pools are designed such that each target locus and each end has a different set of codewords. That is, $M_{L1_R} \Omega M_{L1_F} \cap \ldots \cap M_{Ln_R} \Omega M_{Ln_F} = \emptyset$, where $Li_R$ and $Li_F$ are the target locus Li for the reverse and forward ends. Accordingly, in an experiment with x target locus, the number of different codewords required is between $300*14*2*c=8,400*c$ and $3000*14*2*c=84,000*c$.

Therefore, large and diverse set of codewords are useful. Longer and shorter codeword lengths can be used, depending on the desired constraints as indicated in C1-5 and T1-3. However, the constraints imposed to the codewords should be the minimum required to avoid undesirable interactions and at the same time to ensure that the number of unique codewords is large enough to obtain a high codeword entropy in four or more PCR cycles.

Measurement of Codeword Performance Parameters Over a Sub-Sample of Codewords

In some embodiments, an exhaustive method can be used to physically test all codewords of a fixed length and select the codewords that produce optimal PCR amplification in various applications, in order to determine the codeword properties (e.g., one or more of C1-5 and/or T1-3) that have a higher influence on amplification efficiency.

In alternative embodiments, for codewords of, for example, 4 to 21 bases in length, such as 4, 5, 6, 7, 8, 9, 10, 11, 12, 13, 14, 15, 16, 17, 18, 19, 20, or 21, a method for reducing the feature selection space can be used. The Lasso (Least Absolute Selection and Shrinkage Operator) method for feature selection is used to determine features that produce similar codeword performance. This method fits a linear model by penalizing the L1 norm ($\|\beta\|_1 = \Sigma_{j=1}^P |\beta_j|$) of weights found by the regression. The coefficients are estimated as $$\hat{\beta}_{lasso} = \mathrm{argmin}_\beta(\|y - X\beta\|^2 + \lambda \Sigma_{j=1}^P |\beta_j|)$$

where $y_i$ is the response variable or codeword performance, $X_j$ are the explanatory variables or features, and $\lambda$ is the weight assigned to each codeword property $\beta_j$. The tuning parameter $\lambda$ controls the strength of the penalty. That is, $\hat{\beta}_{lasso}$ is the linear regression estimate when $\lambda=0$ and $\hat{\beta}_{lasso}=0$ when $\lambda \rightarrow \square$. Cross validation can be used to select the best value of $\lambda$.

It is to be understood that any other feature selection method, or a classification method such as AdaBoost, can be used to determine the codeword properties that have a larger influence on amplification efficiency.

In one example, the initial sample of codewords representing all possible combinations of sequence or a subset thereof of a defined length k is generated. In some embodiments, the initial sample of codewords includes at least 10 distinct codewords. In alternative embodiments, the initial sample of codewords includes more than 100 distinct codewords. In some embodiments, if the full set of codewords of length k, is measured, this can be regarded as a subset of codewords length k+1, k+2, etc. In some embodiments, where k is 10, all possible sequence combinations of codewords can be generated. In general, the initial sample of codewords should be proportionate to the length k, in order to obtain a representative set of codewords.

Each distinct codeword in the initial sample of codewords may be attached to the 5' end of a single target sequence primer or primer pair, to form a codeword-primer molecule. By "primer pair" is meant two optimally designed oligonucleotide sequences (a "first primer" and a "second primer") such as forward and reverse primers, which can serve to prime the polymerase chain reaction, where the first primer and the second primer anneal to complementary sequences on either strand of the target sequence. A primer in a primer pair can be of any suitable length, such as at least 8, 9, 10, 11, 12, 13, 14, 15, 16, 17, 18, 19, 20, 21, 22, 23, 24, 25 nucleotide bases or longer, although increasingly greater lengths may lead to increased costs, errors in synthesis, or loss of efficiency. In some embodiments, a primer in a primer pair can be 15 nucleotide bases. In some embodiments, the same codeword can be attached to the first primer and the second primer in a primer pair. In alternate embodiments, different codewords can be attached to the first primer and the second primer in a primer pair. In some embodiments, a codeword can be attached to only one primer of a primer pair. In alternate embodiments, a codeword can be attached to both primers of a primer pair.

A codeword can be attached to a primer using any suitable technique, such as oligonucleotide synthesis or ligation or other suitable method. For example, the initial sample of all possible codewords of length k, is synthesized at the 5' end of a single target sequence primer (such as locus primer pairs as disclosed in the CG001v2 panel sequence described herein, see Table 15). In some embodiments, an adapter sequence, for library construction of the PCR products, can be added as part of the synthesis, 5' to the codeword, as outlined in for example FIG. 5 and in the CG001v2 assay described herein. An adapter sequence may be a nucleic acid sequence, such as a DNA sequence, specifically designed for enabling sequencing chemistry reactions on NGS platforms, where sequencing library molecules are tethered to a glass flow cell surface or beads and subjected to successive cycles of nucleotide base identification from either end of the molecules. Adapter sequences are known in the art and many such sequences are commercially available.

A target sequence, including a sequence complementary to the sequence of each of the target sequence primer pairs, can be amplified using the codeword-primer molecule pairs by any suitable amplification reaction, for example, polymerase chain reaction (PCR) or any suitable linear amplification technique using any polymerase that can amplify chains of nucleic acids, applied sequentially, such as without limitation T4 polymerase, phi29 polymerase, or reverse transcriptases (in the case of RNA) to provide an amplification reaction product including the codeword sequence(s).

The sequence of the amplification reaction product may be obtained using any suitable techniques including, without limitation, next-generation DNA sequencing chemistries utilizing sequencing-by-synthesis on glass flow cells, pyrosequencing on beads, or proton semiconductor technology, coupled with nucleotide base readouts as optical signals or ion pH changes. Additional techniques undergoing adoption include true single-molecule real-time sequencing utilizing nanowells and nanopores.

In some embodiments, the amplification performance of the codewords can be determined as follows. The PCR target reaction may be performed using, for example, the process described for the CG001v2 assay as described herein, however the reaction may be stopped after a predetermined number of amplification cycles (a defined number of cycles), to determine the rate of increase in abundance of codewords. Thus, samples of the codeword-target PCR reaction may be taken at 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or greater cycles, or at any combination of a subset of these cycles (an intermediate number of cycles). In some embodiments, additional amplification cycles may be performed using nested PCR techniques. In some embodiments, the limit c* may be determined by the number of cycles of a PCR reaction although the expected number of codewords required for c* cycles should be at most the size of the codeword pool.

The PCR reaction at the end of each cycle, at the end of the defined number of cycles, or at an intermediate number of cycles, may then be indexed and sequenced on any next-generation sequencing (NGS) device or any device capable of providing a digital count of nucleic acid template sequences, for example as described in the CG001v2 assay or by any familiar PCR-NGS sequencing method known to a person skilled in the art.

Figures 2, 3:
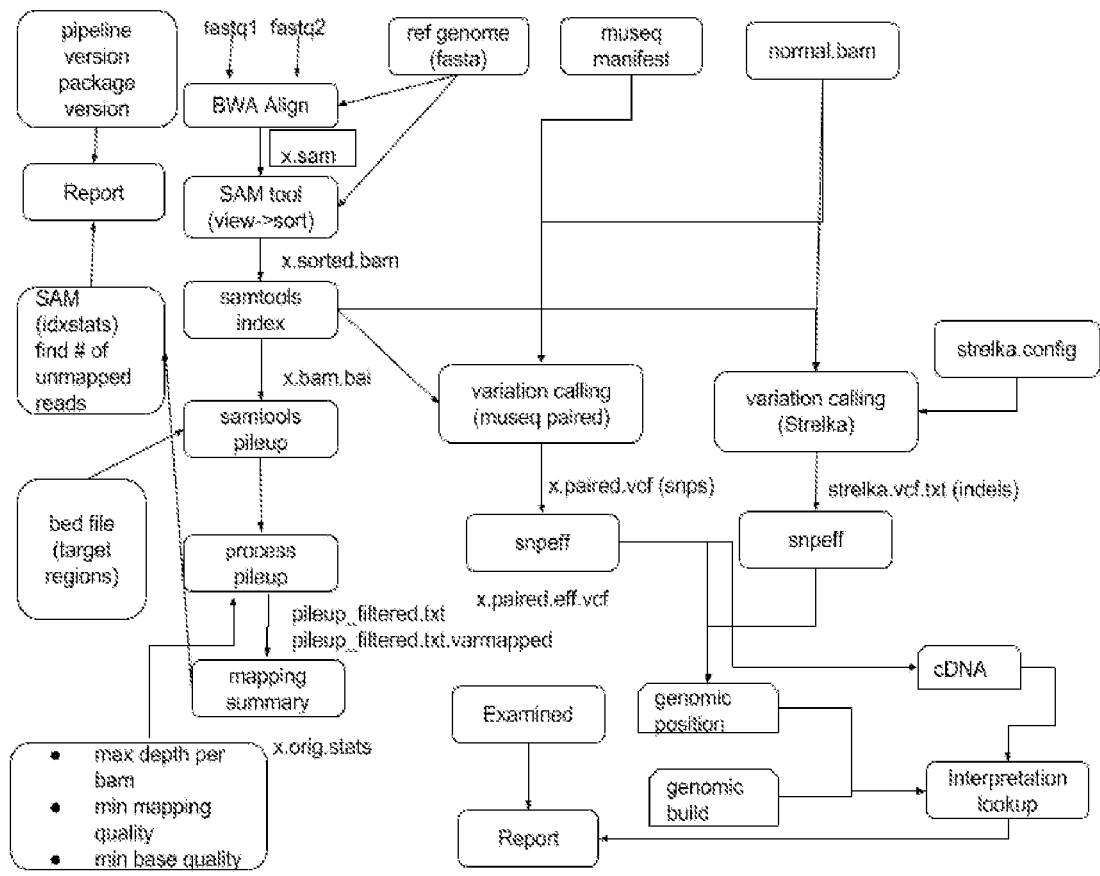
FIG. 2 is a flow chart showing sequence analysis workflow.
FIG. 3 is a matrix showing codeword performance as a function of subsequence composition and location.

The abundance of codewords present in the amplification reaction product at the end of each cycle may then be determined by, for example, DNA sequence alignment and counting of codeword instances, for example, as in the CG001v2 assay outline (FIG. 2). Codewords may be extracted using different strategies. For example, by matching a set of primers against amplicon sequencing data and trimming k-mers that occur between the primer and the 5' end. This utility supports setting a Hamming distance threshold when matching the primer sequence. In order to obtain high quality data, both mated reads must pass the filter to be considered. Furthermore, low quality reads such as primer-dimers may be filtered out by using an additional metric, such as the edit distance calculated as the number of complementary bases of the pairwise sequence alignment of the mated reads. Codewords from reads with edit distance larger than a threshold to the mode edit distance of all the reads in the amplicon may be filtered out. This reveals the number of codewords of length k, represented in each of the PCR cycles from 4 to 35.

The performance of codeword sequences may then be calculated by (i) the relationship between the observed and expected codeword abundance over 1 or more iterations of this method and/or (ii) the rate of increase in abundance over increasing PCR cycles. A different approach may be to (iii) analyze the observed distribution of codeword frequencies.

For (i), the z-score value of the observed entropy may be computed using the parameters of the expected entropy distribution under the assumption that it follows a Normal distribution, to give the probability of the observed entropy under the expected entropy distribution. Other statistical approaches for comparing the observed entropy to the expected entropy distribution may be used, as will be familiar to a person skilled in the art.

Figure 6:
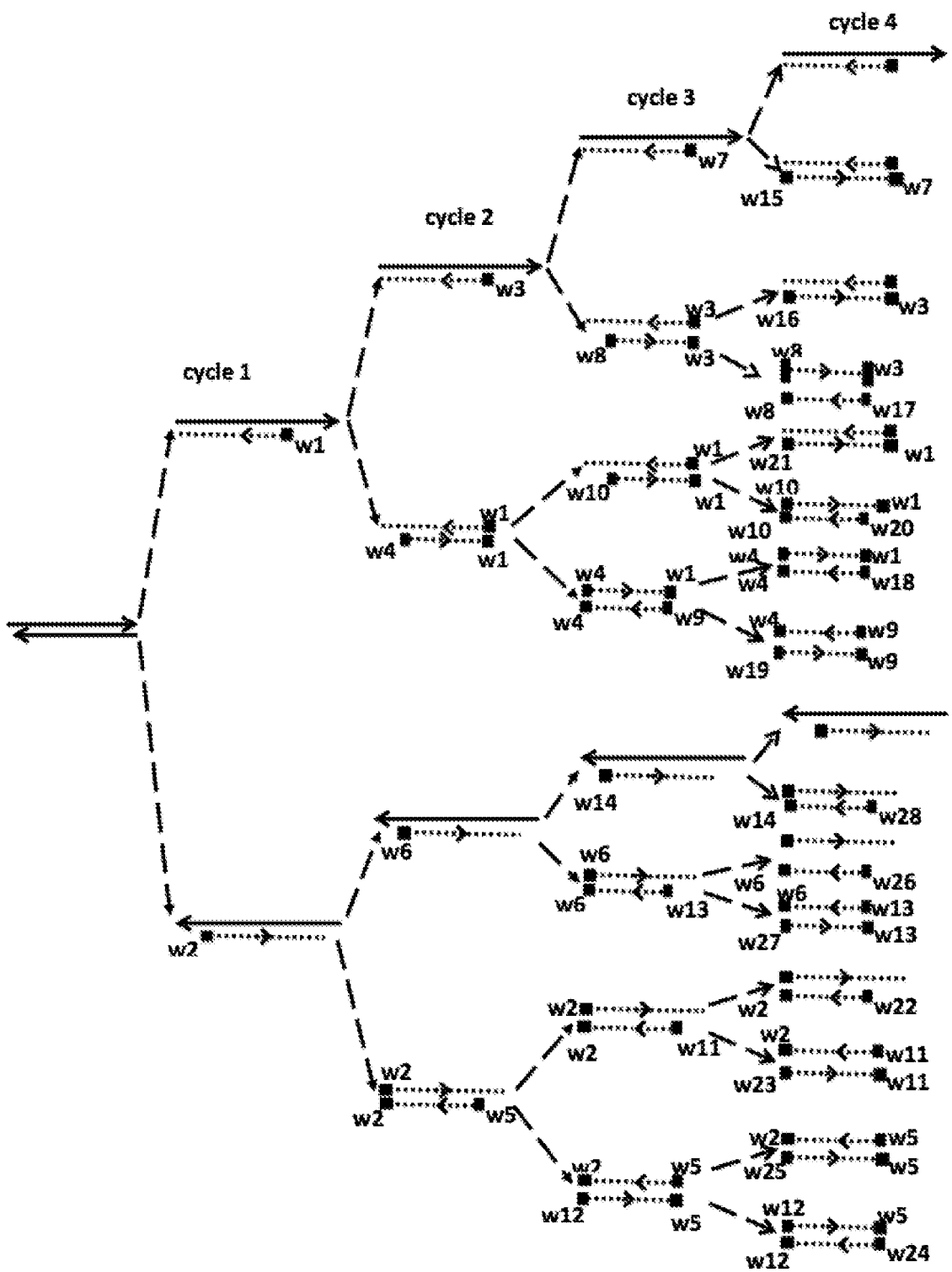
FIG. 6 is a schematic diagram of amplified sequences and codewords observed in the first four PCR cycles of an exemplary sequencing reaction. This diagram shows all the codewords that are incorporated in the first three PCR cycles. However, only codewords from amplified sequences are shown in the 4th PCR cycle.

The codeword amplification coefficient for (ii) may be calculated directly, or by linear modeling where, for example, the abundance of a given word $Y_w$ is modeled as function of $\beta_0 + \beta_1 * X$ where X is the number of PCR cycles and the estimate of $\beta_1$ the coefficient of amplification. The value of $\beta_0$ is related to the cycle in which codeword w was observed for the first time. Sequence amplification in PCR is exponential but codeword amplification is linear (FIG. 6 and Table 1).

TABLE 1

Codeword frequency per PCR cycle.

| cycle | codeword frequency $f_{j,c}$ |
|---|---|
| 1 | |
| 2 | $f_{1,2} = f_{2,2} = f_{4,2} = f_{5,2} = 1$ |
| 3 | $f_{1,3} = f_{2,3} = f_{4,3} = f_{5,3} = 2$ |
| 4 | $f_{1,4} = f_{2,4} = f_{4,4} = f_{5,4} = 3$ |

Accordingly, in a perfect PCR reaction, $Y_w = \beta_0 + X$ as codewords are expected to increase by one per PCR cycle.

For (iii), the observed codeword frequency distribution may be used to identify codewords with poor amplification performance or codewords that are preferentially amplified. The observed frequency values should be within a range [a, b] where the number of codewords with frequency i is expected to be equal or higher than the number of codewords with frequency j for $a \leq i < j \leq b$ since codeword amplification is linear and more codewords are introduced in later cycles of the PCR reaction. An example of over-amplification is when there are no codewords with frequencies in the range [k, b−1] where $a < k < b$ but a codeword is observed with frequency b much higher than the rest of the observed frequencies. That is, $k \ll b$. In this approach, only a small sample of the entire population of reads that contain a given codeword can be observed, since only a portion of the billions of amplified reads are sequenced in an assay.

Iterative Procedure to Refine Performance Measures

Figure 4:
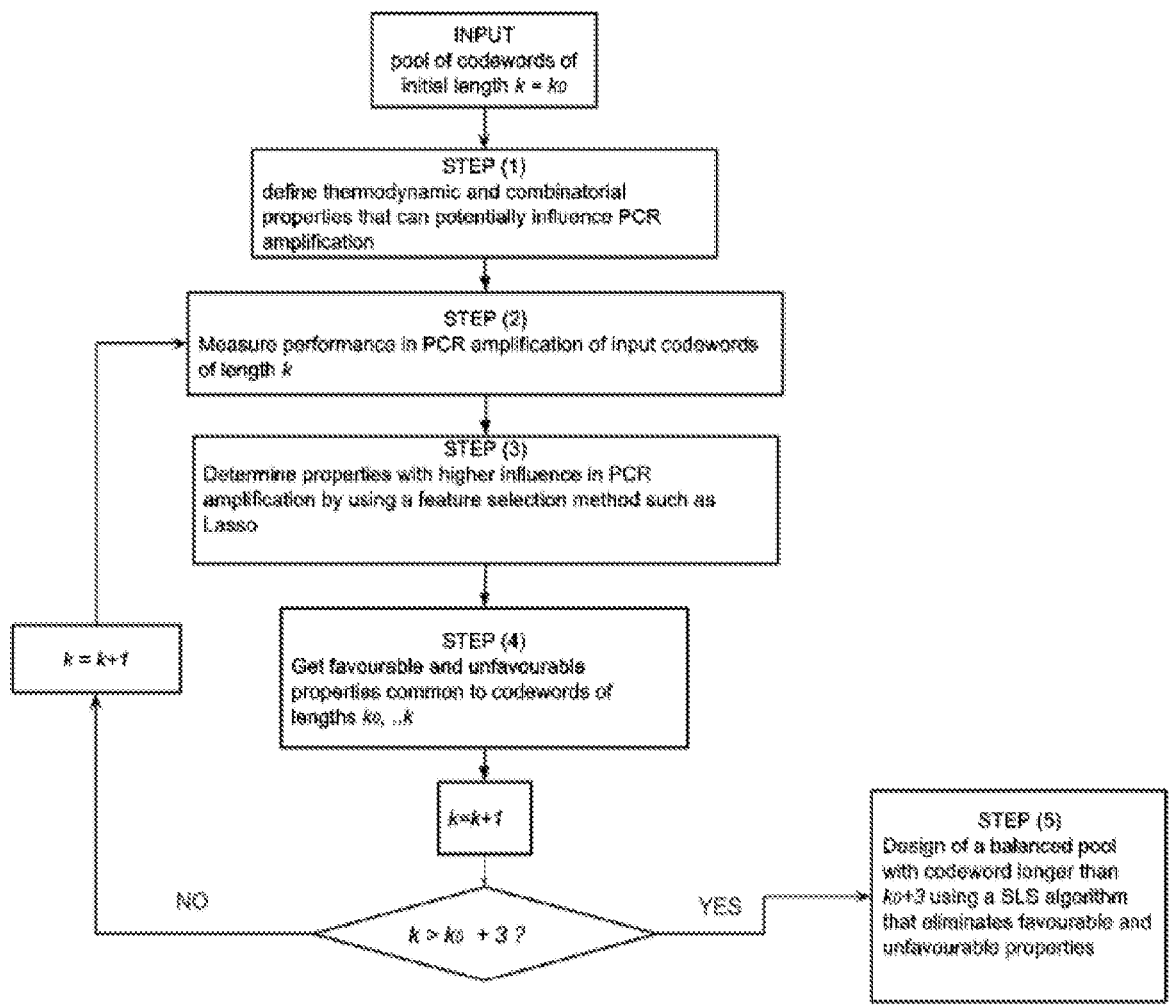
FIG. 4 is an algorithm to determine parameters with high influence in codeword performance.

In the above example, favourable and unfavorable codeword properties are determined for codewords of a defined length. In some embodiments, codewords of shorter or longer lengths (e.g., one, two, three, four or more consecutive codeword lengths) may be generated to provide additional measures of performance, and the amplification and analysis steps may be repeated using the codewords of different lengths. FIG. 4 shows the iterative procedure to investigate the thermodynamic and sequence parameters that have a higher influence in PCR amplification.

In some embodiments, the amplification and analysis steps may be performed on a single target locus. In alternative embodiments, the amplification and analysis steps may be performed on 2 or more loci to assess the independence of target locus specific sequences, from the performance of codeword-primer molecules attached to individual target locus sequences.

In some embodiments, the entire process (generation of codewords, amplification and analysis) may be conducted once for each codeword length and/or target locus. In alternative embodiments, the entire process (generation of codewords, amplification and analysis) may be repeated two or more times for each codeword length and/or target locus. In some embodiments, the variance between repeated measurements may be determined and repeated measurement discontinued when the variance is below a desired value such as 1%, 5%, 10%, 15%, 20%, 25%, etc. It is to be understood that a skilled person would readily recognize the point at which measurements are stabilizing around any particular value and discontinue further repeats after that point.

Measurement of Codeword Performance as a Function of Sequence Composition

Having measured the performance of codewords of defined length, at a defined target locus, the sequence parameters associated with performance may be determined as follows.

In some embodiments, codeword performance may be categorised as a function of subsequence composition and location. Information relating to favourable and unfavourable subsequence composition and location may be used to design longer codewords that may be more likely to exhibit good PCR amplification.

In some embodiments, subsequences in codewords that influence PCR amplification may be detected as follows.

Let $W^k$ be the set of codewords of length k. That is, $W^k=\{w=w_1w_2 \ldots w_k | w_i \in \{A,G,C,T\} \forall i \in 1 \ldots, k\}$ where the size of $W^k$ is $|W^k|=4^k$. The performance $y_j$ of each codeword or a subset of codewords $w_j \in W^k$ is measured in PCR reactions. A matrix is then generated with subsequence composition in the rows and subsequence location in the columns. The elements of the matrix are the median performance of codewords with specific subsequence composition and location. For instance, in matrix Y shown in FIG. 3, the first row corresponds to codewords with subsequence AA, and the first column to homopolymers found in the first and second position of the codeword. Therefore $y_{11}$ is the median amplification of all codewords $w=AAw_3 \ldots w_k$ with $w_i \in \{A, G, C, T\}$ i=3 ... k.

Subsequences in the matrix have a fixed length, and therefore one matrix is generated for every possible subsequence length l=2 ... k−1. However, not all the matrices provide the same amount of information. For instance, the number of subsequences of a given length decreases with the length of the subsequence, and therefore long subsequences provide less information. Furthermore, for long codewords, subsequences of length two might not have an impact on PCR amplification. A suitable subsequence length is therefore 25% of the codeword length, that is the nearest integer to l=0.25*k.

For a fixed k, a heatmap can be generated from matrix Y to infer subsequences with poor and good performance. Furthermore, the elements of Y can also be clustered to identify subsequence compositions and locations that produce similar amplification performances.

This method is exemplified using experimental data of several samples on a commercial Normal Female DNA template with random 8-mers synthesized into both forward and reverse primers of one of the target amplicons in the cancer hotspot multiplex PCR assay described herein. Codeword primers were used both as part of a primers mix and alone, as a singleplex PCR. The input DNA was varied from m=500, 1000, 5000, 10000, 50000, and 100000 haploid genomes. Separate multiplex PCR reactions were run for 15 and 25 cycles. All experiments were performed using an Illumina Miseq platform. Table 2 shows the sorted frequencies of all possible 2-mers from codewords that are observed in every sample. The most favourable 2-mers are 'AA' whereas the least favourable are the ones with high GC content such as 'GG' or 'CG'.

TABLE 2

List of 2-mers sorted by median frequency over 24 samples with different experimental conditions.

| position | k-mer | median frequency | position | k-mer | median frequency | position | k-mer | median frequency |
|---|---|---|---|---|---|---|---|---|
| 5 | GG | 52148 | 3 | TG | 68681 | 5 | AC | 74297 |
| 6 | GC | 52221 | 5 | GT | 68698 | 3 | AC | 74731 |
| 6 | GG | 53171 | 6 | GA | 68723 | 0 | AC | 74830 |
| 4 | GG | 53391 | 2 | CT | 68743 | 1 | AC | 75247 |
| 5 | CG | 54349 | 4 | AG | 68786 | 2 | CA | 75590 |
| 5 | GC | 54760 | 5 | TG | 68848 | 4 | CA | 75842 |
| 6 | CG | 54998 | 6 | TC | 68898 | 3 | CA | 76134 |
| 3 | GG | 55248 | 5 | CT | 69051 | 6 | CA | 76547 |
| 4 | CG | 55261 | 4 | GA | 69069 | 5 | CA | 76964 |
| 4 | GC | 55681 | 0 | GA | 69155 | 0 | CA | 77807 |
| 1 | CG | 55848 | 1 | CT | 69171 | 1 | TA | 86486 |
| 3 | CG | 56038 | 1 | GA | 69333 | 3 | TA | 88307 |
| 2 | GG | 56573 | 3 | CT | 69655 | 2 | AT | 88900 |
| 0 | GG | 56604 | 6 | TG | 69784 | 0 | TA | 88926 |
| 3 | GC | 56996 | 6 | AG | 69840 | 4 | TA | 89492 |
| 1 | GG | 57196 | 1 | AG | 69853 | 0 | TT | 89688 |
| 2 | GC | 57377 | 3 | GA | 69878 | 6 | TA | 89921 |
| 2 | CG | 57532 | 4 | GT | 70031 | 2 | TA | 90440 |
| 0 | GC | 57712 | 0 | AG | 70031 | 3 | AT | 90996 |
| 2 | CC | 58992 | 2 | GA | 70128 | 5 | AT | 91077 |
| 1 | GC | 59243 | 6 | CT | 70205 | 5 | TA | 91119 |
| 0 | CG | 59338 | 2 | GT | 70218 | 0 | AT | 91234 |
| 0 | CC | 59486 | 4 | CT | 70289 | 3 | TT | 91260 |
| 3 | CC | 59696 | 3 | GT | 70348 | 2 | TT | 91315 |
| 1 | CC | 59713 | 5 | GA | 70480 | 1 | AT | 91548 |
| 4 | CC | 60959 | 2 | TG | 70552 | 4 | AT | 91584 |
| 6 | CC | 61223 | 0 | TG | 70662 | 5 | TT | 92507 |
| 5 | CC | 61962 | 1 | GT | 70863 | 4 | TT | 92524 |
| 0 | TC | 66477 | 3 | TC | 70928 | 1 | TT | 92556 |
| 1 | TC | 66654 | 1 | TG | 71399 | 6 | TT | 92730 |
| 5 | AG | 67333 | 4 | TC | 71595 | 6 | AT | 93779 |
| 0 | GT | 67514 | 2 | TC | 71831 | 2 | AA | 95089 |
| 2 | AG | 67813 | 5 | TC | 71954 | 1 | AA | 95533 |
| 3 | AG | 68205 | 2 | AC | 73323 | 0 | AA | 96293 |
| 6 | GT | 68563 | 6 | AC | 73647 | 4 | AA | 97173 |
| 4 | TG | 68648 | 1 | CA | 73773 | 3 | AA | 97315 |
| 0 | CT | 68659 | 4 | AC | 74091 | 5 | AA | 98869 |
|   |   |   |   |   |   | 6 | AA | 100166 |

Sequence and thermodynamic properties can be combined in the Lasso method to determine the most influential sequence and thermodynamic properties. This method is exemplified on a commercial Normal Female DNA template with 8-mers synthesized into both forward and reverse primers of one of the target loci of our cancer hotspot multiplex PCR assay described herein. We used data from several experiments with different PCR cycles (c=15, 10, 25, and 30) and amounts of input (m=7,575, 0, 500, 1K, 5K, 10K, 100K). All experiments were performed using an Illumina Miseq platform. The sequence properties considered are subsequence location and composition where subsequences are of length 3. The GC content is included as the thermodynamic property. A 3-fold cross validation was used to determine the optimal value for the tuning parameter A. The results for the Lasso method using this tuning parameter are listed in the Table 3. This table suggests that GC content has a higher influence on codeword performance than subsequence location and composition of 3-mers.

TABLE 3

Coefficients in the Lasso method with features as GC content and subsequence location and composition.

| Explanatory Variables | Coefficient | Explanatory Variables | Coefficient | Explanatory Variables | Coefficient | Explanatory Variables | Coefficient |
|---|---|---|---|---|---|---|---|
| GCcontent: 8 | −0.2025 | position: 2 kmer: AAG | −0.0017 | position: 3 kmer: CTC | 0 | position: 0 kmer: CGC | 0.0045 |
| GCcontent: 7 | −0.1702 | position: 1 kmer: TAT | −0.0016 | position: 3 kmer: CTG | 0 | position: 2 kmer: CAC | 0.0045 |
| GCcontent: 6 | −0.1222 | position: 4 kmer: GAC | −0.0016 | position: 3 kmer: GAA | 0 | position: 4 kmer: TAA | 0.0046 |
| GCcontent: 5 | −0.0660 | position: 3 kmer: GAC | −0.0016 | position: 3 kmer: GAT | 0 | position: 2 kmer: TAA | 0.0047 |
| position: 0 kmer: GAG | −0.0420 | position: 5 kmer: TGG | −0.0016 | position: 3 kmer: GCA | 0 | position: 2 kmer: TAT | 0.0048 |
| position: 0 kmer: TCT | −0.0348 | position: 1 kmer: ATG | −0.0015 | position: 3 kmer: GCC | 0 | position: 2 kmer: CCC | 0.0051 |
| position: 5 kmer: GGC | −0.0301 | position: 5 kmer: TGT | −0.0013 | position: 3 kmer: GCG | 0 | position: 2 kmer: GGT | 0.0058 |
| position: 1 kmer: TCT | −0.0290 | position: 4 kmer: TCT | −0.0012 | position: 3 kmer: GGG | 0 | position: 2 kmer: CAT | 0.0059 |
| position: 0 kmer: GTA | −0.0280 | position: 2 kmer: GCG | −0.0011 | position: 3 kmer: GTA | 0 | position: 1 kmer: TTA | 0.0062 |
| position: 0 kmer: GAA | −0.0271 | position: 4 kmer: CGG | −0.0011 | position: 3 kmer: GTC | 0 | position: 4 kmer: AAT | 0.0064 |
| position: 0 kmer: GGA | −0.0249 | position: 5 kmer: AGC | −0.0009 | position: 3 kmer: GTG | 0 | position: 3 kmer: TAA | 0.0067 |
| position: 5 kmer: GCG | −0.0241 | position: 5 kmer: CGT | −0.0009 | position: 3 kmer: TAC | 0 | position: 0 kmer: GCC | 0.0070 |
| position: 5 kmer: AGG | −0.0239 | position: 5 kmer: CGG | −0.0008 | position: 3 kmer: TCA | 0 | position: 4 kmer: TCC | 0.0074 |
| position: 0 kmer: AGA | −0.0231 | position: 3 kmer: CTA | −0.0007 | position: 3 kmer: TCC | 0 | position: 4 kmer: GTT | 0.0074 |
| position: 0 kmer: AGT | −0.0231 | position: 3 kmer: ACG | −0.0006 | position: 3 kmer: TCG | 0 | position: 2 kmer: GCA | 0.0076 |
| position: 0 kmer: TAG | −0.0208 | position: 5 kmer: AAG | −0.0006 | position: 3 kmer: TGC | 0 | position: 1 kmer: AGC | 0.0079 |
| position: 0 kmer: GCG | −0.0198 | position: 2 kmer: ATG | −0.0004 | position: 3 kmer: TGT | 0 | position: 1 kmer: ACC | 0.0079 |
| position: 0 kmer: AGG | −0.0190 | position: 0 kmer: TGG | −0.0004 | position: 3 kmer: TTA | 0 | position: 0 kmer: CCG | 0.0080 |
| position: 0 kmer: AAG | −0.0184 | position: 2 kmer: CTG | −0.0002 | position: 3 kmer: TTC | 0 | position: 4 kmer: TCA | 0.0084 |
| position: 0 kmer: GTC | −0.0179 | position: 2 kmer: CTT | −0.0002 | position: 4 kmer: AAG | 0 | position: 5 kmer: TTA | 0.0085 |

TABLE 3-continued

Coefficients in the Lasso method with features as GC content and subsequence location and composition.

| Explanatory Variables | Coefficient | Explanatory Variables | Coefficient | Explanatory Variables | Coefficient | Explanatory Variables | Coefficient |
|---|---|---|---|---|---|---|---|
| position: 2 kmer: AGT | −0.0177 | position: 0 kmer: ACG | 0.0000 | position: 4 kmer: ACG | 0 | position: 0 kmer: TTG | 0.0085 |
| position: 0 kmer: GAC | −0.0174 | position: 0 kmer: ACT | 0.0000 | position: 4 kmer: AGA | 0 | position: 2 kmer: CCA | 0.0085 |
| position: 0 kmer: GTG | −0.0174 | position: 0 kmer: ATA | 0.0000 | position: 4 kmer: AGC | 0 | position: 0 kmer: CCT | 0.0090 |
| position: 0 kmer: GAT | −0.0169 | position: 0 kmer: ATG | 0.0000 | position: 4 kmer: ATC | 0 | position: 3 kmer: ATA | 0.0099 |
| position: 0 kmer: TCG | −0.0165 | position: 0 kmer: CTA | 0.0000 | position: 4 kmer: ATG | 0 | position: 3 kmer: AAT | 0.0104 |
| position: 1 kmer: TTC | −0.0152 | position: 0 kmer: CTG | 0.0000 | position: 4 kmer: CAG | 0 | position: 5 kmer: GCA | 0.0104 |
| position: 3 kmer: AGT | −0.0151 | position: 0 kmer: CTT | 0.0000 | position: 4 kmer: CCG | 0 | position: 4 kmer: ATA | 0.0105 |
| position: 2 kmer: AGA | −0.0150 | position: 0 kmer: GCA | 0.0000 | position: 4 kmer: CGA | 0 | position: 3 kmer: CAA | 0.0105 |
| position: 4 kmer: GGC | −0.0149 | position: 0 kmer: GTT | 0.0000 | position: 4 kmer: CGC | 0 | position: 1 kmer: GCA | 0.0107 |
| position: 5 kmer: GGA | −0.0147 | position: 0 kmer: TAC | 0.0000 | position: 4 kmer: CGT | 0 | position: 2 kmer: ACC | 0.0107 |
| position: 3 kmer: AGA | −0.0141 | position: 0 kmer: TAT | 0.0000 | position: 4 kmer: CTA | 0 | position: 5 kmer: GCC | 0.0111 |
| position: 5 kmer: AGT | −0.0138 | position: 0 kmer: TGC | 0.0000 | position: 4 kmer: CTC | 0 | position: 3 kmer: ACC | 0.0114 |
| position: 0 kmer: GGT | −0.0134 | position: 0 kmer: TTA | 0.0000 | position: 4 kmer: CTT | 0 | position: 4 kmer: TTA | 0.0116 |
| position: 4 kmer: TAG | −0.0130 | position: 1 kmer: ACG | 0.0000 | position: 4 kmer: GCA | 0 | position: 0 kmer: CAG | 0.0119 |
| position: 0 kmer: CTC | −0.0130 | position: 1 kmer: ATC | 0.0000 | position: 4 kmer: GCC | 0 | position: 4 kmer: ATT | 0.0119 |
| position: 4 kmer: AGT | −0.0119 | position: 1 kmer: CAC | 0.0000 | position: 4 kmer: GGA | 0 | position: 5 kmer: TAC | 0.0124 |
| position: 3 kmer: TAG | −0.0119 | position: 1 kmer: CAG | 0.0000 | position: 4 kmer: GGG | 0 | position: 1 kmer: GCC | 0.0127 |
| position: 5 kmer: ACT | −0.0118 | position: 1 kmer: CAT | 0.0000 | position: 4 kmer: GGT | 0 | position: 0 kmer: AAT | 0.0130 |
| position: 5 kmer: GAG | −0.0118 | position: 1 kmer: CCC | 0.0000 | position: 4 kmer: GTA | 0 | position: 2 kmer: GTT | 0.0138 |
| position: 1 kmer: TAG | −0.0114 | position: 1 kmer: CCG | 0.0000 | position: 4 kmer: GTC | 0 | position: 4 kmer: CAC | 0.0138 |
| position: 4 kmer: GCG | −0.0114 | position: 1 kmer: CCT | 0.0000 | position: 4 kmer: TAC | 0 | position: 1 kmer: CCA | 0.0141 |
| position: 2 kmer: AGG | −0.0109 | position: 1 kmer: CGA | 0.0000 | position: 4 kmer: TAT | 0 | position: 2 kmer: TCA | 0.0141 |
| position: 4 kmer: TGG | −0.0109 | position: 1 kmer: CGC | 0.0000 | position: 4 kmer: TGA | 0 | position: 5 kmer: TCC | 0.0143 |
| position: 5 kmer: TAG | −0.0104 | position: 1 kmer: CGG | 0.0000 | position: 4 kmer: TGC | 0 | position: 5 kmer: ATT | 0.0146 |
| position: 4 kmer: AGG | −0.0104 | position: 1 kmer: CGT | 0.0000 | position: 4 kmer: TGT | 0 | position: 5 kmer: CAT | 0.0149 |

TABLE 3-continued

Coefficients in the Lasso method with features as GC content and subsequence location and composition.

| Explanatory Variables | Coefficient | Explanatory Variables | Coefficient | Explanatory Variables | Coefficient | Explanatory Variables | Coefficient |
|---|---|---|---|---|---|---|---|
| position: 0 kmer: TCA | −0.0104 | position: 1 kmer: CTA | 0.0000 | position: 4 kmer: TTC | 0 | position: 1 kmer: ACA | 0.0153 |
| position: 2 kmer: ACT | −0.0103 | position: 1 kmer: CTC | 0.0000 | position: 4 kmer: TTG | 0 | position: 5 kmer: GAA | 0.0154 |
| position: 4 kmer: GCT | −0.0102 | position: 1 kmer: CTG | 0.0000 | position: 5 kmer: ACG | 0 | position: 5 kmer: CAC | 0.0154 |
| position: 5 kmer: GTC | −0.0099 | position: 1 kmer: CTT | 0.0000 | position: 5 kmer: AGA | 0 | position: 1 kmer: AAC | 0.0156 |
| position: 2 kmer: TAG | −0.0099 | position: 1 kmer: GAC | 0.0000 | position: 5 kmer: ATC | 0 | position: 0 kmer: ATT | 0.0159 |
| position: 0 kmer: GCT | −0.0093 | position: 1 kmer: GAT | 0.0000 | position: 5 kmer: ATG | 0 | position: 2 kmer: AAC | 0.0159 |
| position: 3 kmer: AGG | −0.0092 | position: 1 kmer: GCG | 0.0000 | position: 5 kmer: CAG | 0 | position: 5 kmer: ATA | 0.0166 |
| position: 5 kmer: TCT | −0.0091 | position: 1 kmer: GCT | 0.0000 | position: 5 kmer: CCT | 0 | position: 1 kmer: CAA | 0.0169 |
| position: 5 kmer: GCT | −0.0086 | position: 1 kmer: GGC | 0.0000 | position: 5 kmer: CGA | 0 | position: 2 kmer: CAA | 0.0176 |
| position: 1 kmer: AAG | −0.0082 | position: 1 kmer: GGG | 0.0000 | position: 5 kmer: CTA | 0 | position: 4 kmer: CAT | 0.0182 |
| position: 0 kmer: TCC | −0.0081 | position: 1 kmer: GGT | 0.0000 | position: 5 kmer: CTT | 0 | position: 3 kmer: ACA | 0.0183 |
| position: 1 kmer: GGA | −0.0080 | position: 1 kmer: GTA | 0.0000 | position: 5 kmer: GAC | 0 | position: 4 kmer: CCC | 0.0184 |
| position: 0 kmer: TTC | −0.0079 | position: 1 kmer: GTT | 0.0000 | position: 5 kmer: GAT | 0 | position: 0 kmer: CGT | 0.0185 |
| position: 4 kmer: ACT | −0.0079 | position: 1 kmer: TAC | 0.0000 | position: 5 kmer: GGG | 0 | position: 3 kmer: AAC | 0.0187 |
| position: 4 kmer: GTG | −0.0077 | position: 1 kmer: TCA | 0.0000 | position: 5 kmer: GTA | 0 | position: 4 kmer: AAC | 0.0189 |
| position: 2 kmer: GAG | −0.0077 | position: 1 kmer: TCG | 0.0000 | position: 5 kmer: GTG | 0 | position: 0 kmer: CCC | 0.0194 |
| position: 3 kmer: GGA | −0.0076 | position: 1 kmer: TGA | 0.0000 | position: 5 kmer: GTT | 0 | position: 1 kmer: TTT | 0.0195 |
| position: 3 kmer: CTT | −0.0076 | position: 1 kmer: TGC | 0.0000 | position: 5 kmer: TCG | 0 | position: 4 kmer: ACC | 0.0196 |
| position: 0 kmer: GGG | −0.0074 | position: 1 kmer: TGT | 0.0000 | position: 5 kmer: TGA | 0 | position: 4 kmer: CAA | 0.0201 |
| position: 1 kmer: GAG | −0.0072 | position: 1 kmer: TTG | 0.0000 | position: 5 kmer: TTC | 0 | position: 4 kmer: ACA | 0.0216 |
| position: 4 kmer: TCG | −0.0072 | position: 2 kmer: ACG | 0.0000 | position: 5 kmer: TTG | 0 | position: 2 kmer: ACA | 0.0226 |
| position: 3 kmer: CGA | −0.0071 | position: 2 kmer: AGC | 0.0000 | GCcontent: 4 | 0 | position: 0 kmer: ACA | 0.0230 |
| position: 2 kmer: TGA | −0.0069 | position: 2 kmer: ATA | 0.0000 | position: 1 kmer: ATT | 7.5E−06 | position: 0 kmer: ACC | 0.0231 |
| position: 4 kmer: GAG | −0.0068 | position: 2 kmer: ATC | 0.0000 | position: 2 kmer: ATT | 0.0001 | position: 2 kmer: TTT | 0.0236 |
| position: 3 kmer: TCT | −0.0066 | position: 2 kmer: CAG | 0.0000 | position: 2 kmer: CGG | 0.0003 | position: 4 kmer: CCA | 0.0238 |

TABLE 3-continued

Coefficients in the Lasso method with features as GC content and subsequence location and composition.

| Explanatory Variables | Coefficient | Explanatory Variables | Coefficient | Explanatory Variables | Coefficient | Explanatory Variables | Coefficient |
|---|---|---|---|---|---|---|---|
| position: 1 kmer: GTG | −0.0065 | position: 2 kmer: CCG | 0.0000 | position: 0 kmer: TGT | 0.0004 | position: 3 kmer: TTT | 0.0246 |
| position: 2 kmer: TCT | −0.0064 | position: 2 kmer: CCT | 0.0000 | position: 2 kmer: TTG | 0.0005 | position: 0 kmer: CCA | 0.0250 |
| position: 2 kmer: GGG | −0.0055 | position: 2 kmer: CGA | 0.0000 | position: 3 kmer: TTG | 0.0006 | position: 5 kmer: CCC | 0.0260 |
| position: 0 kmer: TGA | −0.0054 | position: 2 kmer: CGC | 0.0000 | position: 3 kmer: CCG | 0.0008 | position: 5 kmer: TTT | 0.0268 |
| position: 3 kmer: GAG | −0.0052 | position: 2 kmer: CGT | 0.0000 | position: 3 kmer: CAT | 0.0009 | position: 0 kmer: AAA | 0.0283 |
| position: 2 kmer: GGA | −0.0049 | position: 2 kmer: CTC | 0.0000 | position: 3 kmer: CCA | 0.0010 | position: 0 kmer: CAC | 0.0284 |
| position: 3 kmer: TGA | −0.0049 | position: 2 kmer: GAA | 0.0000 | position: 2 kmer: AAT | 0.0013 | position: 5 kmer: AAT | 0.0284 |
| position: 1 kmer: AGT | −0.0048 | position: 2 kmer: GAT | 0.0000 | position: 3 kmer: GGT | 0.0013 | position: 5 kmer: ACC | 0.0308 |
| position: 3 kmer: GGC | −0.0048 | position: 2 kmer: GCT | 0.0000 | position: 3 kmer: CAC | 0.0015 | position: 5 kmer: TCA | 0.0308 |
| position: 3 kmer: TGG | −0.0047 | position: 2 kmer: GGC | 0.0000 | position: 1 kmer: TGG | 0.0016 | position: 0 kmer: AAC | 0.0322 |
| position: 2 kmer: GAC | −0.0047 | position: 2 kmer: GTA | 0.0000 | position: 1 kmer: TAA | 0.0016 | position: 0 kmer: CAT | 0.0340 |
| position: 3 kmer: GCT | −0.0046 | position: 2 kmer: GTC | 0.0000 | position: 1 kmer: AAT | 0.0017 | position: 1 kmer: AAA | 0.0342 |
| position: 5 kmer: TGC | −0.0044 | position: 2 kmer: TAC | 0.0000 | position: 0 kmer: TAA | 0.0017 | position: 2 kmer: AAA | 0.0346 |
| position: 2 kmer: CTA | −0.0043 | position: 2 kmer: TCC | 0.0000 | position: 0 kmer: AGC | 0.0018 | position: 5 kmer: CCA | 0.0351 |
| position: 1 kmer: AGA | −0.0043 | position: 2 kmer: TGC | 0.0000 | position: 0 kmer: CGA | 0.0025 | position: 4 kmer: TTT | 0.0352 |
| position: 1 kmer: GAA | −0.0042 | position: 2 kmer: TGG | 0.0000 | position: 1 kmer: ATC | 0.0026 | position: 4 kmer: AAA | 0.0361 |
| position: 4 kmer: CTG | −0.0041 | position: 2 kmer: TGT | 0.0000 | position: 1 kmer: GTC | 0.0027 | position: 5 kmer: AAC | 0.0368 |
| position: 0 kmer: GGC | −0.0039 | position: 2 kmer: TTA | 0.0000 | position: 1 kmer: ATA | 0.0028 | position: 5 kmer: TAA | 0.0393 |
| position: 5 kmer: CGC | −0.0036 | position: 2 kmer: TTC | 0.0000 | position: 5 kmer: TAT | 0.0033 | position: 3 kmer: AAA | 0.0409 |
| position: 2 kmer: GTG | −0.0034 | position: 3 kmer: AAG | 0.0000 | position: 0 kmer: CGG | 0.0034 | position: 5 kmer: ACA | 0.0414 |
| position: 1 kmer: ACT | −0.0033 | position: 3 kmer: ACT | 0.0000 | position: 3 kmer: TAT | 0.0034 | position: 0 kmer: CAA | 0.0427 |
| position: 5 kmer: CTG | −0.0033 | position: 3 kmer: AGC | 0.0000 | position: 3 kmer: ATT | 0.0036 | position: 0 kmer: TTT | 0.0427 |
| position: 5 kmer: CTC | −0.0033 | position: 3 kmer: ATC | 0.0000 | position: 5 kmer: CCG | 0.0037 | position: 5 kmer: CAA | 0.0490 |
| position: 2 kmer: TCG | −0.0032 | position: 3 kmer: ATG | 0.0000 | position: 3 kmer: CCC | 0.0038 | Gccontent: 3 | 0.0812 |
| position: 5 kmer: GGT | −0.0032 | position: 3 kmer: CCT | 0.0000 | position: 4 kmer: CCT | 0.0039 | position: 5 kmer: AAA | 0.0916 |

TABLE 3-continued

Coefficients in the Lasso method with features as GC content and subsequence location and composition.

| Explanatory Variables | Coefficient | Explanatory Variables | Coefficient | Explanatory Variables | Coefficient | Explanatory Variables | Coefficient |
|---|---|---|---|---|---|---|---|
| position: 4 kmer: GAA | −0.0025 | position: 3 kmer: CGC | 0.0000 | position: 3 kmer: GTT | 0.0039 | GCcontent: 2 | 0.1857 |
| position: 4 kmer: GAT | −0.0022 | position: 3 kmer: CGG | 0.0000 | position: 3 kmer: CAG | 0.0042 | GCcontent: 1 | 0.3193 |
| position: 1 kmer: TCC | −0.0018 | position: 3 kmer: CGT | 0.0000 | position: 2 kmer: GCC | 0.0042 | GCcontent: 0 | 0.4855 |
| position: 1 kmer: AGG | −0.0017 | | | | | | |

Randomized Iterative Improvement to Search Sequence Space for Suitable Codewords Based on Design Criteria The measured or calculated parameters can be used with design constraints to design a larger optimal performance pool of DNA codewords.

In some embodiments, stochastic local search algorithms (SLS) can be used. For example, the SLS algorithm described by Tulpan et al.[10] performs a local search in a space of codeword sets of fixed size which violate the given constraints. The constraints may include the codeword properties determined as described herein as well as constraints that involve interactions with other codewords in the pool, such as codeword mismatches (C1). The search is initialized with a randomly selected set of DNA strands. Then, repeatedly a conflict, that is, a pair of codewords that violates a constraint, is selected and resolved by modifying one of the respective codewords, as follows.

Input Parameters

The list of constraint parameters C, for example:
n pool size
k word length
$d_w$ Hamming distance between word pairs in the pool
$\Delta G_{heterodimer}$ free energy threshold for heterodimer formation
c GC content The parameters of the algorithm are:
max_tries maximum number of times the pool is initialized
max_steps maximum number of iterations
nhood_size neighbourhood size Initialization An initial set of words S is randomly selected such that the GC content constraints are satisfied. A GC content of [40%, 60%] can be used to avoid codewords with high and low amplification rate. In order to improve the performance of the algorithm, the search is performed on the space of codewords that satisfy the GC content constraints. Note that the total number of codewords of length k with GC content c, where 40%<c<60% is $2^k * \Sigma_{j=[k*0.40] \ldots [k*0.6]} C(k,j)$ where C are the combinations of j positions in a codeword of length k. However, the initial set typically contains a smaller set n of codewords that satisfy the GC content constraints. The set size remains constant throughout the algorithm, and in each iteration, an attempt is made to increase the number of codewords in the set that satisfy the constraints.

Neighbourhood

In each iteration, a pair of words $w_1, w_2 \in S$ that violates a constraint is selected uniformly at random. Then a neighbourhood M of $w_1$ and $w_2$ is built, that is, $M = N(w_1) \cup N(w_2)$ where N is a hybrid randomised neighbourhood composed by a one-mutation neighbourhood and a random neighbourhood.

The one-mutation neighbourhood of a given codeword w consists of all codewords that can be obtained from w by modifying one base. For a given pair of codewords $w_1$ and $w_2$ of length k, there are 2*k one-mutation neighbours that satisfy the GC content constraints.

The random neighbourhood is built by selecting a fixed number of random codewords with length k and GC content c. Note that the number of random codewords generated is nhood_size−2*k. Random neighbourhoods help escape from a local minimum in the search space.

Selection Criteria

A word w' in the neighbourhood $M = N(w_1) \cup N(w_2)$ is selected such that the number of constraint violations in the pool $\hat{S}$ is maximally reduced. The pool $\hat{S}$ is formed by replacing $w_1$ by w' if $w' \in N(w_1)$ in the pool S, or by replacing $w_2$ by w' if $w' \in N(w_2)$. Note that the pools S and $\hat{S}$ differ in one word.

Stop Criteria

In each iteration of the algorithm, the pool S is modified by replacing one word. This process is performed a maximum of max_steps times. If the solution is not found after max_steps iterations, the pool S is initialized randomly and the process is repeated. The pool S is initialized a maximum of max_tries. The SLS stops when all the words in the pool S satisfy the constraints or when a maximum of max_tries are performed.

The pseudocode for the algorithm of FIG. 4, Step (5), is as follows:

```
Procedure StochasticLocalSearch for DNA Code Design
    input: Number of words (n), word length (k), set of constraints (C)
    output: Set S of m words that fully or partially satisfies C
    for i := 1 to max_tries do
        S := initial set of words
        S_best := S
        for j := 1 to max_steps do
            if S satisfies all constraints then
                return S
            else
                Randomly select words w_1, w_2 ∈ S that violate one of the
                    constraints
                M := N(w_1) U N(w_2), i.e. all words from the
                    neighbourhoods of w_1 and w_2
                select word w' from M such that number of constraint violations
                    in S is maximally decreased
                if w' ∈ N(w_1) then
                    replace w_1 by w'
                else
```

```
        replace w₂ by w'
    end if
    if S has no more constraint violations than S_best then
        S_best := S;
    end if
   end if
  end for
 end for
 return S_best
end StochasticLocalSearch for for DNA Code Design
```

Note that in each iteration, the best pool $S_{best}$ found is stored, that is, the pool with the least number of violated constraints. The SLS returns $S_{best}$. Also, note that the algorithm has two for loops. In the outer for loop, the pool is initialized and therefore the implementation of the code can be parallelized with max_tries independent runs of the SLS.

It is to be understood that a modified version of the SLS described herein, or another optimization method, can be used to find a pool that satisfy a list of constraints.

Analysis of Template Diversity Through Codeword Entropy

In some aspects, the present disclosure provides methods for using information theoretic measurements of codeword entropy in amplified sequences derived from a pool of template molecules, in quality control, mutation calling and other applications to NGS sequencing.

In some embodiments, codewords are attached (for example ligated or synthesized with target primer sequences, such as those described herein for the primer sequences of CG001.v2). Attachment of codewords to primers may, in general, bypass the inefficiency and unpredictability of ligation to template molecules, which is especially problematic for DNA templates retrieved from archival specimens, such as formalin fixed paraffin embedded (FFPE) tissue samples that are a routine method of patient tissue diagnosis. In alternative embodiments, the codewords may be attached to target molecules. Accordingly, in some embodiments, the methods described herein can be applied to template-codeword attached templates.

Figure 5:
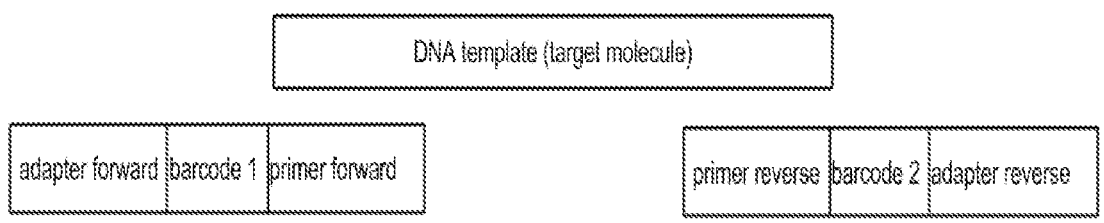
FIG. 5 is a schematic diagram of DNA template and primers for a NGS sequencing reaction.

Since a pair-end sequencing approach is used in the NGS process, two different primers are priming in an NGS sequencing reaction, the molecular barcode, and the primer; see FIG. 5. In some embodiments, the adapter may be used to identify the sample designed for each end. Furthermore, a different barcode is attached (for example ligated or synthesized) to each target primer, to increase coding efficiency. The resulting modified primer may further include a common adapter sequence for attachment in the demultiplexing step, by for example an additional PCR reaction in which the sample is coded through an additional DNA index. However, the analysis of template diversity does not require the use of the adapter.

In some embodiments, a single codeword or molecular barcode is attached to one of the two primers in a primer pair. In alternative embodiments, the same or different codewords or molecular barcodes are used in a primer pair.

In alternative embodiments, codeword or molecular barcodes with or without attached adapter sequences may be ligated directly to a nucleic acid template molecule, such as a DNA template molecule, to form a codeword-template molecule, and the subsequent chimeric temple-codeword[-adapter] molecules may be amplified using the common primer. Without being bound to any particular theory, this approach may be useful for sequencing of pools of DNA fragments from a whole genome, or obtained from enrichment capture hybridisation of genomic DNA fragments. A person skilled in the art will be able to apply the methods of entropy disclosed herein in this situation.

In general, analysis of template diversity through codeword entropy may be performed by:
  random attachment of codewords to amplified products or templates using a pool of balanced or unbalanced performance codewords;
  PCR-NGS sequencing of target loci, using for example the methods outlined in the assay described as CG001v2;
  alignment and counting of the abundance of codewords; and
  comparing observed and expected entropy coupled to a decision procedure for determining true variation from artifact and estimation of template pool size.

Estimating Expected Entropy in DNA Codewords During PCR Sequencing, with a Performance Idealised Codeword Pool Expected measures of entropy under different performance characteristics of codewords may be determined as follows. The expected measures may be used in subsequent steps for determining actual performance and for mutation calling.

In some embodiments, a set of high diversity pool of codewords M are generated and attached to target primers by for example synthesis or ligation. In alternative embodiments, DNA codewords are attached stochastically to template molecules by for example ligation. In some embodiments, the observed codeword diversity may be determined using Shannon entropy. It is however to be understood that any other suitable diversity metric, such as the Simpson index, may be used.

A PCR reaction starts with an initial number of template molecules m that will interact with the pool of codewords annotated primers. The diversity of a given codeword set observed in the amplified product of a PCR process with c cycles ($A_c$) is calculated using the Shannon entropy H defined as $$H(A_c) = -\Sigma_{w_j \in w} P(w_j) \log_2 P(w_j) \quad \text{where} \quad P(w_j) \log_2 P(w_j) = 0 \text{ if } P(w_j) = 0$$

The entropy of codewords observed in a given PCR cycle thus depends on several factors such as the pool size $|M|$, the multiplicity $i(w_j)$ of each codeword $w_j$ in the pool M and the initial number of template molecules m.

The codeword entropy of a given PCR cycle can be estimated as follows. First the number of amplified sequences and the minimum number of unique codewords required in each PCR cycle is estimated. Two different codeword pools are generated, one for the forward primer $M_F$ and a different one for the reverse primer $M_R$. Therefore, two sets of codewords associated to the amplified product are observed at the end of a given PCR cycle: one for the forward primer and a second one for the reverse primer. For instance, FIG. 6 shows the amplified sequences for the first four PCR cycles as well as the codewords, of forward and reverse primers, associated with each amplified sequence. Table 4 contains the list of codewords found in each cycle of a perfect PCR process as well as the corresponding entropy. For example, in the 4th PCR cycle, there are 22 amplified sequences, 14 unique codewords in each end, and a codeword entropy of 3.66.

TABLE 4

Statistics on the number of amplified sequences and codewords observed in the first four cycles of a perfect PCR reaction.

| PCR cycle K | number of amplified sequences | Codewords ligated to forward primers on amplified sequences | Codewords ligated to reverse primers on amplified sequences | number of unique code-words | expected code-word entropy |
|---|---|---|---|---|---|
| 2 | 2 | $w_4, w_2$ | $w_1, w_5$ | 2 | 1.0 |
| 3 | 8 | $w_8, w_4,$ $w_{10}, w_2,$ $w_{12},$ | $w_3, w_1,$ $w_9, w_{11},$ $w_5, w_{13}$ | 6 | 2.5 |
| 4 | 22 | $w_{15}, w_8,$ $w_{16}, w_4,$ $w_{19}, w_{10},$ $w_{21}, w_2,$ $w_{23}, w_{12},$ $w_{25}, w_6,$ $w_{27}, w_{14}$ | $w_7, w_3,$ $w_{17}, w_1,$ $w_{18}, w_9,$ $w_{20}, w_{22},$ $w_{11}, w_5,$ $w_{24}, w_{26},$ $w_{13}, w_{28}$ | 14 | 3.66 |

The number of amplified sequences and the number of unique codewords can be inferred in general. There are three types of sequences that can appear in a given PCR cycle: (1) the original DNA template, (2) primer extensions from original templates that have one codeword in one end, and (3) primer extension products from primer extension products that have two codewords, one in each end. Table 5 contains the number of sequences of each type observed in a given PCR cycle. It also contains the general formula to obtain the number of sequences observed of each type in any given PCR cycle c.

TABLE 5

Number of different sequence types found per PCR cycle.

| cycle | original DNA template | primer extension products from original DNA template | primer extension products from primer extension products | total number of sequences |
|---|---|---|---|---|
| 0 | 2 | 0 | 0 | 2 |
| 1 | 2 | 2 | 0 | 4 |
| 2 | 2 | 4 | 2 | 8 |
| 3 | 2 | 6 | 8 | 16 |
| 4 | 2 | 8 | 22 | 32 |
| c | 2 | 2 * c | $2^{c+1} - 2*c - 2$ | $2^{c+1}$ |

Figure 7:
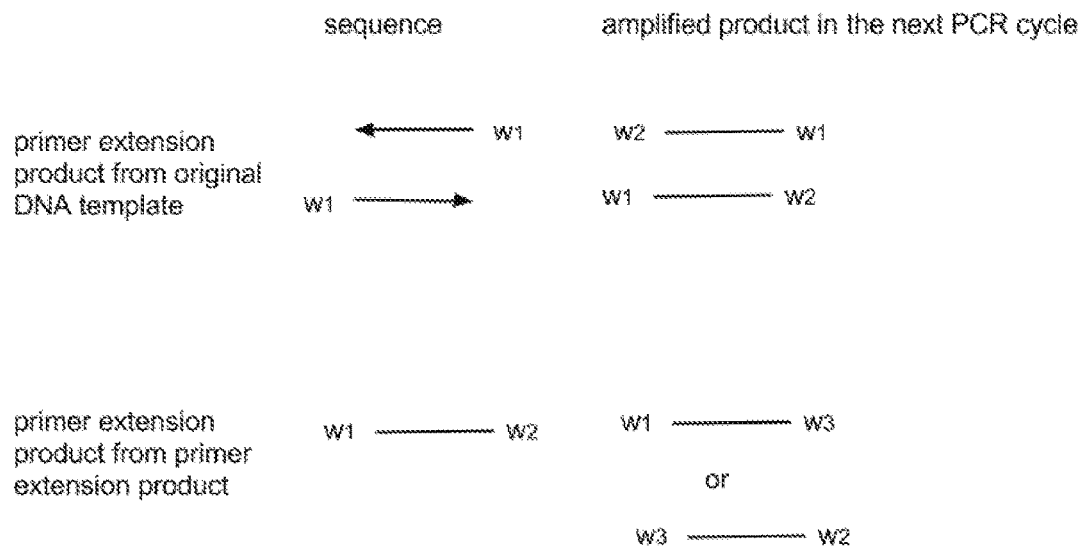
FIG. 7 is a schematic diagram of mechanisms by which codewords are added during amplification.

To obtain the number of unique codewords per PCR cycle, note that each primer extension products from original DNA template contain one codeword $w_1$. However when amplified, the product will contain codeword $w_1$ and a new codeword in the other end $w_2$. Similarly, primer extension products from primer extension products contain two codewords $w_1$ and $w_2$. These sequences will be amplified in one direction and the new product will contain one new codeword $w_3$. Therefore, each time a sequence is amplified a new codeword is introduced (FIG. 7).

Since each sequence type produces one new codeword in the next cycle, the total number of unique codewords per cycle c is equal to $2^c-2$ (Table 6).

TABLE 6

Number of unique codewords per PCR cycle

| cycle | number of primer extension products from original DNA template in the previous cycle | number of primer extension products from primer extension products in the previous cycle | number of unique codewords \|W\| |
|---|---|---|---|
| 2 | 2 | 0 | 2 |
| 3 | 4 | 2 | 6 |
| 4 | 6 | 8 | 14 |
| c | 2 * (c − 1) | $2^c - 2(c - 1) - 2$ | 2 * (c − 1) + $2^c -$ 2(c − 1) − 2 = $2^c - 2$ |

The frequency $f_{i,c}$ of a given codeword $w_1$ in cycle c can also be computed in a perfect PCR process as $f_{j,c}=f_{i,c-1}+1$ with $f_{i,c_0}=1$ and $c_0$ the cycle where $w_1$ is first observed. That is, the codeword frequency is expected to increase by one in each PCR cycle. Table 1 shows the frequency of the codewords that appear in the first and second cycles in FIG. 6.

Under ideal circumstances, each codeword in the pool is uniformly distributed with multiplicity one, that is $i(w_j)$ =i~Uniform(1), where Uniform refers to the Uniform statistical distribution. However, in practice the observed multiplicity distribution can differ from the uniform due to errors in oligonucleotide synthesis, inefficiency of oligonucleotide synthesis of some sequences due to thermodynamic constraints intrinsic to the sequence, inefficient PCR amplification and sequencing of the codeword due to similar issues. In fact any coding method may suffer from non-Uniform characteristics. The impact of non-Uniform distributions of codes may be handled as follows, providing an estimation of the entropy characteristics during PCR sequencing.

The first step is to identify the empirical distribution of codeword multiplicity. The ideal distribution is Uniform, however other distributions can be observed in practice such as a Poisson distribution, used to model the number of events observed in a period of time. The Negative Binomial distribution can also be observed when the mean and the variance of the distribution differ. As a first step, exploratory analysis and Q-Q plots can be used to compare the empirical distribution with known distributions. Then maximum likelihood estimation can be used to obtain the probability of the observed codeword multiplicity distribution given the chosen probability distribution model. Furthermore, a goodness of fit test can also be used to indicate whether or not it is reasonable to assume that a random sample comes from a specific distribution.

The next step is to determine the expected codeword entropy distribution given a specific codeword multiplicity distribution that has been characterized. The codewords observed in a given PCR cycle can be modeled by statistical sampling with replacement in the codeword pool |M|, where the sample size depends on the number of amplified sequences. Sampling with replacement is used since the root elements $w_j$ can have a multiplicity greater than one. Furthermore, errors during the PCR reaction can affect the entropy of codewords, for instance, primers can potentially dissociate and re-prime.

The following sections illustrate the behaviour of codeword entropy in the $4^{th}$ PCR cycle when different multiplicity codeword distributions are present. In every case, the entropy distribution was obtained by generating 1000 independent samples with replacement of a fixed pool with a determined multiplicity distribution of root elements. The behaviour of codeword entropy between in m=1 template (number of templates defined as m) and multiples of m, to exemplify how the entropy methods disclosed may distinguish errors incorporated at late cycles in the PCR sequencing process, or randomly distributed single template variations, from true alleles is shown as follows.

(i) Uniform Multiplicity Distribution

A perfect PCR reaction with four cycles has fourteen different codewords, in the preferred embodiment (see FIG. 6, Table 4). If $i(w_j)=i\sim\text{Uniform}(1)$, the pool size required for the amplification of m template molecules is $|M|=m*\Sigma_{j\in|w|} i(w_j)=m*14$. This corresponds to the population size where the sample with replacement is drawn. The sample size is n=22*m since each template molecule has 22 amplified sequences after four PCR cycles. In this case, the probability of observing a given codeword in the pool is $P(w_j)=i(w_j)/|M|=1/(m*14)$.

Figure 8:
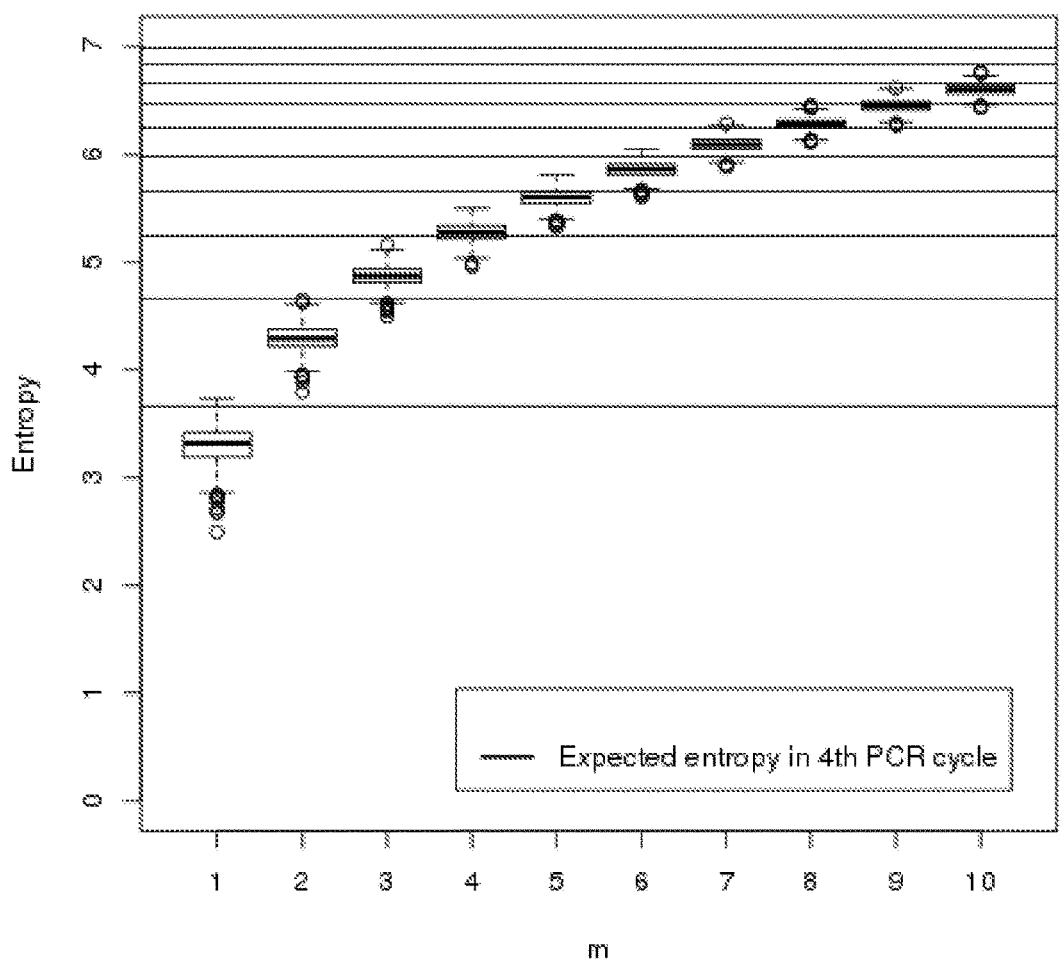
FIG. 8 is a boxplot of codeword entropy distributions in the $4^{th}$ PCR cycle for i~U(1)
Figure 9:
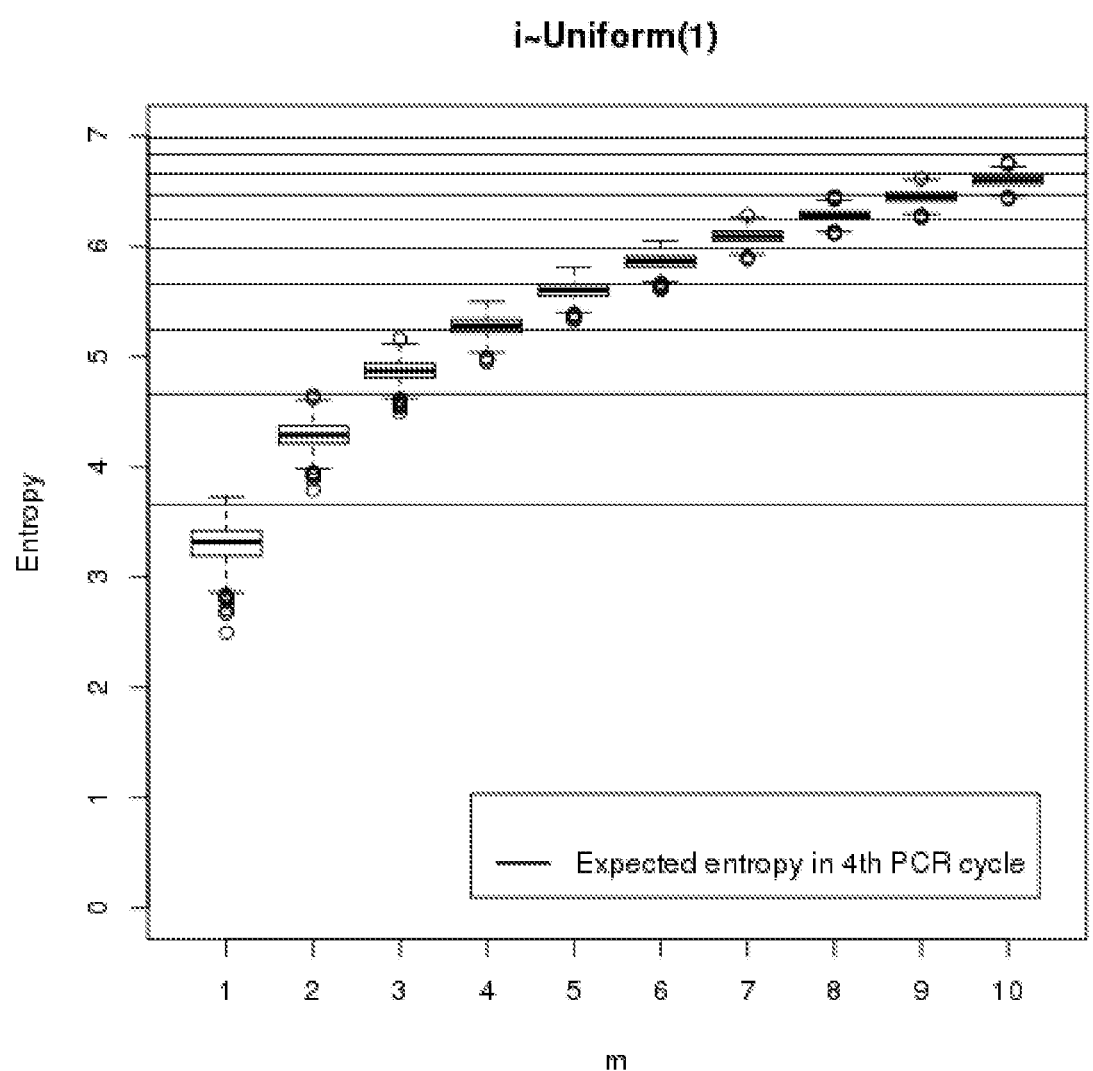
FIG. 9 is a boxplot showing comparison of codeword entropy distribution in the $4^{th}$ PCR cycle for i~U(1) and i~U(3) where labels in the x-axis correspond to the parameters used to generate each distribution (for instance, u1_m1 corresponds to i~U(1) and m=1)

FIG. 8 shows the observed entropy distributions for different number of initial templates m. These distributions were generated by calculating the entropy of 1000 independent samples with replacement from a uniform codeword multiplicity distribution with parameter one. Higher entropies are observed when the number of initial template molecules m increases. However, the variance in entropy decreases as m increases. This figure also contains the expected entropy, represented with a horizontal line, for different values of m. The expected entropy is always higher than the observed entropy. When the multiplicity of codewords is uniformly distributed, the entropy distribution is independent of the codeword multiplicity $i(w_j)$. This is exemplified in FIG. 9 with $i\sim\text{Uniform}(1)$ and $i\sim\text{Uniform}(3)$.

In ideal circumstances, the multiplicity of codewords is uniformly distributed. However, variations in the multiplicity can occur due to errors in oligonucleotide synthesis. The entropy methods described herein can however still be used to distinguish errors incorporated at late PCR cycles when there is an unbalanced representation of codewords in the pool.

(ii) Poisson Multiplicity Distribution

Variation in the codeword multiplicity can be modeled using a Poisson distribution with parameter $\lambda$, that is $i\sim P(\lambda)$. The Poisson distribution is used to model the number of events observed in a period of time. In this case the events are the codewords $w_j$ generated during oligonucleotide synthesis. If $i\sim P(\lambda)$, not all codewords have the same multiplicity, however the mean and variance is equal to $\lambda$. The density function of a Poisson distribution is defined as $$P(i=k) = \frac{\lambda^k e^{-\lambda}}{k!}$$

where $\mu[i]=\lambda=\sigma^2[i]$ with $k\in\{0, 1, \ldots\}$.

Figure 10:
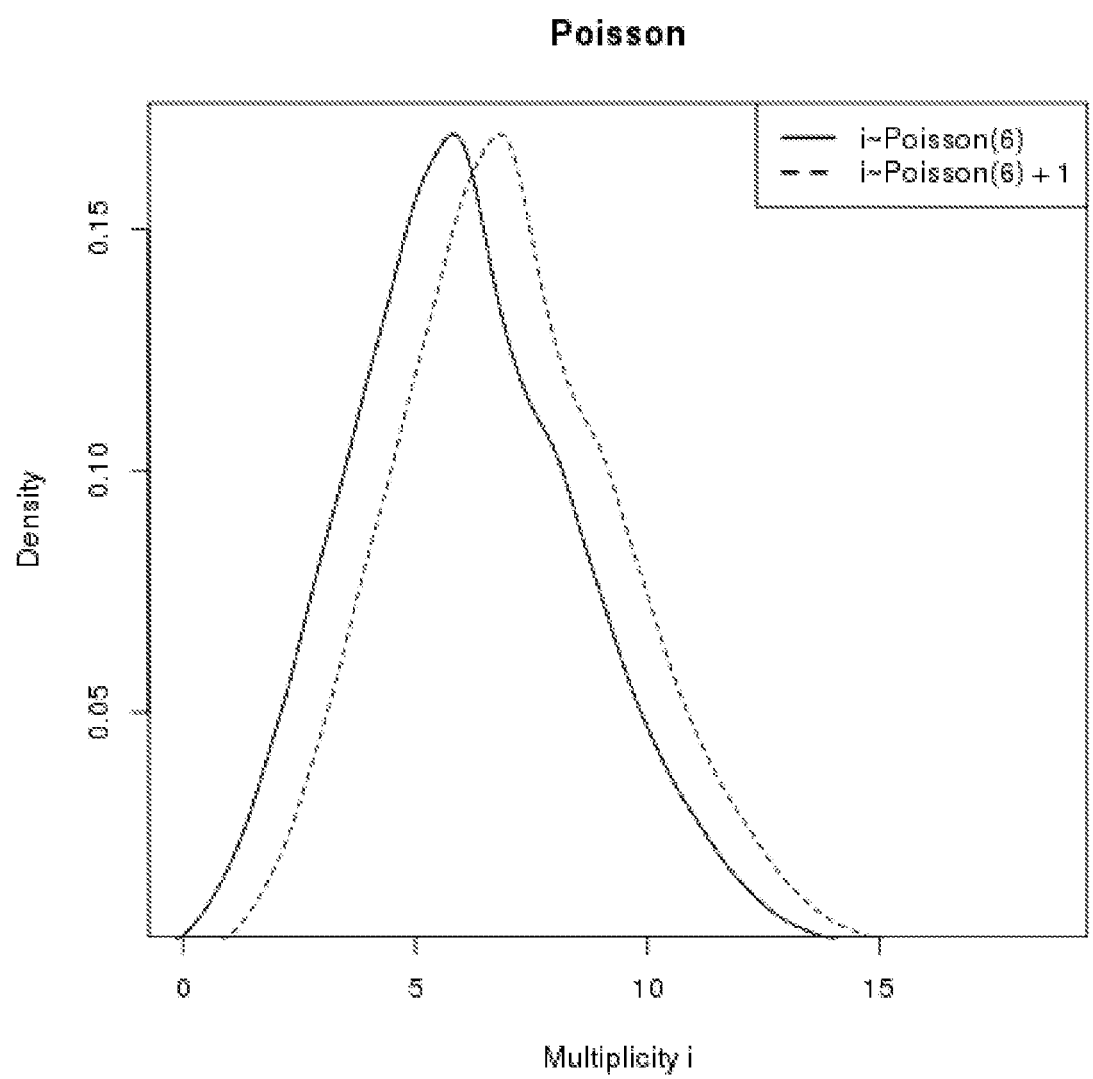
FIG. 10 is a graph showing Poisson distribution models of variation in codeword multiplicity where the solid curve corresponds to a randomly generated Poisson distribution i~P($\lambda$=6), where $\hat{\mu}[i]$=5.943 and $\hat{\sigma^2}[i]$=6.084 and the dashed curve has the same distribution with values shifted by one (in this case $\hat{\mu}[i]$=6.943 and $\hat{\sigma^2}[i]$=6.084)

To model this case, a Poisson sample was generated and the values were shifted by one since the codeword multiplicity i should be greater than zero. FIG. 10 shows a randomly generated Poisson distribution as well as the modified distribution where all values are shifted by one. Note that the mean is increased by one unit in the shifted distribution but the variance remains the same.

The quality of the PCR process is better assessed when the number of cycles is larger than 1. The reason is that if the templates are not well amplified at the end of c PCR cycles, the codeword entropy of the amplified product can be identified as the expected entropy associated with a lower PCR cycle c' where c'<c.

Estimating Expected Entropy in DNA Codewords During PCR Sequencing, with a Non-Uniform Performance Codeword Pool.

Figure 11:
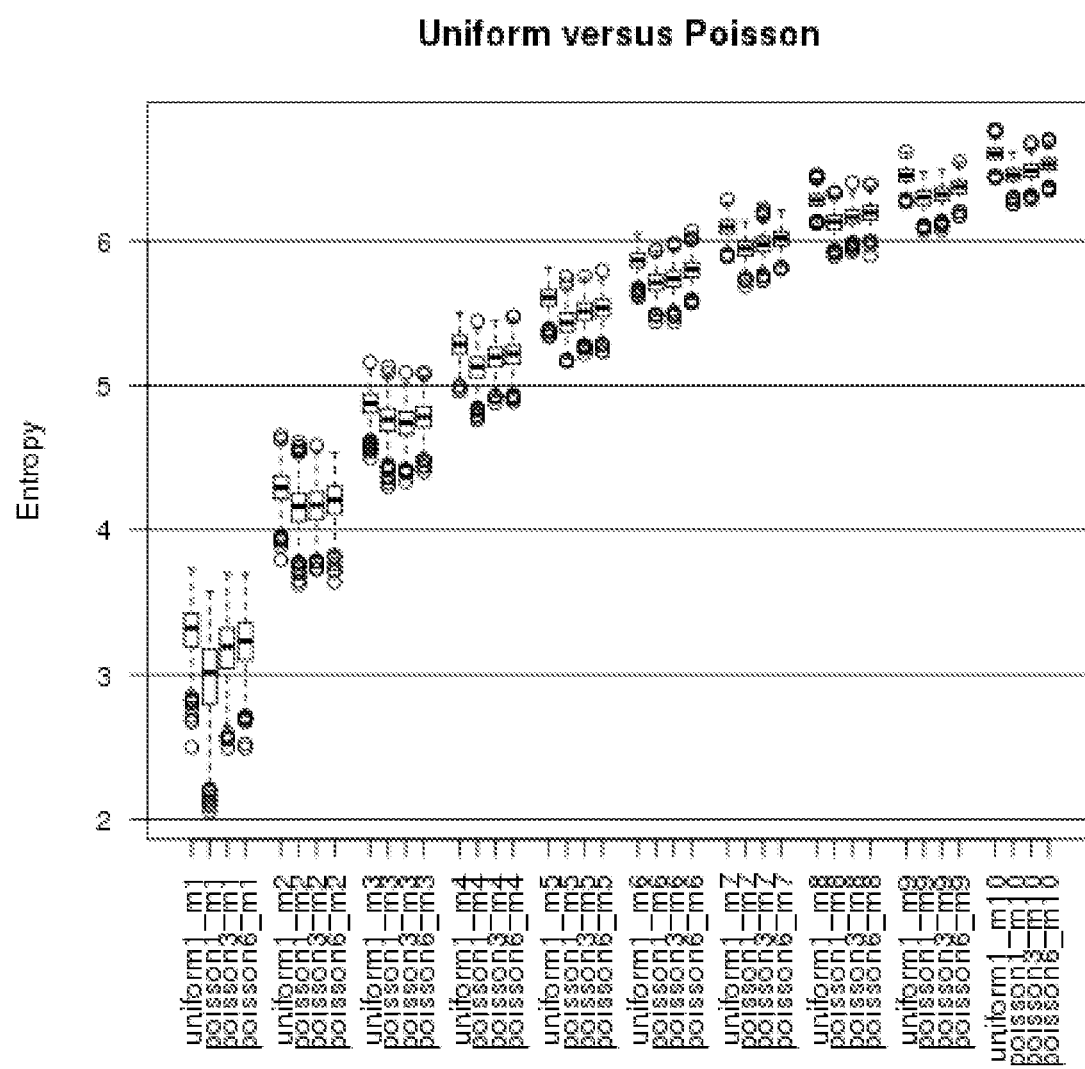
FIG. 11 is a graph showing comparison of codeword entropy distribution in the $4^{th}$ PCR cycle for i~U(1) and i~P($\lambda$) for $\lambda$=1,3,6 and m=1 . . . 10.
Figure 12:
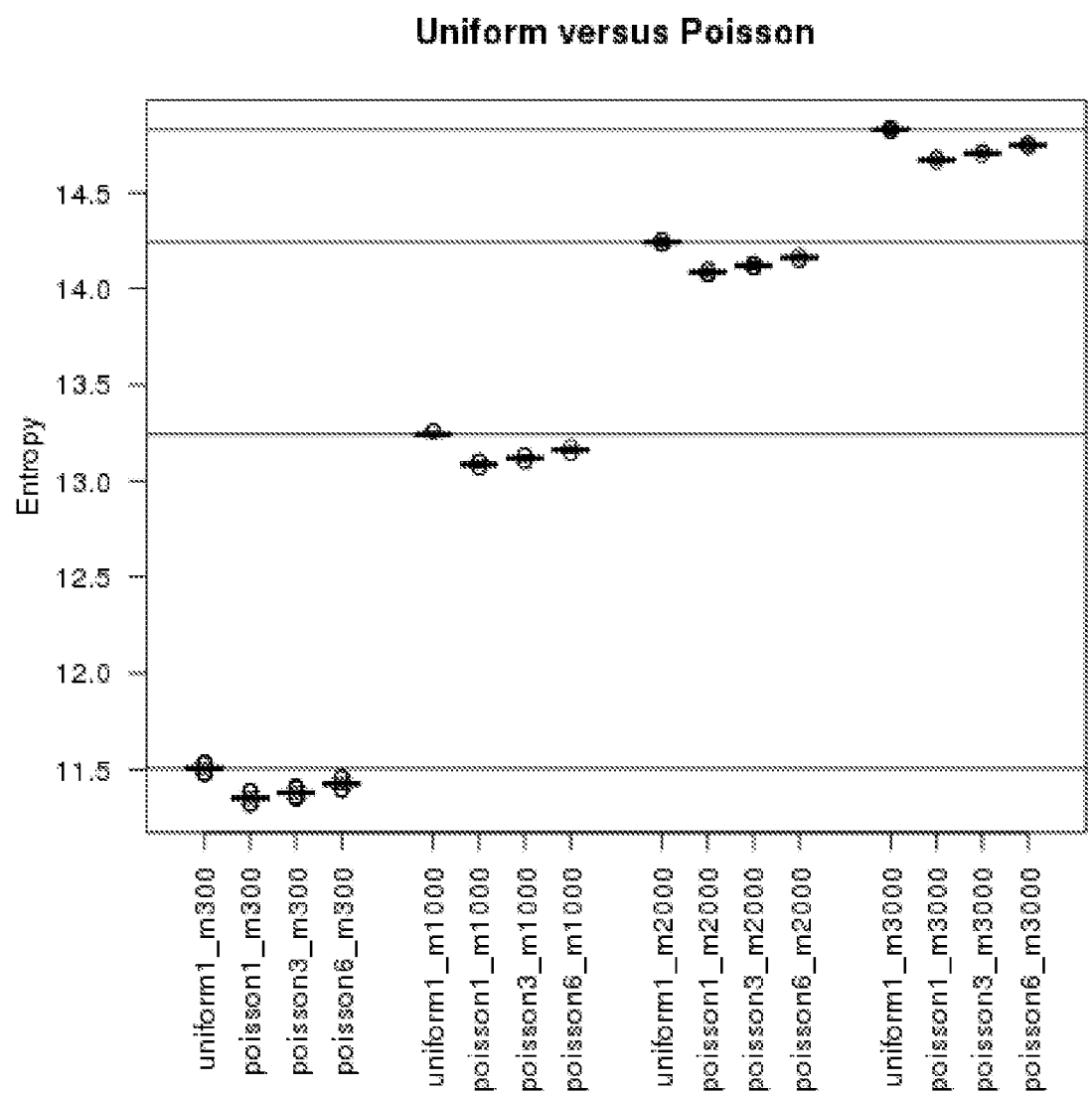
FIG. 12 is a graph showing comparison of codeword entropy distribution in the $4^{th}$ PCR cycle for i~U(1) and i~P($\lambda$) for $\lambda$=1,3,6 and m=300, 1000, 2000, 3000.
Figure 13:
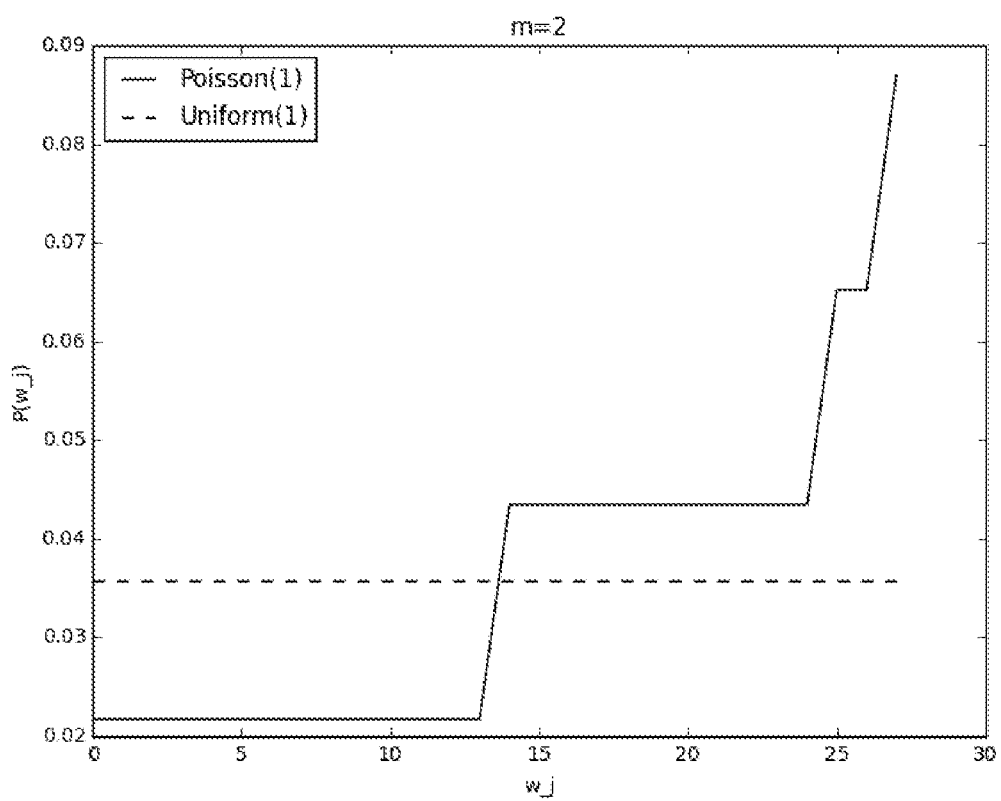
FIG. 13 is a graph showing probability of occurrence of each codeword $w_j$ in the $4^{th}$ PCR cycle, where $$P(w_k) = \frac{1}{14*m} \text{ when } i \sim U(1), \text{ and } P(w_k) = \frac{i(w_k)}{[m*\Sigma_{j=1}^{14} i(wj)]}$$

FIGS. 11 and 12 show the entropy distributions when the multiplicity follows a Uniform distribution and a Poisson distribution with different $\lambda$ values. The entropy distributions were obtained by calculating the entropy of 1000 independent samples from a fixed codeword multiplicity distribution. The entropy decreases when the multiplicity follows a Poisson distribution. The reason is that some codewords have a higher probability of occurrence and therefore the sample diversity is reduced compared to the sample obtained when all codewords have the same probability of occurrence. FIG. 13 shows the probability of sampling each codeword in the pool when the multiplicity is Uniform and Poisson with parameter $\lambda=i=1$. When the multiplicity follows a Poisson distribution, the entropy increases with larger values of $\lambda$ as the number of codeword occurrences in the pool becomes more uniform. Furthermore, the entropy increases and the variance decreases with an increase in the number of initial template molecules m.

(iii) Negative Binomial Multiplicity Distribution

The Poisson distribution assumes that the mean and the variance of a distribution are the same. However, over dispersion can be observed in practice when the variance in the multiplicity is greater than the mean. This case can be modeled with the Negative Binomial distribution, that is, $i\sim\text{NB}(r; p)$. The distribution models the probability of the number of successes in a sequence of independent Bernoulli trials before a specified number of failures r occurs. The probability of success of each Bernoulli trial is p. The density function is defined as $P(i=k)=C(k+r-1, k)p^k (1-p)^r$ with $k=0, 1, 2, \ldots$ where C are the combinations of k success in k+r-1 Bernoulli trials. The mean and the variance are $\mu[i]=pr/(1-p)$ and $\sigma^2[i]=pr/(1-p)^2$ respectively.

To model this case, a Negative Binomial sample was generated and the values are shifted by one since the codeword multiplicity ishould be greater than zero. FIG. 14 shows a randomly generated Negative Binomial distribution with parameters r=6 and p=0.5 as well as the modified distribution where all values are shifted by one. Note that the mean is increased by one unit in the shifted distribution but the variance remains the same.

To investigate the effect that the variance has in the entropy, several samples were generated with different parameters of a Negative Binomial distribution. Table 7 contains the mean and variance of each generated sample. The parameters p and r were varied in such a way that the sample mean $\hat{\mu}$ was fixed. For instance, when $\hat{\mu}=1$, the values of the variance ($\hat{\sigma}^2$) range from 2.08 to 10.3. Note that as the probability of success p increases, the sample variance $\hat{\sigma}^2$ decreases. Furthermore, for a fixed p, the sample variance increases as the sample mean $\hat{\mu}$ increases.

TABLE 7

Mean and variance of Negative Binomial distribution samples with different parameters. Each sample was generated with parameters p and r = (1-p)/p for p = 0.1, 0.2, . . . , 0.9 and μ = 1, 3, 6. Note that $\hat{\mu} = \mu + 1$ because the values of the samples are shifted by one.

| | μ = 1 | | μ = 3 | | μ = 6 | |
|---|---|---|---|---|---|---|
| p | $\hat{\mu}$ | $\hat{\sigma}^2$ | $\hat{\mu}$ | $\hat{\sigma}^2$ | $\hat{\mu}$ | $\hat{\sigma}^2$ |
| 0.1 | 1.9775952 | 10.3412 | 3.971429 | 88.33062 | 6.959833 | 363.8712 |
| 0.2 | 1.9990952 | 6.058334 | 4.034262 | 48.71634 | 7.072333 | 190.2725 |
| 0.3 | 1.9911905 | 4.314073 | 3.97031 | 32.00824 | 6.895357 | 120.7604 |
| 0.4 | 1.9954524 | 3.485515 | 3.963048 | 24.72175 | 6.903667 | 92.29744 |
| 0.5 | 2.001262 | 2.948045 | 3.986429 | 20.54835 | 7.050595 | 78.13885 |
| 0.6 | 1.998881 | 2.671943 | 3.966214 | 17.2312 | 6.924952 | 65.24668 |
| 0.7 | 2.011976 | 2.458653 | 4.014905 | 16.31712 | 7.016024 | 57.68495 |
| 0.8 | 2.001214 | 2.251838 | 3.997286 | 14.24681 | 7.044333 | 52.4069 |
| 0.9 | 1.9931667 | 2.081693 | 4.015119 | 13.13639 | 6.973619 | 45.47058 |

In order to model the 4$^{th}$ PCR cycle and an initial number of 3,000 DNA templates, the size of each sample was fixed to 42,000. FIG. 15 shows the entropy distributions when the multiplicity follows a Uniform distribution with parameter one and a Negative Binomial distribution with μ=1,3,6 and p=0.1, 0.2, . . . , 0.9. The entropy distributions were obtained by calculating the entropy of 1000 independent samples from a given codeword multiplicity distribution. The entropy observed when the codeword multiplicity follows a negative binomial distribution is lower than the one observed with a uniform codeword multiplicity. For a fixed p, the entropy decreases when μ increases, that is when the sample variance increases. Furthermore, for a fixed μ, the entropy decreases when the parameter p decreases and therefore the variance increases. The relation between the mean entropy and the variance of each distribution is shown in FIG. 16. For a fixed sample mean, the entropy decreases as the variance in the multiplicity distribution increases.

FIGS. 17A-C and 18A-C show the codeword entropy when the initial number of template molecules is m=1, 5 and 10. In general, the entropy lowers when the variance increases. This trend is clearer as m increases.

(iv) Uniform Multiplicity Distribution with Outliers

Another scenario that can occur in practice is where most of the codewords have the same multiplicity except few of them with higher or lower number of occurrences. In this case, the multiplicity is modeled as a uniform distribution with some outliers. In a PCR process with four cycles and m initial template copies, the pool size is computed as $|M|=m*\Sigma_{j=1}^{14} i(w_j)$ with probability of sampling each codeword is $P(w_k)=i(w_k)/(m*\Sigma_{j=1}^{14} i(w_j))$.

In order to simulate this case, a uniform distribution with parameter one was generated with different number of outliers and a random multiplicity that ranges between five and seven. FIG. 19 shows the corresponding entropy distributions from 1000 independent samples when m=5 and |W|=14*5=70. When outliers are introduced, the entropy decreases. However, lower values on the entropy are observed for small number of outliers. Then the entropy increases as the number of outliers increases. When the number of outliers is 70, that is outliers are introduced in every codeword, the entropy is comparable to the one obtained with no outliers.

(v) Uniform Multiplicity Distribution and Different Number of PCR Cycles

In practice not all sequences are amplified as expected. For instance, some sequences are amplified only in the early cycles of the PCR process. To model this situation, we compared the codeword entropy of sequences that are amplified in different PCR cycles when the multiplicity is uniformly distributed. The parameters needed to simulate each case are the population size, the sample size and the probability of sampling a codeword in different PCR cycles. These parameters are included in Table 8.

TABLE 8

Parameters for simulating PCR amplification with two, three, and four different cycles. The parameters correspond to the case where the multiplicity is uniformly distributed.

| | 2$^{nd}$ cycle | 3$^{rd}$ cycle | 4$^{th}$ cycle |
|---|---|---|---|
| number of unique codewords |W| | 2*m | 6*m | 14*m |
| population size |M| = m * $\Sigma_j$ i(w$_j$) | 2*m*i | 6*m*i | 14*m*i |
| sample size | 2*m | 8*m | 22*m |
| P(w$_j$) = i(w$_j$)/|M| | i/(2*m) | i/(6*m) | i/(14*m) |

FIG. 20 shows the entropy distribution for different PCR cycles when i~U(1). The entropy distributions were obtained by generating 1,000 samples with replacement using the parameters shown in Table 8 for different PCR cycles. The entropy observed in the simulations is low with few PCR cycles. This is expected as lower cycles have less number of unique codewords.

Impact of Codeword Incorporation in Amplicon Performance

Amplicon performance was also tested using commercial Normal Female DNA template with 10-mers synthesized into both forward and reverse primers of all 73-target loci of our cancer hotspot multiplex PCR assay. We used 25 PCR cycles and different amounts of input DNA (m). The number of reads per amplicon from this experiment when m=5,000 and 10,000 was compared with four different experiments with commercial Normal Female DNA template, and primers without codewords. These experiments were performed using an Illumina Miseq platform. In these four experiments we used 30 PCR cycles and m=7,575 haploid genomes. FIGS. 23A and B show that the performance with codewords is comparable to the performance without codewords even though the number of PCR cycles is smaller. Note that amplicon performance was analyzed after confirming that there are no preferentially amplified codewords in the pool that can potentially biased the results.

Relation of Starting Templates and Entropy

The entropy is expected to increase as a function of the initial number of templates. This relation is exemplified on a commercial Normal Female DNA (Coriell Biorepository) template with random 8-mers and 10-mers synthesized into both forward and reverse primers of one of the target amplicons in our custom CG001 cancer hotspot multiplex PCR assay. A MiSeq platform was used to sample the reads. The experimental conditions considered for 8-mers are 20 PCR cycles and amount of input DNA of m=10, 50, 100, 500, 1000, 5000, 10000, 50000, 100000. The conditions considered for 10-mers are 25 PCR cycles and m=1, 2, 3, 4, 5, 10, 25, 50, 75, 100, 500, 1000, 2000, 3000, 4000, 5000, 10000, 25000.

FIGS. 24A and B show the codeword entropy per allele in SNP rs13182883 from chromosome 5 at position 136633338 for 8-mers and 10-mers respectively. These plots show the entropy as a function of the initial number of templates m. For the SNP alleles A and G, the general trend is an increase of codeword entropy when the input DNA is approximately in the range m E [10, 4000].

The codeword entropy per amplicon was then analyzed as a function of input DNA. FIG. 25 shows the distribution of codeword entropy for several numbers of starting templates. The entropy was calculated on all codewords from reads that belong to the same amplicon. FIG. 25 shows the desired trend when 50≤m≤4000, where the median entropy increases with the number of initial templates.

DNA Barcode Applications for Quality Assurance

Quality Assurance in diagnostic DNA sequencing is desirable to prevent erroneous information being provided for treatment and management of patients. In the NGS methods, it is highly desirable to incorporate methods which allow for different aspects of quality assurance, which range from detection of process contamination, sample identity, to precise definitions of analytical validity of the results. DNA codewords are used to assess different aspects of the amplified product in the targeted sequencing exemplification introduced in the background, for each of these purposes, as follows.

(1) Detection of Sample or Process Contamination

Different sets of known codeword pools with non-overlapping membership, generated for example as described herein, are selected for use on different days or with different processing batches of samples, for example by incorporation into the primer sequences of CG001v2, but any other primers sequences targeting a region of the genome can also be used. Thus, each experiment has a different codeword set in use at any time. In some embodiments, codewords are attached to primers targeting known polymorphic single nucleotide variants in the human genome. A suitably large number of individual germline polymorphisms is used, to allow for distinguishing different human individuals by virtue of the combination of polymorphic variants detected. The latter may comprise single base variants, deletions or variations in repeat sequences. The number of polymorphisms chosen can be determined as a function of the frequency of a given polymorphism in the population and the number of loci, so as to reduce the likelihood of chance double occurrence to less than an acceptable threshold. An acceptable threshold may be 1/1000000, but anywhere between 1/1000 and 1/1000000 or less than 1/10000000 can also be used. A suitable number of single base polymorphisms may be 16, but 10, 11, 12, 13, 14, 15, 17, 18, 19, 20, 21, 22, 23, 24, 25, 26, 27, 28, 29, 30 or larger numbers may be used. The dual use of germline polymorphisms and DNA barcodes allows for unique identification of an individual DNA template during multiple sequencing and informatic laboratory steps and the presence of a defined set of codewords allows for the detection of plate to plate, or assay to assay or day to day cross contamination in laboratory workflows.

(2) Codeword Diversity to Detect Inadequate Template Diversity in PCR

The actual performance of codeword entropy distributions may be obtained, for example as described herein, from several serial dilution experiments in an independent DNA template control, by diluting templates from about 3000 copies, in steps down to a single copy and establishing the measured entropy at different target loci at the different dilutions of known template. In some embodiments, as few as 4 molecules may be used. In alternative embodiments, greater than 3000 copies may be used. In alternative embodiments, between 4 to 3000 copies, or any number in between, such as 10, 50, 100, 500, 1000, 1500, 2000, 2500, etc. may be used. The serial dilutions give different concentrations of initial template molecules. A person skilled in the art would understand how to conduct a serial dilution experiment to obtain a relationship between starting templates as an input and entropy, a measured property of the method, as an output, in a manner similar to any assay where a defined input is used for standardizing assay performance over a range of measurements. Higher codeword entropies are expected for higher concentrations of initial template molecules. This is exemplified in FIG. 26 with the entropy of the allele SNPs. For a fixed concentration, the experiment is conducted at least once but preferably repeated two or more times to obtain the codeword entropy distribution. Then, for a DNA template of interest, the entropy of the amplified product is compared to the corresponding expected entropy distribution with the same concentration of initial template molecules. The reaction may thus be rejected as inadequate, if the associated measurement of entropy is less than expected. This information is incorporated into the overall sample handling process. Quality assurance will also incorporate reference measurements on templates of different age and performance in PCR reactions, and repeated on different days, as part of overall process assurance.

When the amplified product is lower than expected, the observed entropy is lower than the expected entropy distribution, see FIGS. 21A and 21B. As a consequence, the probability of observing H(amplified product) in the empirical entropy distribution is close to zero. If the empirical expected entropy distribution is Normally distributed with parameters $\mu$ and $\sigma^2$, a Z-score test can be used to determine if the entropy of the amplified product x=H (amplified product) is in the tail of the expected distribution. A Z-score for a given value x is defined as $$Z = \frac{\sqrt{n}\,(x-\mu)}{\sigma}$$

and is a measure of the standard deviations away from the mean. In a Z-score test, the null hypothesis is defined as $H_0$: $x=\mu$. The null hypothesis is rejected if the p-value is less than the significance level $\alpha$. Very high or very low (negative) Z scores, associated with very small p-values, are found in the tails of the normal distribution. This indicates that it is very unlikely that the observed value x belong to the expected distribution $N(\mu, \sigma^2)$.

Methods other than the Z-score method can also be applied. For instance, it is possible to determine the quantile of the observed entropy under the assumption that it belongs to the expected entropy distribution. If the observed entropy is an outlier then this suggests an artifact in the PCR process and allows for a rejection of a sample during sequencing/quality control.

Detection of True Mutations in Contrast with PCR/Sequencing Errors or Randomly Distributed Individual Base Variations in Template Molecules One or more of the methods as described herein have application in for example cancer diagnosis, where subpopulations of malignant cells may contain a variant not present in the majority (referred to as clones). Additional applications in the field of infectious agent sequencing, where rare bacterial or viral genomes are to be detected among a population. One or more of the methods as described herein may generally be used in any situation where a rare DNA variant (a "low prevalence true mutation") is being analysed/detected by NGS sequencing among a population background. It is to be understood that the methods described herein find use in any sequences having any variant allele prevalence and it is not required that the variant be a rare variant.

The methods work under the assumption that the distribution of the codeword entropy of variant alleles and the background is different. This is exemplified by comparing the codeword entropy of alleles associated with SNPs and alleles with low frequencies due to sequencing errors or artifacts. The SNPs found in Normal Female samples are listed in Table 9. The artifact positions (positions with sequencing errors) considered for this analysis are in the neighborhood regions, [SNP−5, SNP−3] and [SNP+3, SNP+5], of SNPs listed in Table 10. The codeword entropy was calculated on the minor SNP allele and on all low prevalence alleles in the artifact class, see FIGS. 26 and 27. The median entropy of the artifact alleles remains constant whereas for SNP alleles increases when 25≤m≤4000.

Table 9 shows the SNPs identified in each serial dilution sample with Normal Female. The SNPs and the allele SNPs were verified over several experiments with commercial Normal Female template on the cancer hotspot multiplex PCR assay, described herein, with the following experimental conditions: 30 PCR cycles, m=7575, and primers without codewords. The minor allele, and the % VAF reported in this table correspond to the experiment with codewords, 25 PCR cycles and different number of initial temples.

TABLE 9

| SNP | Chromosome | Position | Minor Allele | % VAF | Initial number of templates, m |
|---|---|---|---|---|---|
| rs6811238 | 4 | 169663615 | G | 18.78787879 | 2 |
|  |  |  | T | 6.25 | 3 |
|  |  |  | G | 30.21276596 | 25 |
|  |  |  | G | 37.5 | 75 |
|  |  |  | T | 45.45454545 | 100 |
|  |  |  | G | 49.53959484 | 500 |
|  |  |  | G | 49.22820192 | 1000 |
|  |  |  | G | 47.11370262 | 2000 |
|  |  |  | G | 47.82143812 | 3000 |
|  |  |  | T | 48.02997341 | 4000 |
|  |  |  | G | 49.11616162 | 5000 |
|  |  |  | T | 49.48524365 | 10000 |
|  |  |  | G | 49.46315635 | 25000 |
|  |  |  | G | 47.12765957 | 50000 |
| rs13182883 | 5 | 136633338 | A | 49.01960784 | 5 |
|  |  |  | A | 22.16494845 | 25 |
|  |  |  | A | 30.76923077 | 50 |
|  |  |  | G | 43.00518135 | 75 |
|  |  |  | A | 49.59128065 | 100 |
|  |  |  | G | 48.72881356 | 500 |
|  |  |  | A | 48.10495627 | 1000 |
|  |  |  | G | 48.48019006 | 2000 |
|  |  |  | G | 49.00884416 | 3000 |
|  |  |  | G | 49.37838699 | 4000 |

TABLE 9-continued

| SNP | Chromosome | Position | Minor Allele | % VAF | Initial number of templates, m |
|---|---|---|---|---|---|
|  |  |  | G | 48.75362319 | 5000 |
|  |  |  | A | 49.26984652 | 10000 |
|  |  |  | G | 49.72766364 | 25000 |
|  |  |  | A | 49.29501085 | 50000 |
| rs1136201 | 17 | 37879588 | A | 50 | 1 |
|  |  |  | G | 7.692307692 | 2 |
|  |  |  | G | 25 | 3 |
|  |  |  | G | 47.76119403 | 5 |
|  |  |  | G | 0.581395349 | 25 |
|  |  |  | G | 43.61702128 | 50 |
|  |  |  | G | 33.09692671 | 75 |
|  |  |  | G | 40.33613445 | 100 |
|  |  |  | A | 46.20853081 | 500 |
|  |  |  | G | 48.08035368 | 1000 |
|  |  |  | G | 48.60319623 | 2000 |
|  |  |  | G | 49.95445575 | 3000 |
|  |  |  | G | 48.80027501 | 4000 |
|  |  |  | G | 48.17556848 | 5000 |
|  |  |  | A | 49.60802989 | 10000 |
|  |  |  | G | 49.41942294 | 25000 |
|  |  |  | A | 49.56114029 | 50000 |
| rs1050171 | 7 | 55249063 | A | 50 | 4 |
|  |  |  | A | 47.82608696 | 25 |
|  |  |  | G | 31.08108108 | 50 |
|  |  |  | G | 29.62962963 | 75 |
|  |  |  | A | 39.04282116 | 100 |
|  |  |  | G | 47.27011494 | 500 |
|  |  |  | A | 48.26308476 | 1000 |
|  |  |  | G | 47.50617105 | 2000 |
|  |  |  | G | 48.75805325 | 3000 |
|  |  |  | G | 49.7684342 | 4000 |
|  |  |  | G | 48.99005125 | 5000 |
|  |  |  | G | 49.76593694 | 10000 |
|  |  |  | G | 49.40141818 | 25000 |
|  |  |  | G | 48.82356652 | 50000 |
| rs2228230 | 4 | 55152040 | C | 45.99358974 | 3 |
|  |  |  | T | 0.026838433 | 4 |
|  |  |  | C | 47.79766979 | 10 |
|  |  |  | T | 32.88764718 | 25 |
|  |  |  | T | 45.28301887 | 50 |
|  |  |  | T | 45.33333333 | 75 |
|  |  |  | T | 40.98883573 | 100 |
|  |  |  | C | 47.55186722 | 500 |
|  |  |  | C | 46.40104352 | 1000 |
|  |  |  | T | 48.81163687 | 2000 |
|  |  |  | C | 49.32325691 | 3000 |
|  |  |  | C | 49.71204583 | 4000 |
|  |  |  | T | 49.344145 | 5000 |
|  |  |  | T | 48.74820144 | 10000 |
|  |  |  | C | 48.7725705 | 25000 |
|  |  |  | C | 49.80848297 | 50000 |

Table 10 shows that positions considered for the artifact class are the neighborhood regions [SNP−5, SNP−3] and [SNP+3, SNP+5] of SNP positions listed in this table.

TABLE 10

| SNP | Chromosome | Position |
|---|---|---|
| rs6811238 | chr4 | 169663615 |
| rs576261 | chr19 | 39559807 |
| rs10092491 | chr8 | 28411072 |
| rs1821380 | chr15 | 39313402 |
| rs9951171 | chr18 | 9749879 |
| rs1058083 | chr13 | 100038233 |
| rs13182883 | chr5 | 136633338 |
| rs2981448 | chr10 | 123279745 |
| rs2071616 | chr10 | 123279795 |
| rs3738868 | chr2 | 29432625 |
| rs1136201 | chr17 | 37879588 |
| rs1050171 | chr7 | 55249063 |
| rs12628 | chr11 | 534242 |

TABLE 10-continued

| SNP | Chromosome | Position |
|---|---|---|
| rs2230587 | chr1 | 65311262 |
| rs2228230 | chr4 | 55152040 |

True low prevalence variants can be distinguished from sequencing errors by using supervised or unsupervised classification methods. Supervised classification methods are known to those of skill in the art and include, without limitations, methods that include the use of a training set.

The classes considered are (1) true mutations and (2) sequencing and/or polymerase errors labeled as artifacts. The performance of the classification methods depends on the selected features. We demonstrate the performance of several supervised methods using two features for classifying variants: (1) the codeword entropy of amplified reads with low prevalence variants and (2) the coverage defined as the number of amplified reads in the position of the variant. The scipy library from python was used to run these algorithms with the default parameters, unless specified.

Linear Support Vector Machine (SVM) with balanced weights where the weights associated with classes are inversely proportional to the class frequencies. That is, $$w_y = \frac{num\_samples}{num\_classes * |y|}$$

where y∈{artifact, mutation}.

Radial Basis Function (RBF) SVM with balanced weights.

Nearest Neighbour. A test point is classified by assigning the label which is most frequent among the k training samples nearest to the query point, where k=3.

Logistic Regression with balanced weights.

AdaBoost

Linear Discriminant Analysis

Random Forest with maximum depth of the tree max_depth=5, number of features to consider when looking at the best split max_features=1, and balanced weights.

Quadratic Discriminant Analysis

Decision Tree with maximum depth of the tree max_depth=5, and balanced weights.

Gaussian Naïve Bayes

These methods were tested using mixtures of Normal Female genomic DNA and Horizon QMRS multiplex reference DNA (prepped in-house from FFPE scrolls), with random 10-mers synthesized into both forward and reverse primers of all 73 CG001 target loci. PCR reactions were run for 25 cycles. The combined input DNA for each reaction was kept at 5000 haploid copies, with two mixtures: (1) 100% QMRS and (2) 10% QMRS+90% Normal Female.

Table 11 shows the list of mutations considered in the true mutation class (the list of mutations found in QMRS combined with Normal Female (NF)).

TABLE 11

List of mutations found in QMRS combined with Normal Female (NF)

| Variant | Chr | Position | Mutation | % VAF 100% QMRS | % VAF 10% QMRS + 90% NF |
|---|---|---|---|---|---|
| EGFR G719S | chr7 | 55241707 | G –> A | 25.62% | 6.75% |
| EGFR T790M | chr7 | 55249063 | G –> A | 12.55% | 39.91% |
| EGFR L858R | chr7 | 55259515 | T –> G | 3.58% | 0.86% |
| KRAS G13D | chr12 | 25398281 | C –> T | 14.70% | 3.63% |
| KRAS G12D | chr12 | 25398284 | C –> T | 5.72% | 2.12% |
| NRAS Q16K | chr1 | 115256530 | G –> T | 15.10% | 4.22% |
| cKIT D816V | chr4 | 55599321 | A –> T | 8.40% | 2.50% |
| PIK3CA H1047R | chr3 | 178952085 | A –> G | 17.82% | 5.50% |

The observed percentage variant allele frequency (VAF) for the true mutation class varies between 0.86% and 25.62%. The data for the artifact class was obtained from this experiment in all low prevalence alleles at several positions different to the true mutation positions. The positions considered are in the neighborhood regions, [SNP−10, SNP−5] and [SNP+5, SNP+10] of SNPs listed in Table 10 and the exon regions listed in Table 12. Artifact positions [SNP−5, SNP−3] and [SNP+3, SNP+5] from serial dilutions of Normal Female samples were also included.

TABLE 12

Artifact positions in exon regions from QMRS samples combined with Normal Female

| Chromosome | Positions |
|---|---|
| chr12 | [25398200 − 25398279], [25398285 − 25398320] |
| chr1 | [115256470 − 115256527], [115256531 − 115256580] |
| chr4 | [55599270 − 55599319], [55599345 − 55599360] |
| chr3 | [178952050 − 78952083], [178952087 − 178952110] |
| chr7 | [55259490 − 55259569] except [55259515 − 1, 55259515 + 1] |
| chr7 | [55248984 − 55249079] except [55249063 − 1, 55249063 + 1] and [55249071 − 1, 55249071 + 1] |
| chr7 | [55241677 − 55241738] except [55241707 − 1, 55241707 + 1] |

FIG. 28 shows the entropy and the coverage for all the data, where the artifact class is specified, as well as the true mutations class with the corresponding percentage variant allele frequency. Furthermore, the training and the testing data are also labeled in the same figure.

The predicted class of the true mutations in the testing set is shown in Table 13. The mutation data in the testing set of FIG. 28 is included as well as the predicted class from each classifier. The Matthews correlation coefficient is shown as the performance metric for this testing set. Note that the Matthews correlation coefficient takes into account all testing data and not only the mutation testing data shown in this table. The performance of each classification method was obtained with a 20-fold cross validation. A stratified strategy for cross validation was used to ensure that each fold contains roughly the same proportions of the two classes. The Matthews correlation coefficient, defined as MCC= $(TP*TN-FP*FN)/[(TP+FP)(TP+FN)(TN+FP)(TN+FN)]^{1/2}$, was used as the performance metric since the size of the artifact class is considerable larger than the true mutation class.

TABLE 13

Performance of supervised classification methods.

| Classifier | Entropy | log(num. variants + 1) | % VAF | Predicted class | Matthews Correlation Coefficient |
|---|---|---|---|---|---|
| RBF SVM | 4.807 | 6.495265556 | 2.12 | mut | 1 |
| | 11.54481657 | 12.068407 | 0.86 | mut | |
| | 4 | 3.988984047 | 15.1 | mut | |
| | 15.17300942 | 13.18581881 | 3.58 | mut | |
| | 17.15808726 | 12.24197054 | 39.91 | mut | |
| Logistic Regression | 4.807 | 6.495265556 | 2.12 | mut | 0.912191457 |
| | 11.54481657 | 12.068407 | 0.86 | mut | |
| | 4 | 3.988984047 | 15.1 | mut | |
| | 15.17300942 | 13.18581881 | 3.58 | mut | |
| | 17.15808726 | 12.24197054 | 39.91 | mut | |
| Linear SVM | 4.807 | 6.495265556 | 2.12 | art | 0.773446562 |
| | 11.54481657 | 12.068407 | 0.86 | art | |
| | 4 | 3.988984047 | 15.1 | mut | |
| | 15.17300942 | 13.18581881 | 3.58 | mut | |
| | 17.15808726 | 12.24197054 | 39.91 | mut | |
| Nearest Neighbors | 4.807 | 6.495265556 | 2.12 | mut | 0.773446562 |
| | 11.54481657 | 12.068407 | 0.86 | art | |
| | 4 | 3.988984047 | 15.1 | art | |
| | 15.17300942 | 13.18581881 | 3.58 | mut | |
| | 17.15808726 | 12.24197054 | 39.91 | mut | |
| AdaBoost | 4.807 | 6.495265556 | 2.12 | art | 0.63104851 |
| | 11.54481657 | 12.068407 | 0.86 | art | |
| | 4 | 3.988984047 | 15.1 | art | |
| | 15.17300942 | 13.18581881 | 3.58 | mut | |
| | 17.15808726 | 12.24197054 | 39.91 | mut | |
| Linear Discriminant Analysis | 4.807 | 6.495265556 | 2.12 | art | 0.63104851 |
| | 11.54481657 | 12.068407 | 0.86 | art | |
| | 4 | 3.988984047 | 15.1 | art | |
| | 15.17300942 | 13.18581881 | 3.58 | mut | |
| | 17.15808726 | 12.24197054 | 39.91 | mut | |
| Random Forest | 4.807 | 6.495265556 | 2.12 | art | 0.63104851 |
| | 11.54481657 | 12.068407 | 0.86 | art | |
| | 4 | 3.988984047 | 15.1 | art | |
| | 15.17300942 | 13.18581881 | 3.58 | mut | |
| | 17.15808726 | 12.24197054 | 39.91 | mut | |
| Decision Tree | 4.807 | 6.495265556 | 2.12 | art | 0.63104851 |
| | 11.54481657 | 12.068407 | 0.86 | art | |
| | 4 | 3.988984047 | 15.1 | art | |
| | 15.17300942 | 13.18581881 | 3.58 | mut | |
| | 17.15808726 | 12.24197054 | 39.91 | mut | |
| Quadratic Discriminant Analysis | 4.807 | 6.495265556 | 2.12 | art | 0.63104851 |
| | 11.54481657 | 12.068407 | 0.86 | art | |
| | 4 | 3.988984047 | 15.1 | art | |
| | 15.17300942 | 13.18581881 | 3.58 | mut | |
| | 17.15808726 | 12.24197054 | 39.91 | mut | |
| Gaussian Naive Bayes | 4.807 | 6.495265556 | 2.12 | art | 0.63104851 |
| | 11.54481657 | 12.068407 | 0.86 | art | |
| | 4 | 3.988984047 | 15.1 | art | |
| | 15.17300942 | 13.18581881 | 3.58 | mut | |
| | 17.15808726 | 12.24197054 | 39.91 | mut | |

Table 14 indicates that the non-probabilistic methods SVM and Nearest Neighbors, and the Logistic Regression probabilistic method exhibited the highest performance in this study. The mean of the Matthews correlation coefficient over 20 stratified cross validation runs is shown as the performance metric. Accordingly, in some embodiments, supervised classification methods for use in the methods described herein include methods exhibiting a Matthews correlation coefficient of at least 0.7. Such methods include, without limitation, SVM, Nearest Neighbors, and the Logistic Regression probabilistic methods.

TABLE 14

Performance of supervised classification methods

| Classifier | Mean (Matthews correlation coefficient) |
|---|---|
| RBF SVM | 0.820447319 |
| Linear SVM | 0.8 |
| Nearest Neighbors | 0.75 |
| Logistic Regression | 0.741 |
| Logistic Regression (no weights) | 0.7 |
| AdaBoost | 0.570 |
| Linear Discriminant Analysis | 0.5 |
| Random Forest | 0.5 |
| Decision Tree | 0.45 |
| Quadratic Discriminant Analysis | 0.435 |
| Gaussian Naive Bayes | 0.35 |

Incorporation of Entropy Based Measurements of Template Complexity and Nucleotide Variation in NGS Sequencing The process outlined in FIG. 22 shows how the observed codeword entropy is used in practice to detect the quality of the amplified product. The process starts by characterizing all codewords that are observed. The presence of codewords used to detect contamination from previous experiments is an indication of contamination. If there is no contamination, the process continues with a method to detect under-representation of template in sequencing. If sequences are amplified as expected, the final step is the detection of real variants.

The procedure in FIG. 22 works under the initial assumption that the distribution of the codeword multiplicity is uniform. The non-uniformity of codeword entropies due to technical issues may be detected as described herein and thus incorporated into the calculation of expected background entropy.

Sample Workflow for Sequencing of Patient Tumour Tissues with an NGS sequencing Panel.

Figure 1:
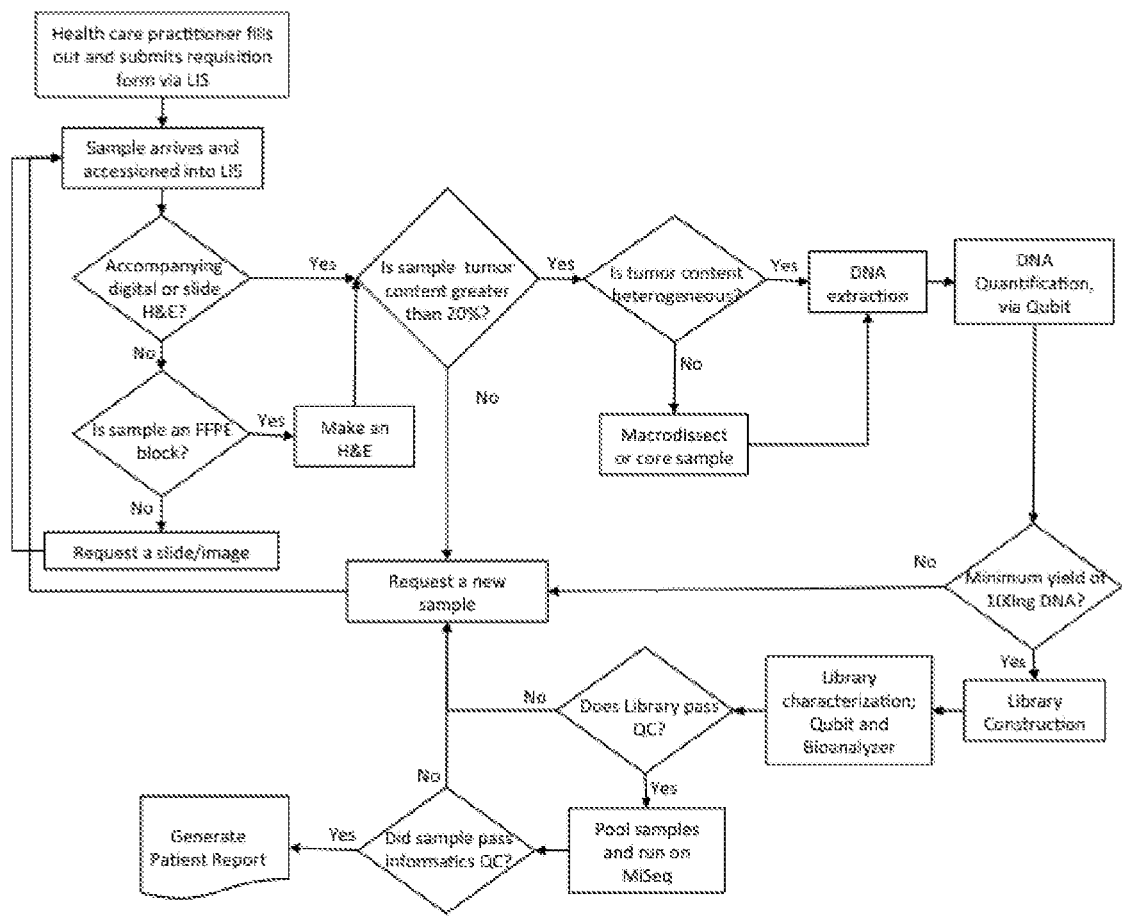
FIG. 1 is a flow chart showing patient sample workflow.

The requesting physician will access a secure external web portal to submit the patient sample requisition form. The sample will then be accessioned into the company's laboratory information management system (LIMS) upon receipt and a hematoxylin and eosin (H&E) slide will be assessed for tumour cellularity of the patient's formalin-fixed paraffin-embedded tissue. If the patient sample does not have sufficient tumour content a new sample will be requested. A new sample will also need to be requested if the sample does not yield greater than 100 ng of DNA after extraction. The sample will also need to meet all the QC requirements after library construction and data analysis. Once all QC metrics have been passed a patient report will be generated and disseminated back to the requesting health care provider. FIG. 1 shows the patient sample workflow.

DNA Extraction

DNA was extracted from 4×10 micron sections of formalin fixed paraffin embedded (FFPE) tissue using the QIAamp DNA FFPE Tissue Kit (Qiagen). The extraction protocol was modified so that deparaffinization consisted of heating the sample to 90° C. in mineral oil. Briefly, 300 ul of molecular grade mineral oil was added to the FFPE scrolls and heated at 90° C. for 20 minutes. The sample was then treated exactly as per Qiagen's instructions after the addition of ATL buffer and Proteinase K. To assist in separating the aqueous layer from the melted paraffin, samples were cooled on ice for 4 minutes just prior to liquid transfer to the spin column. Eluted DNA was quantitated using the Qubit Fluorometer (Invitrogen by Life Technologies).

Library Construction 50 ng of FFPE DNA was used for amplicon generation using the Qiagen Multiplex PCR kit. The amplicons were generated in two pools; Pool A and Pool B for a total of 73 amplicons (Primers listed in Table 15) covering over 90 hotspots and 7 exons (Table 16).

TABLE 15

Primers for Pool A and B

| Primer | Sequence | Pool |
|---|---|---|
| F1 | TCG TCG GCA GCG TCA GAT GTG TAT AAG AGA CAG TGC TGA AAG CTG TAC CAT ACC T (SEQ ID NO: 1) | A |
| F2 | TCG TCG GCA GCG TCA GAT GTG TAT AAG AGA CAG CAG AGC ATA CGC AGC CTG TA (SEQ ID NO: 2) | A |
| F3 | TCG TCG GCA GCG TCA GAT GTG TAT AAG AGA CAG TGG CTA CGA CCC AGT TAC CA (SEQ ID NO: 3) | A |
| F4 | TCG TCG GCA GCG TCA GAT GTG TAT AAG AGA CAG CTG TGT GCA GGC TCC AAG AA (SEQ ID NO: 4) | A |
| F5 | TCG TCG GCA GCG TCA GAT GTG TAT AAG AGA CAG ACT CTA CGT CTC CTC CGA CC (SEQ ID NO: 5) | A |
| F6 | TCG TCG GCA GCG TCA GAT GTG TAT AAG AGA CAG ACA AAG AAA GCC CTC CCC AG (SEQ ID NO: 6) | A |
| F7 | TCG TCG GCA GCG TCA GAT GTG TAT AAG AGA CAG GGT CCT GCA CCA GTA ATA TGC (SEQ ID NO: 7) | A |
| F8 | TCG TCG GCA GCG TCA GAT GTG TAT AAG AGA CAG TAC GCG CCA CAG AGA AGT TG (SEQ ID NO: 8) | A |
| F9 | TCG TCG GCA GCG TCA GAT GTG TAT AAG AGA CAG CTT GTG CTC CCC ACT TTG GA (SEQ ID NO: 9) | A |
| F10 | TCG TCG GCA GCG TCA GAT GTG TAT AAG AGA CAG ACA CCA CGT CCT CTC GTT TC (SEQ ID NO: 10) | A |
| F11 | TCG TCG GCA GCG TCA GAT GTG TAT AAG AGA CAG GGT GGG TAT GGA CAC GTT CA (SEQ ID NO: 11) | A |
| F12 | TCG TCG GCA GCG TCA GAT GTG TAT AAG AGA CAG AGC TAC AAC ATC ACC ACG GG (SEQ ID NO: 12) | A |
| F13 | TCG TCG GCA GCG TCA GAT GTG TAT AAG AGA CAG CAT GAC TGT GGT GCC GTA CT (SEQ ID NO: 13) | A |
| F14 | TCG TCG GCA GCG TCA GAT GTG TAT AAG AGA CAG GAC GCA CTC ACC ATG TGT TC (SEQ ID NO: 14) | A |
| F15 | TCG TCG GCA GCG TCA GAT GTG TAT AAG AGA CAG AGG GTC TGT GCT GGA CTT TG (SEQ ID NO: 15) | A |
| F16 | TCG TCG GCA GCG TCA GAT GTG TAT AAG AGA CAG TAA GGG ACA AGC AGC CAC AC (SEQ ID NO: 16) | A |
| F17 | TCG TCG GCA GCG TCA GAT GTG TAT AAG AGA CAG AGG GTG TCT CTC TGT GGC TT (SEQ ID NO: 17) | A |

TABLE 15-continued

Primers for Pool A and B

| Primer | Sequence | Pool |
|---|---|---|
| F18 | TCG TCG GCA GCG TCA GAT GTG TAT AAG AGA CAG GAA CCA GAC AGA AAA GCG GC (SEQ ID NO: 18) | A |
| F19 | TCG TCG GCA GCG TCA GAT GTG TAT AAG AGA CAG ATG CTT GGC TCT GGA ATG CC (SEQ ID NO: 19) | A |
| F20 | TCG TCG GCA GCG TCA GAT GTG TAT AAG AGA CAG TCT CCC CAC AGA AAC CCA TG (SEQ ID NO: 20) | A |
| F21 | TCG TCG GCA GCG TCA GAT GTG TAT AAG AGA CAG TGC GCT TGA CAT CAG TTT GC (SEQ ID NO: 21) | A |
| F22 | TCG TCG GCA GCG TCA GAT GTG TAT AAG AGA CAG CAG AGA CTT GGC AGC CAG AA (SEQ ID NO: 22) | A |
| F23 | TCG TCG GCA GCG TCA GAT GTG TAT AAG AGA CAG GAA GTG CAA GAA CGT GGT GC (SEQ ID NO: 23) | A |
| F24 | TCG TCG GCA GCG TCA GAT GTG TAT AAG AGA CAG GCT TTT CTA ACT CTC TTT GAC TGC A (SEQ ID NO: 24) | A |
| F25 | TCG TCG GCA GCG TCA GAT GTG TAT AAG AGA CAG TGT CCT TTC TGT AGG CTG GAT G (SEQ ID NO: 25) | A |
| F26 | TCG TCG GCA GCG TCA GAT GTG TAT AAG AGA CAG ACT TAC CAT GCC ACT TTC CCT (SEQ ID NO: 26) | A |
| F27 | TCG TCG GCA GCG TCA GAT GTG TAT AAG AGA CAG AAG TCC AGG CTG AAA AGG CA (SEQ ID NO: 27) | A |
| F28 | TCG TCG GCA GCG TCA GAT GTG TAT AAG AGA CAG CCC CAC TCC TTG CTT CTC AG (SEQ ID NO: 28) | A |
| F29 | TCG TCG GCA GCG TCA GAT GTG TAT AAG AGA CAG ACC TCA TTG TCT GAC TCC ACG (SEQ ID NO: 29) | A |
| F30 | TCG TCG GCA GCG TCA GAT GTG TAT AAG AGA CAG CAC CTC CTT GTC AAC CCT GT (SEQ ID NO: 30) | A |
| F31 | TCG TCG GCA GCG TCA GAT GTG TAT AAG AGA CAG GTC CTG AGC CTG TTT TGT GTC (SEQ ID NO: 31) | A |
| F32 | TCG TCG GCA GCG TCA GAT GTG TAT AAG AGA CAG CTC AAT CCC TGA CCC TGG CT (SEQ ID NO: 32) | A |
| F33 | TCG TCG GCA GCG TCA GAT GTG TAT AAG AGA CAG GTG GAG CCT CTT ACA CCC AG (SEQ ID NO: 33) | A |
| F34 | TCG TCG GCA GCG TCA GAT GTG TAT AAG AGA CAG CCA CAC TGA CGT GCC TCT CC (SEQ ID NO: 34) | A |
| F35 | TCG TCG GCA GCG TCA GAT GTG TAT AAG AGA CAG CTA CTT GGA GGA CCG TCG C (SEQ ID NO: 35) | A |

TABLE 15-continued

Primers for Pool A and B

| Primer | Sequence | Pool |
|---|---|---|
| F36 | TCG TCG GCA GCG TCA GAT GTG TAT AAG AGA CAG TCT ATC ATG GCT AAA TGC TGA CTT (SEQ ID NO: 36) | A |
| F37 | TCG TCG GCA GCG TCA GAT GTG TAT AAG AGA CAG CTG AAT CCT CCC CCA GCT G (SEQ ID NO: 37) | A |
| F38 | TCG TCG GCA GCG TCA GAT GTG TAT AAG AGA CAG CTC TGG TTT CTG GTG GGA CC (SEQ ID NO: 38) | B |
| F39 | TCG TCG GCA GCG TCA GAT GTG TAT AAG AGA CAG CCA CCC ACC CCT TTG AAA GA (SEQ ID NO: 39) | B |
| F40 | TCG TCG GCA GCG TCA GAT GTG TAT AAG AGA CAG TAC ACA GAG GAA GCC TTC GC (SEQ ID NO: 40) | B |
| F41 | TCG TCG GCA GCG TCA GAT GTG TAT AAG AGA CAG GAG ACA GGA TCA GGT CAG CG (SEQ ID NO: 41) | B |
| F42 | TCG TCG GCA GCG TCA GAT GTG TAT AAG AGA CAG TGG CCT TCT CCT TTA CCC CT (SEQ ID NO: 42) | B |
| F43 | TCG TCG GCA GCG TCA GAT GTG TAT AAG AGA CAG ACC ACA GTT GCA CAA TAT CCT (SEQ ID NO: 43) | B |
| F44 | TCG TCG GCA GCG TCA GAT GTG TAT AAG AGA CAG TGC AGA TCC TCA GTT TGT GGT (SEQ ID NO: 44) | B |
| F45 | TCG TCG GCA GCG TCA GAT GTG TAT AAG AGA CAG CCC ACC CAG CTC TCA ACA TT (SEQ ID NO: 45) | B |
| F46 | TCG TCG GCA GCG TCA GAT GTG TAT AAG AGA CAG AAC ACA CAC AGG AAG CCC TC (SEQ ID NO: 46) | B |
| F47 | TCG TCG GCA GCG TCA GAT GTG TAT AAG AGA CAG CTA TCC TGG CTG TGT CCT GG (SEQ ID NO: 47) | B |
| F48 | TCG TCG GCA GCG TCA GAT GTG TAT AAG AGA CAG AGG TCA GTG GAT CCC CTC TC (SEQ ID NO: 48) | B |
| F49 | TCG TCG GCA GCG TCA GAT GTG TAT AAG AGA CAG GCA CGG TAA TGC TGC TCA TG (SEQ ID NO: 49) | B |
| F50 | TCG TCG GCA GCG TCA GAT GTG TAT AAG AGA CAG ATG TCA GTC TGG TGT GGC AG (SEQ ID NO: 50) | B |
| F51 | TCG TCG GCA GCG TCA GAT GTG TAT AAG AGA CAG CAA GTT GGA AAT TTC TGG GCC A (SEQ ID NO: 51) | B |
| F52 | TCG TCG GCA GCG TCA GAT GTG TAT AAG AGA CAG GGA AAA TGA CAA AGA ACA GCT CA (SEQ ID NO: 52) | B |
| F53 | TCG TCG GCA GCG TCA GAT GTG TAT AAG AGA CAG GGC ACC ATC TCA CAA TTG CC (SEQ ID NO: 53) | B |
| F54 | TCG TCG GCA GCG TCA GAT GTG TAT AAG AGA CAG ACT GAT GGG ACC CAC TCC AT (SEQ ID NO: 54) | B |
| F55 | TCG TCG GCA GCG TCA GAT GTG TAT AAG AGA CAG TCC CTA GGT TTT GGT AAA GAT CCT (SEQ ID NO: 55) | B |
| F56 | TCG TCG GCA GCG TCA GAT GTG TAT AAG AGA CAG AGA GAG GCC TTG GGA CTG AT (SEQ ID NO: 56) | B |
| F57 | TCG TCG GCA GCG TCA GAT GTG TAT AAG AGA CAG GTA CCC AGA CTG ACC ACT GC (SEQ ID NO: 57) | B |
| F58 | TCG TCG GCA GCG TCA GAT GTG TAT AAG AGA CAG AGT TAT GAT TTT GCA GAA AAC AGA TCT (SEQ ID NO: 58) | B |
| F59 | TCG TCG GCA GCG TCA GAT GTG TAT AAG AGA CAG CAT TCT GCT GGT CGT GGT CT (SEQ ID NO: 59) | B |
| F60 | TCG TCG GCA GCG TCA GAT GTG TAT AAG AGA CAG GCT GAG GTG ACC CTT GTC TC (SEQ ID NO: 60) | B |
| F61 | TCG TCG GCA GCG TCA GAT GTG TAT AAG AGA CAG GCA TCT GCC TCA CCT CCA C (SEQ ID NO: 61) | B |
| F62 | TCG TCG GCA GCG TCA GAT GTG TAT AAG AGA CAG CCT CAC AGC AGG GTC TTC TC (SEQ ID NO: 62) | B |
| F63 | TCG TCG GCA GCG TCA GAT GTG TAT AAG AGA CAG TCT TCA ACC GTC CTT GGA AAA (SEQ ID NO: 63) | B |
| F64 | TCG TCG GCA GCG TCA GAT GTG TAT AAG AGA CAG TTC CAT GCA GTG TGT CCA CC (SEQ ID NO: 64) | B |
| F65 | TCG TCG GCA GCG TCA GAT GTG TAT AAG AGA CAG CTC TGA GCC CTC TTT CCA AAC T (SEQ ID NO: 65) | B |
| F66 | TCG TCG GCA GCG TCA GAT GTG TAT AAG AGA CAG GCA GCT CCG CCA CT (SEQ ID NO: 66) | B |
| F67 | TCG TCG GCA GCG TCA GAT GTG TAT AAG AGA CAG CAT GAG CTC CAG CAG GAT GA (SEQ ID NO: 67) | B |
| F68 | TCG TCG GCA GCG TCA GAT GTG TAT AAG AGA CAG ACT GAG AGG AGA AGA CTG TGT G (SEQ ID NO: 68) | B |
| F69 | TCG TCG GCA GCG TCA GAT GTG TAT AAG AGA CAG GCA AAT GGC CAC TGT GAA CA (SEQ ID NO: 69) | B |
| F70 | TCG TCG GCA GCG TCA GAT GTG TAT AAG AGA CAG CCT GGA TAC CTC TGG GCC ATA (SEQ ID NO: 70) | B |
| F71 | TCG TCG GCA GCG TCA GAT GTG TAT AAG AGA CAG ATA GGG CAG AGA AGG AGC AC (SEQ ID NO: 71) | B |

TABLE 15-continued

Primers for Pool A and B

| Primer | Sequence | Pool |
|---|---|---|
| F72 | TCG TCG GCA GCG TCA GAT GTG TAT AAG AGA CAG GCT TGG ACT GCA CAC AAC AG (SEQ ID NO: 72) | B |
| F73 | TCG TCG GCA GCG TCA GAT GTG TAT AAG AGA CAG GGT CCC TTC TGG CCT AGT AGA (SEQ ID NO: 73) | B |
| R1 | GTC TCG TGG GCT CGG AGA TGT GTA TAA GAG ACA GAG GGA GCA GAT TAA GCG AGT (SEQ ID NO: 74) | A |
| R2 | GTC TCG TGG GCT CGG AGA TGT GTA TAA GAG ACA GTG GGC AAA CTT GTG GTA GCA (SEQ ID NO: 75) | A |
| R3 | GTC TCG TGG GCT CGG AGA TGT GTA TAA GAG ACA GTT CCG CCA CTG AAC ATT GGA (SEQ ID NO: 76) | A |
| R4 | GTC TCG TGG GCT CGG AGA TGT GTA TAA GAG ACA GGC TGC CCA TGA GTT AGA GGA (SEQ ID NO: 77) | A |
| R5 | GTC TCG TGG GCT CGG AGA TGT GTA TAA GAG ACA GTT CAA AGG TGT CAG CCA GCA (SEQ ID NO: 78) | A |
| R6 | GTC TCG TGG GCT CGG AGA TGT GTA TAA GAG ACA GCC AGA CTG TGT TTC TCC CTT CT (SEQ ID NO: 79) | A |
| R7 | GTC TCG TGG GCT CGG AGA TGT GTA TAA GAG ACA GGG CCT GCT GAA AAT GAC TGA A (SEQ ID NO: 80) | A |
| R8 | GTC TCG TGG GCT CGG AGA TGT GTA TAA GAG ACA GAG GGT CTG ACG GGT AGA GTG (SEQ ID NO: 81) | A |
| R9 | GTC TCG TGG GCT CGG AGA TGT GTA TAA GAG ACA GTC ACC TTT CTG GCC ATG ACC (SEQ ID NO: 82) | A |
| R10 | GTC TCG TGG GCT CGG AGA TGT GTA TAA GAG ACA GTC GCT CTT GTT GCT TCC CA (SEQ ID NO: 83) | A |
| R11 | GTC TCG TGG GCT CGG AGA TGT GTA TAA GAG ACA GAC CTT GCC GTA AGA GCC TTC (SEQ ID NO: 84) | A |
| R12 | GTC TCG TGG GCT CGG AGA TGT GTA TAA GAG ACA GGG ATG AGG CTC CCA CCT TTC (SEQ ID NO: 85) | A |
| R13 | GTC TCG TGG GCT CGG AGA TGT GTA TAA GAG ACA GGC AGA AGC TGT CCT TGT GC (SEQ ID NO: 86) | A |
| R14 | GTC TCG TGG GCT CGG AGA TGT GTA TAA GAG ACA GCT CTC CCC TTG CAG CTG ATC (SEQ ID NO: 87) | A |
| R15 | GTC TCG TGG GCT CGG AGA TGT GTA TAA GAG ACA GGG CCA GAT GGA GTC TCC CTA (SEQ ID NO: 88) | A |
| R16 | GTC TCG TGG GCT CGG AGA TGT GTA TAA GAG ACA GAC ATT GCT GCC AGA AAC TGC (SEQ ID NO: 89) | A |
| R17 | GTC TCG TGG GCT CGG AGA TGT GTA TAA GAG ACA GTT GGC TTG CGG ACT CTG TAG (SEQ ID NO: 90) | A |
| R18 | GTC TCG TGG GCT CGG AGA TGT GTA TAA GAG ACA GTC CTC TTC TCC AGG ATT GCC (SEQ ID NO: 91) | A |
| R19 | GTC TCG TGG GCT CGG AGA TGT GTA TAA GAG ACA GAG TGC AGT GTG GAA TCC AGA (SEQ ID NO: 92) | A |
| R20 | GTC TCG TGG GCT CGG AGA TGT GTA TAA GAG ACA GGT GAC ATG AAA GCC CCT GT (SEQ ID NO: 93) | A |
| R21 | GTC TCG TGG GCT CGG AGA TGT GTA TAA GAG ACA GTT GGA CAC GGC TTT ACC TCC (SEQ ID NO: 94) | A |
| R22 | GTC TCG TGG GCT CGG AGA TGT GTA TAA GAG ACA GGC AGA GAA TGG GTA CTC ACG T (SEQ ID NO: 95) | A |
| R23 | GTC TCG TGG GCT CGG AGA TGT GTA TAA GAG ACA GCA GTG GCT TTG GTC CGT CT (SEQ ID NO: 96) | A |
| R24 | GTC TCG TGG GCT CGG AGA TGT GTA TAA GAG ACA GTG GAT TGT GGC ACA GAG ATT CT (SEQ ID NO: 97) | A |
| R25 | GTC TCG TGG GCT CGG AGA TGT GTA TAA GAG ACA GCT TCA CTG GCA GCT TTG CAC (SEQ ID NO: 98) | A |
| R26 | GTC TCG TGG GCT CGG AGA TGT GTA TAA GAG ACA GAG ACG GGA CTC GAG TGA TGA (SEQ ID NO: 99) | A |
| R27 | GTC TCG TGG GCT CGG AGA TGT GTA TAA GAG ACA GAT GCT GGC ACC ATC TGA CG (SEQ ID NO: 100) | A |
| R28 | GTC TCG TGG GCT CGG AGA TGT GTA TAA GAG ACA GCC TTC CTC CTT CCT CAG TGC (SEQ ID NO: 101) | A |
| R29 | GTC TCG TGG GCT CGG AGA TGT GTA TAA GAG ACA GAA CCT TGC AGA ATG TCG ATG (SEQ ID NO: 102) | A |
| R30 | GTC TCG TGG GCT CGG AGA TGT GTA TAA GAG ACA GTT CCG GAA AGT CCA CGC TC (SEQ ID NO: 103) | A |
| R31 | GTC TCG TGG GCT CGG AGA TGT GTA TAA GAG ACA GCA AAG TTG TGG ACA GGT TTT GA (SEQ ID NO: 104) | A |
| R32 | GTC TCG TGG GCT CGG AGA TGT GTA TAA GAG ACA GCA GTC TCC GCA TCG TGT ACT (SEQ ID NO: 105) | A |
| R33 | GTC TCG TGG GCT CGG AGA TGT GTA TAA GAG ACA GCA CCA GAC CAT GAG AGG CC (SEQ ID NO: 106) | A |
| R34 | GTC TCG TGG GCT CGG AGA TGT GTA TAA GAG ACA GGA CAT AGT CCA GGA GGC AGC (SEQ ID NO: 107) | A |

TABLE 15-continued

Primers for Pool A and B

| Primer | Sequence | Pool |
|---|---|---|
| R35 | GTC TCG TGG GCT CGG AGA TGT GTA TAA GAG ACA GGC TGA CCT AAA GCC ACC TCC (SEQ ID NO: 108) | A |
| R36 | GTC TCG TGG GCT CGG AGA TGT GTA TAA GAG ACA GTT TTC AGC CAC AGG AAA AAC CC (SEQ ID NO: 109) | A |
| R37 | GTC TCG TGG GCT CGG AGA TGT GTA TAA GAG ACA GTT TCA CCC GCA GCC TAG TG (SEQ ID NO: 110) | A |
| R38 | GTC TCG TGG GCT CGG AGA TGT GTA TAA GAG ACA GTG GAT CTC TTC ATG CAC CGG (SEQ ID NO: 111) | B |
| R39 | GTC TCG TGG GCT CGG AGA TGT GTA TAA GAG ACA GGC CAG CAT GAT GAG ACA GGT (SEQ ID NO: 112) | B |
| R40 | GTC TCG TGG GCT CGG AGA TGT GTA TAA GAG ACA GTT GAA CTT CCC TCC CTC CCT (SEQ ID NO: 113) | B |
| R41 | GTC TCG TGG GCT CGG AGA TGT GTA TAA GAG ACA GAC AAA CTG GTG GTG GTT GGA (SEQ ID NO: 114) | B |
| R42 | GTC TCG TGG GCT CGG AGA TGT GTA TAA GAG ACA GCT CCA CCC CAA GAG AGC AAC (SEQ ID NO: 115) | B |
| R43 | GTC TCG TGG GCT CGG AGA TGT GTA TAA GAG ACA GAT CTA GGG CCT CTT GTG CCT (SEQ ID NO: 116) | B |
| R44 | GTC TCG TGG GCT CGG AGA TGT GTA TAA GAG ACA GCA CAC ACA GGT AAC GGC TGA (SEQ ID NO: 117) | B |
| R45 | GTC TCG TGG GCT CGG AGA TGT GTA TAA GAG ACA GTC ATC GAG ATT TAG CAG CCA GA (SEQ ID NO: 118) | B |
| R46 | GTC TCG TGG GCT CGG AGA TGT GTA TAA GAG ACA GAG CAG GTG GTC ATT GAT GGG (SEQ ID NO: 119) | B |
| R47 | GTC TCG TGG GCT CGG AGA TGT GTA TAA GAG ACA GTA TAA GCT GGT GGT GGT GGG (SEQ ID NO: 120) | B |
| R48 | GTC TCG TGG GCT CGG AGA TGT GTA TAA GAG ACA GCC TCA CAG AGT TCA AGC TGA AG (SEQ ID NO: 121) | B |
| R49 | GTC TCG TGG GCT CGG AGA TGT GTA TAA GAG ACA GCC TCT GCT GTC ACC TCT TGG (SEQ ID NO: 122) | B |
| R50 | GTC TCG TGG GCT CGG AGA TGT GTA TAA GAG ACA GGG CGA CGA GAA ACA TGA TG (SEQ ID NO: 123) | B |
| R51 | GTC TCG TGG GCT CGG AGA TGT GTA TAA GAG ACA GTG CAA AAA TAT CCC CCG GCT (SEQ ID NO: 124) | B |
| R52 | GTC TCG TGG GCT CGG AGA TGT GTA TAA GAG ACA GAG CAC TTA CCT GTG ACT CCA (SEQ ID NO: 125) | B |
| R53 | GTC TCG TGG GCT CGG AGA TGT GTA TAA GAG ACA GGA GGT TCA GAG CCA TGG ACC (SEQ ID NO: 126) | B |
| R54 | GTC TCG TGG GCT CGG AGA TGT GTA TAA GAG ACA GAC TCT TCA TAA TGC TTG CTC TGA (SEQ ID NO: 127) | B |
| R55 | GTC TCG TGG GCT CGG AGA TGT GTA TAA GAG ACA GAA TCC CAG AGT GCT GTG CTG (SEQ ID NO: 128) | B |
| R56 | GTC TCG TGG GCT CGG AGA TGT GTA TAA GAG ACA GCC CTC CTC CCT TCC CAA GTA (SEQ ID NO: 129) | B |
| R57 | GTC TCG TGG GCT CGG AGA TGT GTA TAA GAG ACA GAC CAG ATC AGG GGC GAA GTA (SEQ ID NO: 130) | B |
| R58 | GTC TCG TGG GCT CGG AGA TGT GTA TAA GAG ACA GAC ACA AAA CAG GCT CAG GAC T (SEQ ID NO: 131) | B |
| R59 | GTC TCG TGG GCT CGG AGA TGT GTA TAA GAG ACA GTG GGA GGA CTT CAC CCC G (SEQ ID NO: 132) | B |
| R60 | GTC TCG TGG GCT CGG AGA TGT GTA TAA GAG ACA GAC CTT ACC TTA TAC ACC GTG CC (SEQ ID NO: 133) | B |
| R61 | GTC TCG TGG GCT CGG AGA TGT GTA TAA GAG ACA GCA TGT GAG GAT CCT GGC TCC (SEQ ID NO: 134) | B |
| R62 | GTC TCG TGG GCT CGG AGA TGT GTA TAA GAG ACA GTC TTT CTC TTC CGC ACC CAG (SEQ ID NO: 135) | B |
| R63 | GTC TCG TGG GCT CGG AGA TGT GTA TAA GAG ACA GAC TGT AAT GAC TGT GTT CTT AAG GT (SEQ ID NO: 136) | B |
| R64 | GTC TCG TGG GCT CGG AGA TGT GTA TAA GAG ACA GAG GAC GTA CAC TGC CTT TCG (SEQ ID NO: 137) | B |
| R65 | GTC TCG TGG GCT CGG AGA TGT GTA TAA GAG ACA GCC ACC TGG AAC TTG GTC TCA (SEQ ID NO: 138) | B |
| R66 | GTC TCG TGG GCT CGG AGA TGT GTA TAA GAG ACA GGG CTC TAC ACA AGC TTC CTT (SEQ ID NO: 139) | B |
| R67 | GTC TCG TGG GCT CGG AGA TGT GTA TAA GAG ACA GTT ACA TCC CTC TCT GCT CTG C (SEQ ID NO: 140) | B |
| R68 | GTC TCG TGG GCT CGG AGA TGT GTA TAA GAG ACA GTC AGG TCC TCA AAG CAC CAG (SEQ ID NO: 141) | B |
| R69 | GTC TCG TGG GCT CGG AGA TGT GTA TAA GAG ACA GAA GGA GAG AGT TGT GAG GCC A (SEQ ID NO: 142) | B |
| R70 | GTC TCG TGG GCT CGG AGA TGT GTA TAA GAG ACA GTT TCG GCC CAA CCA GTA TCC (SEQ ID NO: 143) | B |

TABLE 15-continued

Primers for Pool A and B

| Primer | Sequence | Pool |
|---|---|---|
| R71 | GTC TCG TGG GCT CGG AGA TGT GTA TAA GAG ACA GAA TGG AGC CAC TGA ACT GCA (SEQ ID NO: 144) | B |
| R72 | GTC TCG TGG GCT CGG AGA TGT GTA TAA GAG ACA GGC TGG GAC CTG TTC ACT TGT (SEQ ID NO: 145) | B |
| R73 | GTC TCG TGG GCT CGG AGA TGT GTA TAA GAG ACA GCT ACC ATG TCT CCC CAG GCT (SEQ ID NO: 146) | B |

TABLE 16

Hotspots and exons covered in amplicons.

| Gene | Mutation(s) |
|---|---|
| AKT1 | E17K |
| ALK | T1151_L1152insT, L1152R, C1156Y, F1174, L1196M, G1269, R1275 |
| AR | W741C, H875Y, F877, T878A |
| BRAF | Q201X, Y472, G469, G466, D594, G596, L597, V600 |
| CDKN2A | R58* |
| CTNNB1 | S37, T41, S45 |
| EGFR | Exons 18, 19, 20, 21 |
| ERBB2 | Exon 20, G309E, S310 |
| ESR1 | L536, Y537, D538 |
| EZH2 | Y646 |
| FGFR1 | N546, K656E |
| FGFR2 | N549K, S252W, P253R, K659 |
| GNA11 | Q209L |
| GNAQ | Q209L |
| GNAS | R201H |
| HRAS | G12V, G13R, Q61 |
| IDH1 | R132H |
| IDH2 | R172, R140 |
| JAK1 | V658F, S703I |
| KIT | D816V, K642E, V654A, W557, V559, L576P |
| KRAS | G13, G12, Q61, K117N, A146T |
| MEK1 | Q56, K57X, K59del, D67X, P387X |
| MEK2 | F57X, Q60X, K61X, L119X |
| MET | Exons 13, 18, Y1253D |
| NRAS | G13, G12, Q61, K117N, A146 |
| PDGFRA | D842V |
| PIK3CA | M1043, N1044 H1047, G1049, E542, E545, D549 |
| PTEN | R130Q, R173C, R233* |
| RET | C634, M918T |
| STK11 | Q37*, P281L, F354L |

Locus specific primers included Nextera XT (Illumina) common sequences so that after PCR Ampure XP bead cleanup library construction was performed using the Nextera XT barcode kit. The indexed adapters were ligated to the amplified sequences through 8 cycles of PCR. After library construction samples were again purified using the AMPure XP Beads, quantitated with Qubit and analyzed using the Agilent Bioanalyzer. Samples were pooled and diluted to 12.5 pM prior to sequencing on the MiSeq (Illumina) using the 300 cycle v2 kit for paired end 150 bp reads. The pooling strategy was such that 20 patients and a positive and negative control were included for each run.

Primer Panel CG001.2 For Targeted Amplification of Somatic Aberrations in Cancer A targeted oligonucleotide DNA sequence primer panel CG001.v2, (Table 15), consisting of 73 PCR primer pairs was designed using primer3[3] to amplify target genomic regions in the human genome (hg19). The genomic regions used for primer design encompass genomic regions 200 bp upstream and downstream of the targeted regions. Selection of the primer pairs used in the panel involved the design of primer groups of a minimum of 45 primer pairs for each target region using the following primer3 settings; minimum size:18, optimal size:20, maximum size:27, product size range:100-249, minimum temp:57, optimal temp: 60, maximum temp:63. Primers pairs meeting any of the following criteria were excluded from the design groups: greater than three consecutive guanine's in either the forward or reverse primer sequences, primers aligning to genomic target regions having snps with 1000 genome allele prevalence >0.005, primer pairs amplifying off target genomic regions determined using NCBI Blast[4].

Primer pairs in each of the primer groups were sequentially tested for compatibility with existing primer pairs in one of two pools. Each primer pair was tested for primer dimerization with existing primer pairs defined as an alignment of greater than four bases with >80% matching bases. Once a compatible primer pair was identified, the primer pair was added to the pool and primer pair testing for the primer group was terminated. Testing of the primer pairs in the next primer group would then commence. The final primer panel created using this process consisted of one selected compatible primer pair from each of the primer groups split over two pools. The PCR amplification performance of each primer pair in each panel was assessed and primer pairs that failed to amplify genomic sequence were redesigned using primer3 and tested for compatibility with the existing pools.

Informatic Analysis of Sequences from Performing CG001.v2

Paired reads from target amplicons generated by the Illumina MiSeq were aligned to the reference genome hg19 using bwa with the BWA-mem algorithm[5]. Further processing and filtering of aligned reads was performed using SAMtools[6] and bamUtils[7]. Only aligned reads meeting the following criteria were used in further analysis; on target with the expected read length, reads with less than 5 mismatches and reads with soft clipping of less than 7 bp. The filtered alignments were then used for SNVs and indel identification using MutationSeq[2] and strelka[8] tools respectively. MutationSeq uses a feature-based classifier to assess the probability of a somatic mutation at any given position and requires sequencing data from matched tumour-normal pairs. Strelka is based on a Bayesian approach and requires tumour-normal pairs as well. Since matched normal samples are not available, variant detection was performed using the cell line derived from normal B-lymphocytes of a healthy female individual as a normal reference (NA01953, Coriell Biorepositories). Detection of SNVs with high confidence required a target minimum depth of 1000× and MutationSeq probability score of >=0.9. Indel detection required a minimum target depth of 1000× and a Quality Score of at least 30. The Quantitative Multiplex DNA Reference Standard (Horizon Diagnostics) was used as a positive control for detection of SNVs and indels at a wide range of allelic frequencies (1-33.5%). The Pearson's correlation of predicted vs reported allelic frequencies for the positive control of at least 0.9 served as an indication of a successful variant detection. The effect of the detected high confidence SNVs and indels was annotated using SnpEff[9] and the UCSC known genes database. The analysis workflow is shown in FIG. 2, with the extension including the workflow of FIG. 22 which incorporates the disclosed methods of codeword analysis to the mutation calling.

REFERENCES

1) Goya, R., Sun, M. G., Morin, R. D., GG, L., Ha, G., Wiegand, K. C., et al. (2010). *SNVMix: predicting single nucleotide variants from next-generation sequencing of tumors*. Bioinformatics (Oxford, England), 26(6), 730-736.
2) Ding J1, Bashashati A, Roth A, Oloumi A, Tse K, Zeng T, Haffori G, Hirst M, Marra M A, Condon A, Aparicio S, Shah S P. *Feature-based classifiers for somatic mutation detection in tumour-normal paired sequencing data*. Bioinformatics. 2012 Jan. 15; 28(2):167-75.
3) Untergasser A, Cutcutache I, Koressaar T, Ye J, Faircloth B C, Remm M and Rozen S G. (2012), *Primer3—new capabilities and interfaces*. Nucleic Acids Res. 40(15): e115.
4) Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", *Nucleic Acids Res*. 25:3389-3402.
5) Li H. *Aligning sequence reads, clone sequences and assembly contigs with BWA-MEM*. (2013). arXiv: 1303.3997v1 [q-bio.GN]
6) Li H1, Handsaker B, Wysoker A, Fennell T, Ruan J, Homer N, Marth G, Abecasis G, Durbin R; 1000 Genome Project Data Processing Subgroup. *The Sequence Alignment/Map format and SAMtools*. Bioinformatics. 2009 Aug. 15; 25(16):2078-9.
7) Breese M R1, Liu Y. *NGSUtils: a software suite for analyzing and manipulating next-generation sequencing datasets*. Bioinformatics. 2013 Feb. 15; 29(4):494-6.
8) Saunders C T1, Wong W S, Swamy S, Becq J, Murray L J, Cheetham R K. *Strelka: accurate somatic small-variant calling from sequenced tumor-normal sample pairs*. Bioinformatics. 2012 Jul. 15; 28(14):1811-7.
9) Cingolani P1, Platts A, Wang le L, Coon M, Nguyen T, Wang L, Land S J, Lu X, Ruden D M. *A program for annotating and predicting the effects of single nucleotide polymorphisms, SnpEff: SNPs in the genome of Drosophila melanogaster strain w1118; iso-2; iso-*3. Fly (Austin). 2012 April-June; 6(2):80-92.
10) Tulpan D C and Hoos H H (2003). *Hybrid randomized neighbourhoods improve stochastic local search for DNA code design*. Lecture Notes in Computer Science 2671: 418:433.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method of determining the complexity of a nucleic acid template, or of identifying a true sequence variant, comprising:
   i) providing a nucleic acid template;
   ii) providing a plurality of primer pairs, comprising a first primer and a second primer, wherein the first primer comprises a sequence complementary to a portion of the nucleic acid template, and the second primer comprises a sequence complementary to a portion of the complement of the nucleic acid template;
   iii) attaching a codeword to the 5' end of the first primer, the 5' end of the second primer, or both, to form a codeword-primer molecule, or to the nucleic acid template to form a codeword-template molecule;
   iv) performing an amplification reaction with the paired codeword-primer molecules and the nucleic acid template or with the primer pairs and the codeword-template molecule for a defined number of cycles to obtain an amplification reaction product;
   v) obtaining the sequence of the amplification reaction product at the end of each cycle, at the end of the defined number of cycles, or at an intermediate number of cycles;
   vi) determining the abundance of each codeword present in the amplification reaction product at the end of each cycle, at the end of the defined number of cycles, or at an intermediate number of cycles;
   vii) calculating an observed codeword entropy of each cycle after step vi); and
   viii) comparing the observed codeword entropy to an estimated codeword entropy, to determine the complexity of the nucleic acid template; or
   ix) performing a supervised classification method based on the results of steps vi) and vii), to identify the true sequence variant.

2. The method of claim 1 wherein the true sequence variant is a low prevalence sequence variant.

3. The method of claim 1 wherein the nucleic acid template is a DNA template.

4. The method of claim 1 wherein the codeword-primer molecule or the primer is further attached to an adapter sequence.

5. The method of claim 1 wherein a different codeword is attached to each primer in the primer pair or the same codeword is attached to each primer in the primer pair.

6. The method of claim 1 wherein the codewords are attached to the nucleic acid template at random.

7. The method of claim 1 wherein the observed codeword entropy is calculated by Shannon entropy, the Simpson index, or any other diversity index.

8. The method of claim 1 wherein the codewords are present in a non-uniform pool or are present in a balanced pool.

9. The method of claim 1 further comprising determining one or more of amplification process, contamination, sample identity mismatch, or codeword pool imbalance.

* * * * *

SEQUENCE LISTING

```
<160> NUMBER OF SEQ ID NOS: 146

<210> SEQ ID NO 1
<211> LENGTH: 55
<212> TYPE: DNA
<213> ORGANISM: Artificial Sequence
<220> FEATURE:
<223> OTHER INFORMATION: Primer

<400> SEQUENCE: 1
tcgtcggcag cgtcagatgt gtataagaga cagtgctgaa agctgtacca tacct        55

<210> SEQ ID NO 2
<211> LENGTH: 53
<212> TYPE: DNA
<213> ORGANISM: Artificial Sequence
<220> FEATURE:
<223> OTHER INFORMATION: Primer

<400> SEQUENCE: 2
tcgtcggcag cgtcagatgt gtataagaga cagcagagca tacgcagcct gta          53

<210> SEQ ID NO 3
<211> LENGTH: 53
<212> TYPE: DNA
<213> ORGANISM: Artificial Sequence
<220> FEATURE:
<223> OTHER INFORMATION: Primer

<400> SEQUENCE: 3
tcgtcggcag cgtcagatgt gtataagaga cagtggctac gacccagtta cca          53

<210> SEQ ID NO 4
<211> LENGTH: 53
<212> TYPE: DNA
<213> ORGANISM: Artificial Sequence
```

-continued

```
<220> FEATURE:
<223> OTHER INFORMATION: Primer

<400> SEQUENCE: 4
tcgtcggcag cgtcagatgt gtataagaga cagctgtgtg caggctccaa gaa        53

<210> SEQ ID NO 5
<211> LENGTH: 53
<212> TYPE: DNA
<213> ORGANISM: Artificial Sequence
<220> FEATURE:
<223> OTHER INFORMATION: Primer

<400> SEQUENCE: 5
tcgtcggcag cgtcagatgt gtataagaga cagactctac gtctcctccg acc        53

<210> SEQ ID NO 6
<211> LENGTH: 53
<212> TYPE: DNA
<213> ORGANISM: Artificial Sequence
<220> FEATURE:
<223> OTHER INFORMATION: Primer

<400> SEQUENCE: 6
tcgtcggcag cgtcagatgt gtataagaga cagacaaaga aagccctccc cag        53

<210> SEQ ID NO 7
<211> LENGTH: 54
<212> TYPE: DNA
<213> ORGANISM: Artificial Sequence
<220> FEATURE:
<223> OTHER INFORMATION: Primer

<400> SEQUENCE: 7
tcgtcggcag cgtcagatgt gtataagaga cagggtcctg caccagtaat atgc       54

<210> SEQ ID NO 8
<211> LENGTH: 53
<212> TYPE: DNA
<213> ORGANISM: Artificial Sequence
<220> FEATURE:
<223> OTHER INFORMATION: Primer

<400> SEQUENCE: 8
tcgtcggcag cgtcagatgt gtataagaga cagtacgcgc cacagagaag ttg        53

<210> SEQ ID NO 9
<211> LENGTH: 53
<212> TYPE: DNA
<213> ORGANISM: Artificial Sequence
<220> FEATURE:
<223> OTHER INFORMATION: Primer

<400> SEQUENCE: 9
tcgtcggcag cgtcagatgt gtataagaga cagcttgtgc tccccacttt gga        53

<210> SEQ ID NO 10
<211> LENGTH: 53
<212> TYPE: DNA
<213> ORGANISM: Artificial Sequence
<220> FEATURE:
<223> OTHER INFORMATION: Primer

<400> SEQUENCE: 10
tcgtcggcag cgtcagatgt gtataagaga cagacaccac gtcctctcgt ttc        53
```

```
<210> SEQ ID NO 11
<211> LENGTH: 53
<212> TYPE: DNA
<213> ORGANISM: Artificial Sequence
<220> FEATURE:
<223> OTHER INFORMATION: Primer

<400> SEQUENCE: 11
tcgtcggcag cgtcagatgt gtataagaga cagggtgggt atggacacgt tca      53

<210> SEQ ID NO 12
<211> LENGTH: 53
<212> TYPE: DNA
<213> ORGANISM: Artificial Sequence
<220> FEATURE:
<223> OTHER INFORMATION: Primer

<400> SEQUENCE: 12
tcgtcggcag cgtcagatgt gtataagaga cagagctaca acatcaccac ggg      53

<210> SEQ ID NO 13
<211> LENGTH: 53
<212> TYPE: DNA
<213> ORGANISM: Artificial Sequence
<220> FEATURE:
<223> OTHER INFORMATION: Primer

<400> SEQUENCE: 13
tcgtcggcag cgtcagatgt gtataagaga cagcatgact gtggtgccgt act      53

<210> SEQ ID NO 14
<211> LENGTH: 53
<212> TYPE: DNA
<213> ORGANISM: Artificial Sequence
<220> FEATURE:
<223> OTHER INFORMATION: Primer

<400> SEQUENCE: 14
tcgtcggcag cgtcagatgt gtataagaga caggacgcac tcaccatgtg ttc      53

<210> SEQ ID NO 15
<211> LENGTH: 53
<212> TYPE: DNA
<213> ORGANISM: Artificial Sequence
<220> FEATURE:
<223> OTHER INFORMATION: Primer

<400> SEQUENCE: 15
tcgtcggcag cgtcagatgt gtataagaga cagagggtct gtgctggact ttg      53

<210> SEQ ID NO 16
<211> LENGTH: 53
<212> TYPE: DNA
<213> ORGANISM: Artificial Sequence
<220> FEATURE:
<223> OTHER INFORMATION: Primer

<400> SEQUENCE: 16
tcgtcggcag cgtcagatgt gtataagaga cagtaaggga caagcagcca cac      53

<210> SEQ ID NO 17
<211> LENGTH: 53
<212> TYPE: DNA
<213> ORGANISM: Artificial Sequence
<220> FEATURE:
<223> OTHER INFORMATION: Primer
```

```
<400> SEQUENCE: 17
tcgtcggcag cgtcagatgt gtataagaga cagagggtgt ctctctgtgg ctt          53

<210> SEQ ID NO 18
<211> LENGTH: 53
<212> TYPE: DNA
<213> ORGANISM: Artificial Sequence
<220> FEATURE:
<223> OTHER INFORMATION: Primer

<400> SEQUENCE: 18
tcgtcggcag cgtcagatgt gtataagaga caggaaccag acagaaaagc ggc          53

<210> SEQ ID NO 19
<211> LENGTH: 53
<212> TYPE: DNA
<213> ORGANISM: Artificial Sequence
<220> FEATURE:
<223> OTHER INFORMATION: Primer

<400> SEQUENCE: 19
tcgtcggcag cgtcagatgt gtataagaga cagatgcttg gctctggaat gcc          53

<210> SEQ ID NO 20
<211> LENGTH: 53
<212> TYPE: DNA
<213> ORGANISM: Artificial Sequence
<220> FEATURE:
<223> OTHER INFORMATION: Primer

<400> SEQUENCE: 20
tcgtcggcag cgtcagatgt gtataagaga cagtctcccc acagaaaccc atg          53

<210> SEQ ID NO 21
<211> LENGTH: 53
<212> TYPE: DNA
<213> ORGANISM: Artificial Sequence
<220> FEATURE:
<223> OTHER INFORMATION: Primer

<400> SEQUENCE: 21
tcgtcggcag cgtcagatgt gtataagaga cagtgcgctt gacatcagtt tgc          53

<210> SEQ ID NO 22
<211> LENGTH: 53
<212> TYPE: DNA
<213> ORGANISM: Artificial Sequence
<220> FEATURE:
<223> OTHER INFORMATION: Primer

<400> SEQUENCE: 22
tcgtcggcag cgtcagatgt gtataagaga cagcagagac ttggcagcca gaa          53

<210> SEQ ID NO 23
<211> LENGTH: 53
<212> TYPE: DNA
<213> ORGANISM: Artificial Sequence
<220> FEATURE:
<223> OTHER INFORMATION: Primer

<400> SEQUENCE: 23
tcgtcggcag cgtcagatgt gtataagaga caggaagtgc aagaacgtgg tgc          53

<210> SEQ ID NO 24
```

<211> LENGTH: 58
<212> TYPE: DNA
<213> ORGANISM: Artificial Sequence
<220> FEATURE:
<223> OTHER INFORMATION: Primer

<400> SEQUENCE: 24
tcgtcggcag cgtcagatgt gtataagaga caggctttc taactctctt tgactgca    58

<210> SEQ ID NO 25
<211> LENGTH: 55
<212> TYPE: DNA
<213> ORGANISM: Artificial Sequence
<220> FEATURE:
<223> OTHER INFORMATION: Primer

<400> SEQUENCE: 25
tcgtcggcag cgtcagatgt gtataagaga cagtgtcctt tctgtaggct ggatg       55

<210> SEQ ID NO 26
<211> LENGTH: 54
<212> TYPE: DNA
<213> ORGANISM: Artificial Sequence
<220> FEATURE:
<223> OTHER INFORMATION: Primer

<400> SEQUENCE: 26
tcgtcggcag cgtcagatgt gtataagaga cagacttacc atgccacttt ccct        54

<210> SEQ ID NO 27
<211> LENGTH: 53
<212> TYPE: DNA
<213> ORGANISM: Artificial Sequence
<220> FEATURE:
<223> OTHER INFORMATION: Primer

<400> SEQUENCE: 27
tcgtcggcag cgtcagatgt gtataagaga cagaagtcca ggctgaaaag gca         53

<210> SEQ ID NO 28
<211> LENGTH: 53
<212> TYPE: DNA
<213> ORGANISM: Artificial Sequence
<220> FEATURE:
<223> OTHER INFORMATION: Primer

<400> SEQUENCE: 28
tcgtcggcag cgtcagatgt gtataagaga cagccccact ccttgcttct cag         53

<210> SEQ ID NO 29
<211> LENGTH: 54
<212> TYPE: DNA
<213> ORGANISM: Artificial Sequence
<220> FEATURE:
<223> OTHER INFORMATION: Primer

<400> SEQUENCE: 29
tcgtcggcag cgtcagatgt gtataagaga cagacctcat tgtctgactc cacg        54

<210> SEQ ID NO 30
<211> LENGTH: 53
<212> TYPE: DNA
<213> ORGANISM: Artificial Sequence
<220> FEATURE:
<223> OTHER INFORMATION: Primer

<400> SEQUENCE: 30
tcgtcggcag cgtcagatgt gtataagaga cagcacctcc ttgtcaaccc tgt            53

<210> SEQ ID NO 31
<211> LENGTH: 54
<212> TYPE: DNA
<213> ORGANISM: Artificial Sequence
<220> FEATURE:
<223> OTHER INFORMATION: Primer

<400> SEQUENCE: 31
tcgtcggcag cgtcagatgt gtataagaga caggtcctga gcctgttttg tgtc           54

<210> SEQ ID NO 32
<211> LENGTH: 53
<212> TYPE: DNA
<213> ORGANISM: Artificial Sequence
<220> FEATURE:
<223> OTHER INFORMATION: Primer

<400> SEQUENCE: 32
tcgtcggcag cgtcagatgt gtataagaga cagctcaatc cctgaccctg gct            53

<210> SEQ ID NO 33
<211> LENGTH: 53
<212> TYPE: DNA
<213> ORGANISM: Artificial Sequence
<220> FEATURE:
<223> OTHER INFORMATION: Primer

<400> SEQUENCE: 33
tcgtcggcag cgtcagatgt gtataagaga caggtggagc ctcttacacc cag            53

<210> SEQ ID NO 34
<211> LENGTH: 53
<212> TYPE: DNA
<213> ORGANISM: Artificial Sequence
<220> FEATURE:
<223> OTHER INFORMATION: Primer

<400> SEQUENCE: 34
tcgtcggcag cgtcagatgt gtataagaga cagccacact gacgtgcctc tcc            53

<210> SEQ ID NO 35
<211> LENGTH: 52
<212> TYPE: DNA
<213> ORGANISM: Artificial Sequence
<220> FEATURE:
<223> OTHER INFORMATION: Primer

<400> SEQUENCE: 35
tcgtcggcag cgtcagatgt gtataagaga cagctacttg gaggaccgtc gc             52

<210> SEQ ID NO 36
<211> LENGTH: 57
<212> TYPE: DNA
<213> ORGANISM: Artificial Sequence
<220> FEATURE:
<223> OTHER INFORMATION: Primer

<400> SEQUENCE: 36
tcgtcggcag cgtcagatgt gtataagaga cagtctatca tggctaaatg ctgactt        57

<210> SEQ ID NO 37
<211> LENGTH: 53
<212> TYPE: DNA

```
<213> ORGANISM: Artificial Sequence
<220> FEATURE:
<223> OTHER INFORMATION: Primer

<400> SEQUENCE: 37
tcgtcggcag cgtcagatgt gtataagaga cagctgaatc ctcccccaag ctg         53

<210> SEQ ID NO 38
<211> LENGTH: 53
<212> TYPE: DNA
<213> ORGANISM: Artificial Sequence
<220> FEATURE:
<223> OTHER INFORMATION: Primer

<400> SEQUENCE: 38
tcgtcggcag cgtcagatgt gtataagaga cagctctggt ttctggtggg acc         53

<210> SEQ ID NO 39
<211> LENGTH: 53
<212> TYPE: DNA
<213> ORGANISM: Artificial Sequence
<220> FEATURE:
<223> OTHER INFORMATION: Primer

<400> SEQUENCE: 39
tcgtcggcag cgtcagatgt gtataagaga cagccaccca cccctttgaa aga         53

<210> SEQ ID NO 40
<211> LENGTH: 53
<212> TYPE: DNA
<213> ORGANISM: Artificial Sequence
<220> FEATURE:
<223> OTHER INFORMATION: Primer

<400> SEQUENCE: 40
tcgtcggcag cgtcagatgt gtataagaga cagtacacag aggaagcctt cgc         53

<210> SEQ ID NO 41
<211> LENGTH: 53
<212> TYPE: DNA
<213> ORGANISM: Artificial Sequence
<220> FEATURE:
<223> OTHER INFORMATION: Primer

<400> SEQUENCE: 41
tcgtcggcag cgtcagatgt gtataagaga caggagacag gatcaggtca gcg         53

<210> SEQ ID NO 42
<211> LENGTH: 53
<212> TYPE: DNA
<213> ORGANISM: Artificial Sequence
<220> FEATURE:
<223> OTHER INFORMATION: Primer

<400> SEQUENCE: 42
tcgtcggcag cgtcagatgt gtataagaga cagtggcctt ctcctttacc cct         53

<210> SEQ ID NO 43
<211> LENGTH: 54
<212> TYPE: DNA
<213> ORGANISM: Artificial Sequence
<220> FEATURE:
<223> OTHER INFORMATION: Primer

<400> SEQUENCE: 43
tcgtcggcag cgtcagatgt gtataagaga cagaccacag ttgcacaata tcct        54
```

<210> SEQ ID NO 44
<211> LENGTH: 54
<212> TYPE: DNA
<213> ORGANISM: Artificial Sequence
<220> FEATURE:
<223> OTHER INFORMATION: Primer

<400> SEQUENCE: 44
tcgtcggcag cgtcagatgt gtataagaga cagtgcagat cctcagtttg tggt    54

<210> SEQ ID NO 45
<211> LENGTH: 53
<212> TYPE: DNA
<213> ORGANISM: Artificial Sequence
<220> FEATURE:
<223> OTHER INFORMATION: Primer

<400> SEQUENCE: 45
tcgtcggcag cgtcagatgt gtataagaga cagcccaccc agctctcaac att    53

<210> SEQ ID NO 46
<211> LENGTH: 53
<212> TYPE: DNA
<213> ORGANISM: Artificial Sequence
<220> FEATURE:
<223> OTHER INFORMATION: Primer

<400> SEQUENCE: 46
tcgtcggcag cgtcagatgt gtataagaga cagaacacac acaggaagcc ctc    53

<210> SEQ ID NO 47
<211> LENGTH: 53
<212> TYPE: DNA
<213> ORGANISM: Artificial Sequence
<220> FEATURE:
<223> OTHER INFORMATION: Primer

<400> SEQUENCE: 47
tcgtcggcag cgtcagatgt gtataagaga cagctatcct ggctgtgtcc tgg    53

<210> SEQ ID NO 48
<211> LENGTH: 53
<212> TYPE: DNA
<213> ORGANISM: Artificial Sequence
<220> FEATURE:
<223> OTHER INFORMATION: Primer

<400> SEQUENCE: 48
tcgtcggcag cgtcagatgt gtataagaga cagaggtcag tggatcccct ctc    53

<210> SEQ ID NO 49
<211> LENGTH: 53
<212> TYPE: DNA
<213> ORGANISM: Artificial Sequence
<220> FEATURE:
<223> OTHER INFORMATION: Primer

<400> SEQUENCE: 49
tcgtcggcag cgtcagatgt gtataagaga caggcacggt aatgctgctc atg    53

<210> SEQ ID NO 50
<211> LENGTH: 53
<212> TYPE: DNA
<213> ORGANISM: Artificial Sequence
<220> FEATURE:

<223> OTHER INFORMATION: Primer

<400> SEQUENCE: 50
tcgtcggcag cgtcagatgt gtataagaga cagatgtcag tctggtgtgg cag    53

<210> SEQ ID NO 51
<211> LENGTH: 55
<212> TYPE: DNA
<213> ORGANISM: Artificial Sequence
<220> FEATURE:
<223> OTHER INFORMATION: Primer

<400> SEQUENCE: 51
tcgtcggcag cgtcagatgt gtataagaga cagcaagttg gaaatttctg ggcca    55

<210> SEQ ID NO 52
<211> LENGTH: 56
<212> TYPE: DNA
<213> ORGANISM: Artificial Sequence
<220> FEATURE:
<223> OTHER INFORMATION: Primer

<400> SEQUENCE: 52
tcgtcggcag cgtcagatgt gtataagaga cagggaaaat gacaaagaac agctca    56

<210> SEQ ID NO 53
<211> LENGTH: 53
<212> TYPE: DNA
<213> ORGANISM: Artificial Sequence
<220> FEATURE:
<223> OTHER INFORMATION: Primer

<400> SEQUENCE: 53
tcgtcggcag cgtcagatgt gtataagaga cagggcacca tctcacaatt gcc    53

<210> SEQ ID NO 54
<211> LENGTH: 53
<212> TYPE: DNA
<213> ORGANISM: Artificial Sequence
<220> FEATURE:
<223> OTHER INFORMATION: Primer

<400> SEQUENCE: 54
tcgtcggcag cgtcagatgt gtataagaga cagactgatg ggacccactc cat    53

<210> SEQ ID NO 55
<211> LENGTH: 57
<212> TYPE: DNA
<213> ORGANISM: Artificial Sequence
<220> FEATURE:
<223> OTHER INFORMATION: Primer

<400> SEQUENCE: 55
tcgtcggcag cgtcagatgt gtataagaga cagtccctag gttttggtaa agatcct    57

<210> SEQ ID NO 56
<211> LENGTH: 53
<212> TYPE: DNA
<213> ORGANISM: Artificial Sequence
<220> FEATURE:
<223> OTHER INFORMATION: Primer

<400> SEQUENCE: 56
tcgtcggcag cgtcagatgt gtataagaga cagagagagg ccttgggact gat    53

```
<210> SEQ ID NO 57
<211> LENGTH: 53
<212> TYPE: DNA
<213> ORGANISM: Artificial Sequence
<220> FEATURE:
<223> OTHER INFORMATION: Primer

<400> SEQUENCE: 57
tcgtcggcag cgtcagatgt gtataagaga caggtaccca gactgaccac tgc          53

<210> SEQ ID NO 58
<211> LENGTH: 60
<212> TYPE: DNA
<213> ORGANISM: Artificial Sequence
<220> FEATURE:
<223> OTHER INFORMATION: Primer

<400> SEQUENCE: 58
tcgtcggcag cgtcagatgt gtataagaga cagagttatg attttgcaga aaacagatct   60

<210> SEQ ID NO 59
<211> LENGTH: 53
<212> TYPE: DNA
<213> ORGANISM: Artificial Sequence
<220> FEATURE:
<223> OTHER INFORMATION: Primer

<400> SEQUENCE: 59
tcgtcggcag cgtcagatgt gtataagaga cagcattctg ctggtcgtgg tct          53

<210> SEQ ID NO 60
<211> LENGTH: 53
<212> TYPE: DNA
<213> ORGANISM: Artificial Sequence
<220> FEATURE:
<223> OTHER INFORMATION: Primer

<400> SEQUENCE: 60
tcgtcggcag cgtcagatgt gtataagaga caggctgagg tgacccttgt ctc          53

<210> SEQ ID NO 61
<211> LENGTH: 52
<212> TYPE: DNA
<213> ORGANISM: Artificial Sequence
<220> FEATURE:
<223> OTHER INFORMATION: Primer

<400> SEQUENCE: 61
tcgtcggcag cgtcagatgt gtataagaga caggcatctg cctcacctcc ac           52

<210> SEQ ID NO 62
<211> LENGTH: 53
<212> TYPE: DNA
<213> ORGANISM: Artificial Sequence
<220> FEATURE:
<223> OTHER INFORMATION: Primer

<400> SEQUENCE: 62
tcgtcggcag cgtcagatgt gtataagaga cagcctcaca gcagggtctt ctc          53

<210> SEQ ID NO 63
<211> LENGTH: 54
<212> TYPE: DNA
<213> ORGANISM: Artificial Sequence
<220> FEATURE:
<223> OTHER INFORMATION: Primer
```

-continued

<400> SEQUENCE: 63
tcgtcggcag cgtcagatgt gtataagaga cagtcttcaa ccgtccttgg aaaa    54

<210> SEQ ID NO 64
<211> LENGTH: 53
<212> TYPE: DNA
<213> ORGANISM: Artificial Sequence
<220> FEATURE:
<223> OTHER INFORMATION: Primer

<400> SEQUENCE: 64
tcgtcggcag cgtcagatgt gtataagaga cagttccatg cagtgtgtcc acc    53

<210> SEQ ID NO 65
<211> LENGTH: 55
<212> TYPE: DNA
<213> ORGANISM: Artificial Sequence
<220> FEATURE:
<223> OTHER INFORMATION: Primer

<400> SEQUENCE: 65
tcgtcggcag cgtcagatgt gtataagaga cagctctgag ccctctttcc aaact    55

<210> SEQ ID NO 66
<211> LENGTH: 50
<212> TYPE: DNA
<213> ORGANISM: Artificial Sequence
<220> FEATURE:
<223> OTHER INFORMATION: Primer

<400> SEQUENCE: 66
tcgtcggcag cgtcagatgt gtataagaga caggcagcag ctccgccact    50

<210> SEQ ID NO 67
<211> LENGTH: 53
<212> TYPE: DNA
<213> ORGANISM: Artificial Sequence
<220> FEATURE:
<223> OTHER INFORMATION: Primer

<400> SEQUENCE: 67
tcgtcggcag cgtcagatgt gtataagaga cagcatgagc tccagcagga tga    53

<210> SEQ ID NO 68
<211> LENGTH: 55
<212> TYPE: DNA
<213> ORGANISM: Artificial Sequence
<220> FEATURE:
<223> OTHER INFORMATION: Primer

<400> SEQUENCE: 68
tcgtcggcag cgtcagatgt gtataagaga cagactgaga ggagaagact gtgtg    55

<210> SEQ ID NO 69
<211> LENGTH: 53
<212> TYPE: DNA
<213> ORGANISM: Artificial Sequence
<220> FEATURE:
<223> OTHER INFORMATION: Primer

<400> SEQUENCE: 69
tcgtcggcag cgtcagatgt gtataagaga caggcaaatg gccactgtga aca    53

<210> SEQ ID NO 70
<211> LENGTH: 54

```
<212> TYPE: DNA
<213> ORGANISM: Artificial Sequence
<220> FEATURE:
<223> OTHER INFORMATION: Primer

<400> SEQUENCE: 70
tcgtcggcag cgtcagatgt gtataagaga cagcctggat acctctgggc cata       54

<210> SEQ ID NO 71
<211> LENGTH: 53
<212> TYPE: DNA
<213> ORGANISM: Artificial Sequence
<220> FEATURE:
<223> OTHER INFORMATION: Primer

<400> SEQUENCE: 71
tcgtcggcag cgtcagatgt gtataagaga cagatagggc agagaaggag cac        53

<210> SEQ ID NO 72
<211> LENGTH: 53
<212> TYPE: DNA
<213> ORGANISM: Artificial Sequence
<220> FEATURE:
<223> OTHER INFORMATION: Primer

<400> SEQUENCE: 72
tcgtcggcag cgtcagatgt gtataagaga caggcttgga ctgcacacaa cag        53

<210> SEQ ID NO 73
<211> LENGTH: 54
<212> TYPE: DNA
<213> ORGANISM: Artificial Sequence
<220> FEATURE:
<223> OTHER INFORMATION: Primer

<400> SEQUENCE: 73
tcgtcggcag cgtcagatgt gtataagaga cagggtccct tctggcctag taga       54

<210> SEQ ID NO 74
<211> LENGTH: 54
<212> TYPE: DNA
<213> ORGANISM: Artificial Sequence
<220> FEATURE:
<223> OTHER INFORMATION: Primer

<400> SEQUENCE: 74
gtctcgtggg ctcggagatg tgtataagag acagagggag cagattaagc gagt       54

<210> SEQ ID NO 75
<211> LENGTH: 54
<212> TYPE: DNA
<213> ORGANISM: Artificial Sequence
<220> FEATURE:
<223> OTHER INFORMATION: Primer

<400> SEQUENCE: 75
gtctcgtggg ctcggagatg tgtataagag acagtgggca aacttgtggt agca       54

<210> SEQ ID NO 76
<211> LENGTH: 54
<212> TYPE: DNA
<213> ORGANISM: Artificial Sequence
<220> FEATURE:
<223> OTHER INFORMATION: Primer

<400> SEQUENCE: 76
```
gtctcgtggg ctcggagatg tgtataagag acagttccgc cactgaacat tgga    54

<210> SEQ ID NO 77
<211> LENGTH: 54
<212> TYPE: DNA
<213> ORGANISM: Artificial Sequence
<220> FEATURE:
<223> OTHER INFORMATION: Primer

<400> SEQUENCE: 77
gtctcgtggg ctcggagatg tgtataagag acaggctgcc catgagttag agga    54

<210> SEQ ID NO 78
<211> LENGTH: 54
<212> TYPE: DNA
<213> ORGANISM: Artificial Sequence
<220> FEATURE:
<223> OTHER INFORMATION: Primer

<400> SEQUENCE: 78
gtctcgtggg ctcggagatg tgtataagag acagttcaaa ggtgtcagcc agca    54

<210> SEQ ID NO 79
<211> LENGTH: 56
<212> TYPE: DNA
<213> ORGANISM: Artificial Sequence
<220> FEATURE:
<223> OTHER INFORMATION: Primer

<400> SEQUENCE: 79
gtctcgtggg ctcggagatg tgtataagag acagccagac tgtgtttctc ccttct    56

<210> SEQ ID NO 80
<211> LENGTH: 55
<212> TYPE: DNA
<213> ORGANISM: Artificial Sequence
<220> FEATURE:
<223> OTHER INFORMATION: Primer

<400> SEQUENCE: 80
gtctcgtggg ctcggagatg tgtataagag acagggcctg ctgaaaatga ctgaa    55

<210> SEQ ID NO 81
<211> LENGTH: 54
<212> TYPE: DNA
<213> ORGANISM: Artificial Sequence
<220> FEATURE:
<223> OTHER INFORMATION: Primer

<400> SEQUENCE: 81
gtctcgtggg ctcggagatg tgtataagag acagagggtc tgacgggtag agtg    54

<210> SEQ ID NO 82
<211> LENGTH: 54
<212> TYPE: DNA
<213> ORGANISM: Artificial Sequence
<220> FEATURE:
<223> OTHER INFORMATION: Primer

<400> SEQUENCE: 82
gtctcgtggg ctcggagatg tgtataagag acagtcacct ttctggccat gacc    54

<210> SEQ ID NO 83
<211> LENGTH: 54
<212> TYPE: DNA
<213> ORGANISM: Artificial Sequence -continued

```
<220> FEATURE:
<223> OTHER INFORMATION: Primer

<400> SEQUENCE: 83
gtctcgtggg ctcggagatg tgtataagag acagtcgctc tttgttgctt ccca       54

<210> SEQ ID NO 84
<211> LENGTH: 54
<212> TYPE: DNA
<213> ORGANISM: Artificial Sequence
<220> FEATURE:
<223> OTHER INFORMATION: Primer

<400> SEQUENCE: 84
gtctcgtggg ctcggagatg tgtataagag acagaccttg ccgtaagagc cttc       54

<210> SEQ ID NO 85
<211> LENGTH: 54
<212> TYPE: DNA
<213> ORGANISM: Artificial Sequence
<220> FEATURE:
<223> OTHER INFORMATION: Primer

<400> SEQUENCE: 85
gtctcgtggg ctcggagatg tgtataagag acagggatga ggctcccacc tttc       54

<210> SEQ ID NO 86
<211> LENGTH: 54
<212> TYPE: DNA
<213> ORGANISM: Artificial Sequence
<220> FEATURE:
<223> OTHER INFORMATION: Primer

<400> SEQUENCE: 86
gtctcgtggg ctcggagatg tgtataagag acaggcagaa gctgtccttg ttgc       54

<210> SEQ ID NO 87
<211> LENGTH: 54
<212> TYPE: DNA
<213> ORGANISM: Artificial Sequence
<220> FEATURE:
<223> OTHER INFORMATION: Primer

<400> SEQUENCE: 87
gtctcgtggg ctcggagatg tgtataagag acagctctcc ccttgcagct gatc       54

<210> SEQ ID NO 88
<211> LENGTH: 54
<212> TYPE: DNA
<213> ORGANISM: Artificial Sequence
<220> FEATURE:
<223> OTHER INFORMATION: Primer

<400> SEQUENCE: 88
gtctcgtggg ctcggagatg tgtataagag acagggccag atggagtctc ccta       54

<210> SEQ ID NO 89
<211> LENGTH: 54
<212> TYPE: DNA
<213> ORGANISM: Artificial Sequence
<220> FEATURE:
<223> OTHER INFORMATION: Primer

<400> SEQUENCE: 89
gtctcgtggg ctcggagatg tgtataagag acagacattg ctgccagaaa ctgc       54
```

<210> SEQ ID NO 90
<211> LENGTH: 54
<212> TYPE: DNA
<213> ORGANISM: Artificial Sequence
<220> FEATURE:
<223> OTHER INFORMATION: Primer

<400> SEQUENCE: 90
gtctcgtggg ctcggagatg tgtataagag acagttggct tgcggactct gtag    54

<210> SEQ ID NO 91
<211> LENGTH: 54
<212> TYPE: DNA
<213> ORGANISM: Artificial Sequence
<220> FEATURE:
<223> OTHER INFORMATION: Primer

<400> SEQUENCE: 91
gtctcgtggg ctcggagatg tgtataagag acagtcctct tcctcaggat tgcc    54

<210> SEQ ID NO 92
<211> LENGTH: 54
<212> TYPE: DNA
<213> ORGANISM: Artificial Sequence
<220> FEATURE:
<223> OTHER INFORMATION: Primer

<400> SEQUENCE: 92
gtctcgtggg ctcggagatg tgtataagag acagagtgca gtgtggaatc caga    54

<210> SEQ ID NO 93
<211> LENGTH: 54
<212> TYPE: DNA
<213> ORGANISM: Artificial Sequence
<220> FEATURE:
<223> OTHER INFORMATION: Primer

<400> SEQUENCE: 93
gtctcgtggg ctcggagatg tgtataagag acaggtgaca tggaaagccc ctgt    54

<210> SEQ ID NO 94
<211> LENGTH: 54
<212> TYPE: DNA
<213> ORGANISM: Artificial Sequence
<220> FEATURE:
<223> OTHER INFORMATION: Primer

<400> SEQUENCE: 94
gtctcgtggg ctcggagatg tgtataagag acagttggac acggctttac ctcc    54

<210> SEQ ID NO 95
<211> LENGTH: 55
<212> TYPE: DNA
<213> ORGANISM: Artificial Sequence
<220> FEATURE:
<223> OTHER INFORMATION: Primer

<400> SEQUENCE: 95
gtctcgtggg ctcggagatg tgtataagag acaggcagag aatgggtact cacgt    55

<210> SEQ ID NO 96
<211> LENGTH: 54
<212> TYPE: DNA
<213> ORGANISM: Artificial Sequence
<220> FEATURE:
<223> OTHER INFORMATION: Primer -continued

<400> SEQUENCE: 96
gtctcgtggg ctcggagatg tgtataagag acagcaagtg gctttggtcc gtct            54

<210> SEQ ID NO 97
<211> LENGTH: 56
<212> TYPE: DNA
<213> ORGANISM: Artificial Sequence
<220> FEATURE:
<223> OTHER INFORMATION: Primer

<400> SEQUENCE: 97
gtctcgtggg ctcggagatg tgtataagag acagtggatt gtggcacaga gattct          56

<210> SEQ ID NO 98
<211> LENGTH: 54
<212> TYPE: DNA
<213> ORGANISM: Artificial Sequence
<220> FEATURE:
<223> OTHER INFORMATION: Primer

<400> SEQUENCE: 98
gtctcgtggg ctcggagatg tgtataagag acagcttcac tggcagcttt gcac            54

<210> SEQ ID NO 99
<211> LENGTH: 54
<212> TYPE: DNA
<213> ORGANISM: Artificial Sequence
<220> FEATURE:
<223> OTHER INFORMATION: Primer

<400> SEQUENCE: 99
gtctcgtggg ctcggagatg tgtataagag acagagacgg gactcgagtg atga            54

<210> SEQ ID NO 100
<211> LENGTH: 54
<212> TYPE: DNA
<213> ORGANISM: Artificial Sequence
<220> FEATURE:
<223> OTHER INFORMATION: Primer

<400> SEQUENCE: 100
gtctcgtggg ctcggagatg tgtataagag acagattgct ggcaccatct gacg            54

<210> SEQ ID NO 101
<211> LENGTH: 54
<212> TYPE: DNA
<213> ORGANISM: Artificial Sequence
<220> FEATURE:
<223> OTHER INFORMATION: Primer

<400> SEQUENCE: 101
gtctcgtggg ctcggagatg tgtataagag acagccttcc tccttcctca gtgc            54

<210> SEQ ID NO 102
<211> LENGTH: 55
<212> TYPE: DNA
<213> ORGANISM: Artificial Sequence
<220> FEATURE:
<223> OTHER INFORMATION: Primer

<400> SEQUENCE: 102
gtctcgtggg ctcggagatg tgtataagag acagaacctt gcagaatggt cgatg           55

<210> SEQ ID NO 103

<211> LENGTH: 54
<212> TYPE: DNA
<213> ORGANISM: Artificial Sequence
<220> FEATURE:
<223> OTHER INFORMATION: Primer

<400> SEQUENCE: 103
gtctcgtggg ctcggagatg tgtataagag acagtttccg gaaagtccac gctc    54

<210> SEQ ID NO 104
<211> LENGTH: 57
<212> TYPE: DNA
<213> ORGANISM: Artificial Sequence
<220> FEATURE:
<223> OTHER INFORMATION: Primer

<400> SEQUENCE: 104
gtctcgtggg ctcggagatg tgtataagag acagcaaaag ttgtggacag gttttga    57

<210> SEQ ID NO 105
<211> LENGTH: 54
<212> TYPE: DNA
<213> ORGANISM: Artificial Sequence
<220> FEATURE:
<223> OTHER INFORMATION: Primer

<400> SEQUENCE: 105
gtctcgtggg ctcggagatg tgtataagag acagcagtct ccgcatcgtg tact    54

<210> SEQ ID NO 106
<211> LENGTH: 53
<212> TYPE: DNA
<213> ORGANISM: Artificial Sequence
<220> FEATURE:
<223> OTHER INFORMATION: Primer

<400> SEQUENCE: 106
gtctcgtggg ctcggagatg tgtataagag acagcaccag accatgagag gcc    53

<210> SEQ ID NO 107
<211> LENGTH: 54
<212> TYPE: DNA
<213> ORGANISM: Artificial Sequence
<220> FEATURE:
<223> OTHER INFORMATION: Primer

<400> SEQUENCE: 107
gtctcgtggg ctcggagatg tgtataagag acaggacata gtccaggagg cagc    54

<210> SEQ ID NO 108
<211> LENGTH: 54
<212> TYPE: DNA
<213> ORGANISM: Artificial Sequence
<220> FEATURE:
<223> OTHER INFORMATION: Primer

<400> SEQUENCE: 108
gtctcgtggg ctcggagatg tgtataagag acaggctgac ctaaagccac ctcc    54

<210> SEQ ID NO 109
<211> LENGTH: 56
<212> TYPE: DNA
<213> ORGANISM: Artificial Sequence
<220> FEATURE:
<223> OTHER INFORMATION: Primer

<400> SEQUENCE: 109
gtctcgtggg ctcggagatg tgtataagag acagttttca gccacaggaa aaaccc          56

<210> SEQ ID NO 110
<211> LENGTH: 53
<212> TYPE: DNA
<213> ORGANISM: Artificial Sequence
<220> FEATURE:
<223> OTHER INFORMATION: Primer

<400> SEQUENCE: 110
gtctcgtggg ctcggagatg tgtataagag acagtttcac ccgcagccta gtg             53

<210> SEQ ID NO 111
<211> LENGTH: 54
<212> TYPE: DNA
<213> ORGANISM: Artificial Sequence
<220> FEATURE:
<223> OTHER INFORMATION: Primer

<400> SEQUENCE: 111
gtctcgtggg ctcggagatg tgtataagag acagtggatc tcttcatgca ccgg            54

<210> SEQ ID NO 112
<211> LENGTH: 54
<212> TYPE: DNA
<213> ORGANISM: Artificial Sequence
<220> FEATURE:
<223> OTHER INFORMATION: Primer

<400> SEQUENCE: 112
gtctcgtggg ctcggagatg tgtataagag acaggccagc atgatgagac aggt            54

<210> SEQ ID NO 113
<211> LENGTH: 54
<212> TYPE: DNA
<213> ORGANISM: Artificial Sequence
<220> FEATURE:
<223> OTHER INFORMATION: Primer

<400> SEQUENCE: 113
gtctcgtggg ctcggagatg tgtataagag acagttgaac ttccctccct ccct            54

<210> SEQ ID NO 114
<211> LENGTH: 54
<212> TYPE: DNA
<213> ORGANISM: Artificial Sequence
<220> FEATURE:
<223> OTHER INFORMATION: Primer

<400> SEQUENCE: 114
gtctcgtggg ctcggagatg tgtataagag acagacaaac tggtggtggt tgga            54

<210> SEQ ID NO 115
<211> LENGTH: 54
<212> TYPE: DNA
<213> ORGANISM: Artificial Sequence
<220> FEATURE:
<223> OTHER INFORMATION: Primer

<400> SEQUENCE: 115
gtctcgtggg ctcggagatg tgtataagag acagctccac cccaagagag caac            54

<210> SEQ ID NO 116
<211> LENGTH: 54
<212> TYPE: DNA

```
<213> ORGANISM: Artificial Sequence
<220> FEATURE:
<223> OTHER INFORMATION: Primer

<400> SEQUENCE: 116
gtctcgtggg ctcggagatg tgtataagag acagatctag ggcctcttgt gcct          54

<210> SEQ ID NO 117
<211> LENGTH: 54
<212> TYPE: DNA
<213> ORGANISM: Artificial Sequence
<220> FEATURE:
<223> OTHER INFORMATION: Primer

<400> SEQUENCE: 117
gtctcgtggg ctcggagatg tgtataagag acagcacaca caggtaacgg ctga          54

<210> SEQ ID NO 118
<211> LENGTH: 56
<212> TYPE: DNA
<213> ORGANISM: Artificial Sequence
<220> FEATURE:
<223> OTHER INFORMATION: Primer

<400> SEQUENCE: 118
gtctcgtggg ctcggagatg tgtataagag acagtcatcg agatttagca gccaga        56

<210> SEQ ID NO 119
<211> LENGTH: 54
<212> TYPE: DNA
<213> ORGANISM: Artificial Sequence
<220> FEATURE:
<223> OTHER INFORMATION: Primer

<400> SEQUENCE: 119
gtctcgtggg ctcggagatg tgtataagag acagagcagg tggtcattga tggg          54

<210> SEQ ID NO 120
<211> LENGTH: 54
<212> TYPE: DNA
<213> ORGANISM: Artificial Sequence
<220> FEATURE:
<223> OTHER INFORMATION: Primer

<400> SEQUENCE: 120
gtctcgtggg ctcggagatg tgtataagag acagtataag ctggtggtgg tggg          54

<210> SEQ ID NO 121
<211> LENGTH: 56
<212> TYPE: DNA
<213> ORGANISM: Artificial Sequence
<220> FEATURE:
<223> OTHER INFORMATION: Primer

<400> SEQUENCE: 121
gtctcgtggg ctcggagatg tgtataagag acagcctcac agagttcaag ctgaag        56

<210> SEQ ID NO 122
<211> LENGTH: 54
<212> TYPE: DNA
<213> ORGANISM: Artificial Sequence
<220> FEATURE:
<223> OTHER INFORMATION: Primer

<400> SEQUENCE: 122
gtctcgtggg ctcggagatg tgtataagag acagcctctg ctgtcacctc ttgg          54
```

<210> SEQ ID NO 123
<211> LENGTH: 53
<212> TYPE: DNA
<213> ORGANISM: Artificial Sequence
<220> FEATURE:
<223> OTHER INFORMATION: Primer

<400> SEQUENCE: 123
gtctcgtggg ctcggagatg tgtataagag acagggcgac gagaaacatg atg        53

<210> SEQ ID NO 124
<211> LENGTH: 54
<212> TYPE: DNA
<213> ORGANISM: Artificial Sequence
<220> FEATURE:
<223> OTHER INFORMATION: Primer

<400> SEQUENCE: 124
gtctcgtggg ctcggagatg tgtataagag acagtgcaaa aatatccccc ggct       54

<210> SEQ ID NO 125
<211> LENGTH: 54
<212> TYPE: DNA
<213> ORGANISM: Artificial Sequence
<220> FEATURE:
<223> OTHER INFORMATION: Primer

<400> SEQUENCE: 125
gtctcgtggg ctcggagatg tgtataagag acagagcact tacctgtgac tcca       54

<210> SEQ ID NO 126
<211> LENGTH: 54
<212> TYPE: DNA
<213> ORGANISM: Artificial Sequence
<220> FEATURE:
<223> OTHER INFORMATION: Primer

<400> SEQUENCE: 126
gtctcgtggg ctcggagatg tgtataagag acaggaggtt cagagccatg gacc       54

<210> SEQ ID NO 127
<211> LENGTH: 57
<212> TYPE: DNA
<213> ORGANISM: Artificial Sequence
<220> FEATURE:
<223> OTHER INFORMATION: Primer

<400> SEQUENCE: 127
gtctcgtggg ctcggagatg tgtataagag acagactctt cataatgctt gctctga    57

<210> SEQ ID NO 128
<211> LENGTH: 54
<212> TYPE: DNA
<213> ORGANISM: Artificial Sequence
<220> FEATURE:
<223> OTHER INFORMATION: Primer

<400> SEQUENCE: 128
gtctcgtggg ctcggagatg tgtataagag acagaatccc agagtgctgt gctg       54

<210> SEQ ID NO 129
<211> LENGTH: 54
<212> TYPE: DNA
<213> ORGANISM: Artificial Sequence
<220> FEATURE:

<223> OTHER INFORMATION: Primer

<400> SEQUENCE: 129
gtctcgtggg ctcggagatg tgtataagag acagccctcc tcccttccca agta            54

<210> SEQ ID NO 130
<211> LENGTH: 54
<212> TYPE: DNA
<213> ORGANISM: Artificial Sequence
<220> FEATURE:
<223> OTHER INFORMATION: Primer

<400> SEQUENCE: 130
gtctcgtggg ctcggagatg tgtataagag acagaccaga tcagggcga agta             54

<210> SEQ ID NO 131
<211> LENGTH: 55
<212> TYPE: DNA
<213> ORGANISM: Artificial Sequence
<220> FEATURE:
<223> OTHER INFORMATION: Primer

<400> SEQUENCE: 131
gtctcgtggg ctcggagatg tgtataagag acagacacaa aacaggctca ggact           55

<210> SEQ ID NO 132
<211> LENGTH: 52
<212> TYPE: DNA
<213> ORGANISM: Artificial Sequence
<220> FEATURE:
<223> OTHER INFORMATION: Primer

<400> SEQUENCE: 132
gtctcgtggg ctcggagatg tgtataagag acagtgggag gacttcaccc cg              52

<210> SEQ ID NO 133
<211> LENGTH: 56
<212> TYPE: DNA
<213> ORGANISM: Artificial Sequence
<220> FEATURE:
<223> OTHER INFORMATION: Primer

<400> SEQUENCE: 133
gtctcgtggg ctcggagatg tgtataagag acagacctta ccttatacac cgtgcc          56

<210> SEQ ID NO 134
<211> LENGTH: 54
<212> TYPE: DNA
<213> ORGANISM: Artificial Sequence
<220> FEATURE:
<223> OTHER INFORMATION: Primer

<400> SEQUENCE: 134
gtctcgtggg ctcggagatg tgtataagag acagcatgtg aggatcctgg ctcc            54

<210> SEQ ID NO 135
<211> LENGTH: 54
<212> TYPE: DNA
<213> ORGANISM: Artificial Sequence
<220> FEATURE:
<223> OTHER INFORMATION: Primer

<400> SEQUENCE: 135
gtctcgtggg ctcggagatg tgtataagag acagtctttc tcttccgcac ccag            54

```
<210> SEQ ID NO 136
<211> LENGTH: 59
<212> TYPE: DNA
<213> ORGANISM: Artificial Sequence
<220> FEATURE:
<223> OTHER INFORMATION: Primer

<400> SEQUENCE: 136
gtctcgtggg ctcggagatg tgtataagag acagactgta atgactgtgt tcttaaggt      59

<210> SEQ ID NO 137
<211> LENGTH: 54
<212> TYPE: DNA
<213> ORGANISM: Artificial Sequence
<220> FEATURE:
<223> OTHER INFORMATION: Primer

<400> SEQUENCE: 137
gtctcgtggg ctcggagatg tgtataagag acagaggacg tacactgcct ttcg           54

<210> SEQ ID NO 138
<211> LENGTH: 54
<212> TYPE: DNA
<213> ORGANISM: Artificial Sequence
<220> FEATURE:
<223> OTHER INFORMATION: Primer

<400> SEQUENCE: 138
gtctcgtggg ctcggagatg tgtataagag acagccacct ggaacttggt ctca           54

<210> SEQ ID NO 139
<211> LENGTH: 54
<212> TYPE: DNA
<213> ORGANISM: Artificial Sequence
<220> FEATURE:
<223> OTHER INFORMATION: Primer

<400> SEQUENCE: 139
gtctcgtggg ctcggagatg tgtataagag acagggctct acacaagctt cctt           54

<210> SEQ ID NO 140
<211> LENGTH: 55
<212> TYPE: DNA
<213> ORGANISM: Artificial Sequence
<220> FEATURE:
<223> OTHER INFORMATION: Primer

<400> SEQUENCE: 140
gtctcgtggg ctcggagatg tgtataagag acagttacat ccctctctgc tctgc          55

<210> SEQ ID NO 141
<211> LENGTH: 54
<212> TYPE: DNA
<213> ORGANISM: Artificial Sequence
<220> FEATURE:
<223> OTHER INFORMATION: Primer

<400> SEQUENCE: 141
gtctcgtggg ctcggagatg tgtataagag acagtcaggt cctcaaagca ccag           54

<210> SEQ ID NO 142
<211> LENGTH: 55
<212> TYPE: DNA
<213> ORGANISM: Artificial Sequence
<220> FEATURE:
<223> OTHER INFORMATION: Primer
```

```
<400> SEQUENCE: 142
gtctcgtggg ctcggagatg tgtataagag acagaaggag agagttgtga ggcca          55

<210> SEQ ID NO 143
<211> LENGTH: 54
<212> TYPE: DNA
<213> ORGANISM: Artificial Sequence
<220> FEATURE:
<223> OTHER INFORMATION: Primer

<400> SEQUENCE: 143
gtctcgtggg ctcggagatg tgtataagag acagtttcgg cccaaccagt atcc           54

<210> SEQ ID NO 144
<211> LENGTH: 54
<212> TYPE: DNA
<213> ORGANISM: Artificial Sequence
<220> FEATURE:
<223> OTHER INFORMATION: Primer

<400> SEQUENCE: 144
gtctcgtggg ctcggagatg tgtataagag acagaatgga gccactgaac tgca           54

<210> SEQ ID NO 145
<211> LENGTH: 54
<212> TYPE: DNA
<213> ORGANISM: Artificial Sequence
<220> FEATURE:
<223> OTHER INFORMATION: Primer

<400> SEQUENCE: 145
gtctcgtggg ctcggagatg tgtataagag acaggctggg acctgttcac ttgt           54

<210> SEQ ID NO 146
<211> LENGTH: 54
<212> TYPE: DNA
<213> ORGANISM: Artificial Sequence
<220> FEATURE:
<223> OTHER INFORMATION: Primer

<400> SEQUENCE: 146
gtctcgtggg ctcggagatg tgtataagag acagctacca tgtctcccca ggct           54
```